US008956878B2

(12) United States Patent
Griffiths et al.

(10) Patent No.: US 8,956,878 B2
(45) Date of Patent: Feb. 17, 2015

(54) POLYPEPTIDES WITH AFFINITY FOR HEAT SHOCK PROTEINS (HSPS) AND HSP ASSOCIATED COMPLEXES (HACS) AND THEIR USE IN DIAGNOSIS AND THERAPY

(75) Inventors: Steven Gareth Griffiths, Moncton (CA); Scott Edwin Lewis, Westminster, MA (US)

(73) Assignees: Atlantic Cancer Research Institute, Moncton, New Brunswick (CA); New England Peptide, Inc., Gardner, MA (US)

( * ) Notice: Subject to any disclaimer, the term of this patent is extended or adjusted under 35 U.S.C. 154(b) by 0 days.

(21) Appl. No.: 13/824,829

(22) PCT Filed: Mar. 21, 2012

(86) PCT No.: PCT/CA2012/050175
§ 371 (c)(1),
(2), (4) Date: May 31, 2013

(87) PCT Pub. No.: WO2012/126118
PCT Pub. Date: Sep. 27, 2012

(65) Prior Publication Data
US 2013/0243802 A1 Sep. 19, 2013

Related U.S. Application Data

(60) Provisional application No. 61/454,718, filed on Mar. 21, 2011.

(51) Int. Cl.
*G01N 33/567* (2006.01)
*A61K 38/16* (2006.01)
*C07H 21/04* (2006.01)
*C12N 15/00* (2006.01)
*A61K 38/00* (2006.01)
*A61K 38/04* (2006.01)
*C07K 14/435* (2006.01)
*A61K 39/00* (2006.01)
*C07K 14/34* (2006.01)
*C07K 7/06* (2006.01)
*C07K 7/08* (2006.01)
*C07K 14/00* (2006.01)
*C07K 7/00* (2006.01)

(52) U.S. Cl.
CPC ........... *C07K 14/435* (2013.01); *A61K 39/0011* (2013.01); *C07K 14/34* (2013.01); *C07K 7/06* (2013.01); *C07K 7/08* (2013.01); *C07K 14/001* (2013.01); *C07K 7/00* (2013.01); *A61K 2039/6043* (2013.01); *C07K 2319/35* (2013.01); *C07K 2319/70* (2013.01); *G01N 2333/34* (2013.01); *G01N 2333/47* (2013.01); *G01N 2333/936* (2013.01)
USPC ...... 436/504; 514/21.3; 536/23.5; 435/320.1; 530/324; 530/326; 530/328

(58) Field of Classification Search
None
See application file for complete search history.

(56) References Cited

U.S. PATENT DOCUMENTS

| 7,723,469 | B2 | 5/2010 | Walensky et al. | |
| 7,892,559 | B2 * | 2/2011 | Straten et al. | 424/185.1 |
| 2010/0150868 | A1 * | 6/2010 | Achiron et al. | 424/85.6 |

FOREIGN PATENT DOCUMENTS

| WO | WO 96/12737 | 5/1996 |
| WO | WO 02/083933 | 10/2002 |
| WO | WO 2005/035003 | 4/2005 |
| WO | WO 2008/056207 | 5/2008 |
| WO | WO 2009/021322 | 2/2009 |
| WO | WO 2010/056337 | 5/2010 |

OTHER PUBLICATIONS

Xue et al. 2008. J. Translational Med. 6:52-65.*
Rak 2010. Semin Thromb Hemost 36:888-906.*
Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
Extended European Search Report issued in European application No. 12760787.7, dated Aug. 19, 2014.
Fang et al., "Comparison of anti-tumor effect between human Mucl-MBP and mouse mucl-MBP fusion protein vaccine," Database Embase, accession No. EMB 2010124709, Elsevier Science Publishers, Amsterdam, NL, Jan. 2010. (Abstract only).
Binder et al., "Heat Shock Protein-chaperoned Peptides but Not Free Peptides Introduced into the Cytosol Are Presented Efficiently by Major Histocompatibility Complex I Molecules", *The Journal of Biological Chemistry*, 276(20):17163-17171, 2001.
Mycko et al., "Inducible Heat Shock Protein 70 Promotes Myelin Autoantigen Presentation by the HLA Class II", *The Journal of Immunology*, 172:202-213, 2004.
PCT International Search Report and Written Opinion issued in International Application No. PCT/CA2012/050175, mailed Jul. 25, 2012.

* cited by examiner

*Primary Examiner* — Shulamith H Shafer
(74) *Attorney, Agent, or Firm* — Parker Highlander PLLC

(57) ABSTRACT

The present application is directed to a peptides comprising an a-helix forming-amino acid sequence that binds a heat shock protein. Also included is a polypeptide comprising (a) a first peptide portion that comprises an α-helix-forming amino acid sequence that binds a heat shock protein; and (b) at least one second peptide portion comprising an antigenic amino acid sequence and/or an a-helix-stabilizing amino acid sequence that increases the interaction of the first peptide portion with the heat shock protein. The present application also includes compositions comprising the peptides and/or polypeptides of present application and uses of the peptides and/or polypeptides of the present application for fractionating substances relevant for discovery, research or clinical analysis from a biological sample and as therapeutics.

30 Claims, 10 Drawing Sheets

```
                              SEQUENCE LISTING

<160> NUMBER OF SEQ ID NOS: 127

<210> SEQ ID NO 1
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is G, A, D, or E
<220> FEATURE:
<221> NAME/KEY: MISC_FEATURE
<222> LOCATION: (2)..(2)
<223> OTHER INFORMATION: X  is R, H or K
<220> FEATURE:
<221> NAME/KEY: MISC_FEATURE
<222> LOCATION: (3)..(3)
<223> OTHER INFORMATION: X  is G, A, S or T
<220> FEATURE:
<221> NAME/KEY: MISC_FEATURE
<222> LOCATION: (4)..(4)
<223> OTHER INFORMATION: X  is R, H, K, N or Q
<220> FEATURE:
<221> NAME/KEY: MISC_FEATURE
<222> LOCATION: (5)..(5)
<223> OTHER INFORMATION: X  is G, A, S or T
<220> FEATURE:
<221> NAME/KEY: MISC_FEATURE
<222> LOCATION: (6)..(6)
<223> OTHER INFORMATION: X is A, V, I, L, M, F or W
<220> FEATURE:
<221> NAME/KEY: MISC_FEATURE
<222> LOCATION: (7)..(7)
<223> OTHER INFORMATION: X is G, A, S or T
<220> FEATURE:
<221> NAME/KEY: MISC_FEATURE
<222> LOCATION: (8)..(8)
<223> OTHER INFORMATION: X is A, V, I, L or G
<220> FEATURE:
<221> NAME/KEY: MISC_FEATURE
<222> LOCATION: (9)..(9)
<223> OTHER INFORMATION: X is S, T, M, A, V, I or L
<220> FEATURE:
<221> NAME/KEY: MISC_FEATURE
<222> LOCATION: (10)..(10)
<223> OTHER INFORMATION: X is R, H, K, N or Q
<220> FEATURE:
<221> NAME/KEY: MISC_FEATURE
<222> LOCATION: (11)..(11)
<223> OTHER INFORMATION: X is A, V, I, L  M, F or W
<220> FEATURE:
<221> NAME/KEY: MISC_FEATURE
<222> LOCATION: (12)..(12)
<223> OTHER INFORMATION: X is D, E, S, or T

<400> SEQUENCE: 1

Xaa Xaa Xaa Xaa Xaa Xaa Xaa Xaa Xaa Xaa Xaa
1               5                   10

<210> SEQ ID NO 2
<211> LENGTH: 18
<212> TYPE: PRT
<213> ORGANISM: Bos taurus

<400> SEQUENCE: 2

Pro Ser Gln Gly Lys Gly Arg Gly Leu Ser Leu Ser Arg Phe Ser Trp
1               5                   10                  15
```

Gly Ala

<210> SEQ ID NO 3
<211> LENGTH: 8
<212> TYPE: PRT
<213> ORGANISM: Bos taurus

<400> SEQUENCE: 3

Pro Ser Gln Gly Lys Gly Arg Gly
1               5

<210> SEQ ID NO 4
<211> LENGTH: 9
<212> TYPE: PRT
<213> ORGANISM: Bos taurus

<400> SEQUENCE: 4

Gly Arg Gly Leu Ser Leu Ser Arg Phe
1               5

<210> SEQ ID NO 5
<211> LENGTH: 9
<212> TYPE: PRT
<213> ORGANISM: Bos taurus

<400> SEQUENCE: 5

Ser Leu Ser Arg Phe Ser Trp Gly Ala
1               5

<210> SEQ ID NO 6
<211> LENGTH: 18
<212> TYPE: PRT
<213> ORGANISM: Gallus gallus

<400> SEQUENCE: 6

Gly Trp Gly Asp Arg Gly Asn Gly Phe Gly Leu Met Gln Val Asp Lys
1               5                   10                  15

Arg Tyr

<210> SEQ ID NO 7
<211> LENGTH: 9
<212> TYPE: PRT
<213> ORGANISM: Homo sapiens

<400> SEQUENCE: 7

Ser Thr Phe Lys Asn Trp Pro Phe Leu
1               5

<210> SEQ ID NO 8
<211> LENGTH: 9
<212> TYPE: PRT
<213> ORGANISM: Homo sapiens

<400> SEQUENCE: 8

Leu Thr Leu Gly Glu Phe Leu Lys Leu
1               5

<210> SEQ ID NO 9
<211> LENGTH: 9
<212> TYPE: PRT
<213> ORGANISM: Homo sapiens

<400> SEQUENCE: 9

Leu Arg Arg Lys Cys Ala Val Pro Ser

```
1               5

<210> SEQ ID NO 10
<211> LENGTH: 9
<212> TYPE: PRT
<213> ORGANISM: Homo sapiens

<400> SEQUENCE: 10

Gly Val Thr Ser Ala Pro Asp Thr Arg
1               5

<210> SEQ ID NO 11
<211> LENGTH: 9
<212> TYPE: PRT
<213> ORGANISM: Homo sapiens

<400> SEQUENCE: 11

Met Phe Leu Gln Ile Tyr Lys Gln Gly
1               5

<210> SEQ ID NO 12
<211> LENGTH: 9
<212> TYPE: PRT
<213> ORGANISM: Homo sapiens

<400> SEQUENCE: 12

Phe Leu Gln Ile Tyr Lys Gln Gly Gly
1               5

<210> SEQ ID NO 13
<211> LENGTH: 9
<212> TYPE: PRT
<213> ORGANISM: Homo sapiens

<400> SEQUENCE: 13

Leu Gln Ile Tyr Lys Gln Gly Gly Phe
1               5

<210> SEQ ID NO 14
<211> LENGTH: 9
<212> TYPE: PRT
<213> ORGANISM: Homo sapiens

<400> SEQUENCE: 14

Gln Ile Tyr Lys Gln Gly Gly Phe Leu
1               5

<210> SEQ ID NO 15
<211> LENGTH: 9
<212> TYPE: PRT
<213> ORGANISM: Homo sapiens

<400> SEQUENCE: 15

Ile Tyr Lys Gln Gly Gly Phe Leu Gly
1               5

<210> SEQ ID NO 16
<211> LENGTH: 9
<212> TYPE: PRT
<213> ORGANISM: Homo sapiens

<400> SEQUENCE: 16

Tyr Lys Gln Gly Gly Phe Leu Gly Leu
1               5
```

<210> SEQ ID NO 17
<211> LENGTH: 9
<212> TYPE: PRT
<213> ORGANISM: Homo sapiens

<400> SEQUENCE: 17

Val Val Gln Leu Thr Leu Ala Phe Arg
1               5

<210> SEQ ID NO 18
<211> LENGTH: 9
<212> TYPE: PRT
<213> ORGANISM: Homo sapiens

<400> SEQUENCE: 18

Phe Asn Gln Tyr Lys Thr Glu Ala Ala
1               5

<210> SEQ ID NO 19
<211> LENGTH: 9
<212> TYPE: PRT
<213> ORGANISM: Homo sapiens

<400> SEQUENCE: 19

Asn Gln Tyr Lys Thr Glu Ala Ala Ser
1               5

<210> SEQ ID NO 20
<211> LENGTH: 9
<212> TYPE: PRT
<213> ORGANISM: Homo sapiens

<400> SEQUENCE: 20

Gln Tyr Lys Thr Glu Ala Ala Ser Arg
1               5

<210> SEQ ID NO 21
<211> LENGTH: 9
<212> TYPE: PRT
<213> ORGANISM: Homo sapiens

<400> SEQUENCE: 21

Tyr Lys Thr Glu Ala Ala Ser Arg Tyr
1               5

<210> SEQ ID NO 22
<211> LENGTH: 9
<212> TYPE: PRT
<213> ORGANISM: Homo sapiens

<400> SEQUENCE: 22

Gly Gln Leu Asp Ile Phe Pro Ala Arg
1               5

<210> SEQ ID NO 23
<211> LENGTH: 9
<212> TYPE: PRT
<213> ORGANISM: Homo sapiens

<400> SEQUENCE: 23

Lys Gly Leu Ile Leu Cys Leu Trp Ser
1               5

<210> SEQ ID NO 24

```
<211> LENGTH: 9
<212> TYPE: PRT
<213> ORGANISM: Homo sapiens

<400> SEQUENCE: 24

Gly Leu Ile Leu Cys Leu Trp Ser Lys
1               5

<210> SEQ ID NO 25
<211> LENGTH: 9
<212> TYPE: PRT
<213> ORGANISM: Homo sapiens

<400> SEQUENCE: 25

Leu Ile Leu Cys Leu Trp Ser Lys Phe
1               5

<210> SEQ ID NO 26
<211> LENGTH: 9
<212> TYPE: PRT
<213> ORGANISM: Homo sapiens

<400> SEQUENCE: 26

Ile Leu Cys Leu Trp Ser Lys Phe Cys
1               5

<210> SEQ ID NO 27
<211> LENGTH: 9
<212> TYPE: PRT
<213> ORGANISM: Homo sapiens

<400> SEQUENCE: 27

Leu Cys Leu Trp Ser Lys Phe Cys Arg
1               5

<210> SEQ ID NO 28
<211> LENGTH: 9
<212> TYPE: PRT
<213> ORGANISM: Homo sapiens

<400> SEQUENCE: 28

Cys Leu Trp Ser Lys Phe Cys Arg Trp
1               5

<210> SEQ ID NO 29
<211> LENGTH: 9
<212> TYPE: PRT
<213> ORGANISM: Homo sapiens

<400> SEQUENCE: 29

Leu Trp Ser Lys Phe Cys Arg Trp Phe
1               5

<210> SEQ ID NO 30
<211> LENGTH: 9
<212> TYPE: PRT
<213> ORGANISM: Homo sapiens

<400> SEQUENCE: 30

Trp Ser Lys Phe Cys Arg Trp Phe Gln
1               5

<210> SEQ ID NO 31
<211> LENGTH: 9
<212> TYPE: PRT
```

```
<213> ORGANISM: Homo sapiens

<400> SEQUENCE: 31

Ser Lys Phe Cys Arg Trp Phe Gln Arg
1               5

<210> SEQ ID NO 32
<211> LENGTH: 9
<212> TYPE: PRT
<213> ORGANISM: Homo sapiens

<400> SEQUENCE: 32

Glu Ser Pro Leu Leu Ala Ala Lys
1               5

<210> SEQ ID NO 33
<211> LENGTH: 9
<212> TYPE: PRT
<213> ORGANISM: Homo sapiens

<400> SEQUENCE: 33

Gln Ala Leu Asn Lys Leu Leu Lys Tyr
1               5

<210> SEQ ID NO 34
<211> LENGTH: 9
<212> TYPE: PRT
<213> ORGANISM: Homo sapiens

<400> SEQUENCE: 34

Asn Leu Val Arg Ala Leu Leu Ala Arg
1               5

<210> SEQ ID NO 35
<211> LENGTH: 9
<212> TYPE: PRT
<213> ORGANISM: Homo sapiens

<400> SEQUENCE: 35

Leu Val Arg Ala Leu Leu Ala Arg Arg
1               5

<210> SEQ ID NO 36
<211> LENGTH: 9
<212> TYPE: PRT
<213> ORGANISM: Homo sapiens

<400> SEQUENCE: 36

Val Arg Ala Leu Leu Ala Arg Arg Ala
1               5

<210> SEQ ID NO 37
<211> LENGTH: 9
<212> TYPE: PRT
<213> ORGANISM: Homo sapiens

<400> SEQUENCE: 37

Arg Ala Leu Leu Ala Arg Arg Ala Ser
1               5

<210> SEQ ID NO 38
<211> LENGTH: 9
<212> TYPE: PRT
<213> ORGANISM: Homo sapiens
```

```
<400> SEQUENCE: 38

Ala Leu Leu Ala Arg Arg Ala Ser Val
1               5

<210> SEQ ID NO 39
<211> LENGTH: 9
<212> TYPE: PRT
<213> ORGANISM: Homo sapiens

<400> SEQUENCE: 39

Leu Leu Ala Arg Arg Ala Ser Val Ser
1               5

<210> SEQ ID NO 40
<211> LENGTH: 9
<212> TYPE: PRT
<213> ORGANISM: Homo sapiens

<400> SEQUENCE: 40

Leu Ala Arg Arg Ala Ser Val Ser Ala
1               5

<210> SEQ ID NO 41
<211> LENGTH: 9
<212> TYPE: PRT
<213> ORGANISM: Homo sapiens

<400> SEQUENCE: 41

Ala Arg Arg Ala Ser Val Ser Ala Arg
1               5

<210> SEQ ID NO 42
<211> LENGTH: 9
<212> TYPE: PRT
<213> ORGANISM: Homo sapiens

<400> SEQUENCE: 42

Arg Arg Ala Ser Val Ser Ala Arg Ala
1               5

<210> SEQ ID NO 43
<211> LENGTH: 9
<212> TYPE: PRT
<213> ORGANISM: Homo sapiens

<400> SEQUENCE: 43

Arg Ala Ser Val Ser Ala Arg Ala Thr
1               5

<210> SEQ ID NO 44
<211> LENGTH: 9
<212> TYPE: PRT
<213> ORGANISM: Homo sapiens

<400> SEQUENCE: 44

Ala Ser Val Ser Ala Arg Ala Thr Gly
1               5

<210> SEQ ID NO 45
<211> LENGTH: 9
<212> TYPE: PRT
<213> ORGANISM: Homo sapiens

<400> SEQUENCE: 45
```

Ser Val Ser Ala Arg Ala Thr Gly Thr
1               5

<210> SEQ ID NO 46
<211> LENGTH: 9
<212> TYPE: PRT
<213> ORGANISM: Homo sapiens

<400> SEQUENCE: 46

Val Ser Ala Arg Ala Thr Gly Thr Ala
1               5

<210> SEQ ID NO 47
<211> LENGTH: 9
<212> TYPE: PRT
<213> ORGANISM: Homo sapiens

<400> SEQUENCE: 47

Ser Ala Arg Ala Thr Gly Thr Ala Phe
1               5

<210> SEQ ID NO 48
<211> LENGTH: 9
<212> TYPE: PRT
<213> ORGANISM: Homo sapiens

<400> SEQUENCE: 48

Ala Arg Ala Thr Gly Thr Ala Phe Arg
1               5

<210> SEQ ID NO 49
<211> LENGTH: 9
<212> TYPE: PRT
<213> ORGANISM: Homo sapiens

<400> SEQUENCE: 49

Leu Gln Pro Asn Lys Thr Phe Ala Cys
1               5

<210> SEQ ID NO 50
<211> LENGTH: 9
<212> TYPE: PRT
<213> ORGANISM: Homo sapiens

<400> SEQUENCE: 50

Tyr Asn Leu Leu Leu Ser Tyr Asp Arg
1               5

<210> SEQ ID NO 51
<211> LENGTH: 9
<212> TYPE: PRT
<213> ORGANISM: Homo sapiens

<400> SEQUENCE: 51

Lys Arg Lys His Thr Gln Trp Thr Tyr
1               5

<210> SEQ ID NO 52
<211> LENGTH: 9
<212> TYPE: PRT
<213> ORGANISM: Homo sapiens

<400> SEQUENCE: 52

Leu Leu Glu Leu Ile Ile Thr Thr Lys
1               5

<210> SEQ ID NO 53
<211> LENGTH: 9
<212> TYPE: PRT
<213> ORGANISM: Homo sapiens

<400> SEQUENCE: 53

Leu Val Ser Leu Lys Trp Lys Arg Tyr
1               5

<210> SEQ ID NO 54
<211> LENGTH: 9
<212> TYPE: PRT
<213> ORGANISM: Homo sapiens

<400> SEQUENCE: 54

Val Ser Leu Lys Trp Lys Arg Tyr Gly
1               5

<210> SEQ ID NO 55
<211> LENGTH: 9
<212> TYPE: PRT
<213> ORGANISM: Homo sapiens

<400> SEQUENCE: 55

Ser Leu Lys Trp Lys Arg Tyr Gly Arg
1               5

<210> SEQ ID NO 56
<211> LENGTH: 9
<212> TYPE: PRT
<213> ORGANISM: Homo sapiens

<400> SEQUENCE: 56

Leu Lys Trp Lys Arg Tyr Gly Arg Pro
1               5

<210> SEQ ID NO 57
<211> LENGTH: 9
<212> TYPE: PRT
<213> ORGANISM: Homo sapiens

<400> SEQUENCE: 57

Lys Trp Lys Arg Tyr Gly Arg Pro Tyr
1               5

<210> SEQ ID NO 58
<211> LENGTH: 9
<212> TYPE: PRT
<213> ORGANISM: Homo sapiens

<400> SEQUENCE: 58

Asn Thr Leu Leu Gln Gln Lys Leu Leu
1               5

<210> SEQ ID NO 59
<211> LENGTH: 9
<212> TYPE: PRT
<213> ORGANISM: Homo sapiens

<400> SEQUENCE: 59

Thr Ile Met Ile Gln Lys Met Ile Phe
1               5

```
<210> SEQ ID NO 60
<211> LENGTH: 9
<212> TYPE: PRT
<213> ORGANISM: Homo sapiens

<400> SEQUENCE: 60

Lys Leu Pro Arg Cys Leu Trp Pro Arg
1               5

<210> SEQ ID NO 61
<211> LENGTH: 9
<212> TYPE: PRT
<213> ORGANISM: Homo sapiens

<400> SEQUENCE: 61

Leu Gly Asp Arg Trp Phe Leu Arg Val
1               5

<210> SEQ ID NO 62
<211> LENGTH: 9
<212> TYPE: PRT
<213> ORGANISM: Homo sapiens

<400> SEQUENCE: 62

Arg Tyr Ala Gln Ala Phe His Thr Arg
1               5

<210> SEQ ID NO 63
<211> LENGTH: 23
<212> TYPE: PRT
<213> ORGANISM: Homo sapiens

<400> SEQUENCE: 63

Pro Ser Gln Ala Ser Ser Gly Gln Ala Arg Met Phe Pro Asn Ala Pro
1               5                   10                  15

Tyr Leu Pro Ser Cys Leu Glu
            20

<210> SEQ ID NO 64
<211> LENGTH: 27
<212> TYPE: PRT
<213> ORGANISM: Artificial Sequence
<220> FEATURE:
<223> OTHER INFORMATION: Synthetic construct

<400> SEQUENCE: 64

Pro Ser Gln Gly Lys Gly Arg Gly Leu Ser Leu Ser Arg Phe Ser Trp
1               5                   10                  15

Gly Ala Ser Thr Phe Lys Asn Trp Pro Phe Leu
            20                  25

<210> SEQ ID NO 65
<211> LENGTH: 27
<212> TYPE: PRT
<213> ORGANISM: Artificial Sequence
<220> FEATURE:
<223> OTHER INFORMATION: Synthetic construct

<400> SEQUENCE: 65

Pro Ser Gln Gly Lys Gly Arg Gly Leu Ser Leu Ser Arg Phe Ser Trp
1               5                   10                  15

Gly Ala Leu Thr Leu Gly Glu Phe Leu Lys Leu
            20                  25
```

<210> SEQ ID NO 66
<211> LENGTH: 27
<212> TYPE: PRT
<213> ORGANISM: Artificial Sequence
<220> FEATURE:
<223> OTHER INFORMATION: Synthetic construct

<400> SEQUENCE: 66

Pro Ser Gln Gly Lys Gly Arg Gly Leu Ser Leu Ser Arg Phe Ser Trp
1               5                   10                  15

Gly Ala Leu Arg Arg Lys Cys Ala Val Pro Ser
            20                  25

<210> SEQ ID NO 67
<211> LENGTH: 41
<212> TYPE: PRT
<213> ORGANISM: Artificial Sequence
<220> FEATURE:
<223> OTHER INFORMATION: Synthetic construct

<400> SEQUENCE: 67

Pro Ser Gln Gly Lys Gly Arg Gly Leu Ser Leu Ser Arg Phe Ser Trp
1               5                   10                  15

Gly Ala Pro Ser Gln Ala Ser Ser Gly Gln Ala Arg Met Phe Pro Asn
            20                  25                  30

Ala Pro Tyr Leu Pro Ser Cys Leu Glu
        35                  40

<210> SEQ ID NO 68
<211> LENGTH: 17
<212> TYPE: PRT
<213> ORGANISM: Artificial Sequence
<220> FEATURE:
<223> OTHER INFORMATION: Synthetic construct

<400> SEQUENCE: 68

Pro Ser Gln Gly Lys Gly Arg Gly Ser Thr Phe Lys Asn Trp Pro Phe
1               5                   10                  15

Leu

<210> SEQ ID NO 69
<211> LENGTH: 18
<212> TYPE: PRT
<213> ORGANISM: Artificial Sequence
<220> FEATURE:
<223> OTHER INFORMATION: Synthetic construct

<400> SEQUENCE: 69

Gly Arg Gly Leu Ser Leu Ser Arg Phe Ser Thr Phe Lys Asn Trp Pro
1               5                   10                  15

Phe Leu

<210> SEQ ID NO 70
<211> LENGTH: 18
<212> TYPE: PRT
<213> ORGANISM: Artificial Sequence
<220> FEATURE:
<223> OTHER INFORMATION: Synthetic construct

<400> SEQUENCE: 70

Ser Leu Ser Arg Phe Ser Trp Gly Ala Leu Arg Arg Lys Cys Ala Val
1               5                   10                  15

Pro Ser

```
<210> SEQ ID NO 71
<211> LENGTH: 18
<212> TYPE: PRT
<213> ORGANISM: Artificial Sequence
<220> FEATURE:
<223> OTHER INFORMATION: Synthetic construct

<400> SEQUENCE: 71

Ser Leu Ser Arg Phe Ser Trp Gly Ala Leu Thr Leu Gly Glu Phe Leu
1               5                   10                  15

Lys Leu

<210> SEQ ID NO 72
<211> LENGTH: 27
<212> TYPE: PRT
<213> ORGANISM: Artificial Sequence
<220> FEATURE:
<223> OTHER INFORMATION: Synthetic construct

<400> SEQUENCE: 72

Pro Ser Gln Gly Lys Gly Arg Gly Leu Ser Leu Ser Arg Phe Ser Trp
1               5                   10                  15

Gly Ala Gly Val Thr Ser Ala Pro Asp Thr Arg
            20                  25

<210> SEQ ID NO 73
<211> LENGTH: 27
<212> TYPE: PRT
<213> ORGANISM: Artificial Sequence
<220> FEATURE:
<223> OTHER INFORMATION: Synthetic construct

<400> SEQUENCE: 73

Pro Ser Gln Gly Lys Gly Arg Gly Leu Ser Leu Ser Arg Phe Ser Trp
1               5                   10                  15

Gly Ala Met Phe Leu Gln Ile Tyr Lys Gln Gly
            20                  25

<210> SEQ ID NO 74
<211> LENGTH: 27
<212> TYPE: PRT
<213> ORGANISM: Artificial Sequence
<220> FEATURE:
<223> OTHER INFORMATION: Synthetic construct

<400> SEQUENCE: 74

Pro Ser Gln Gly Lys Gly Arg Gly Leu Ser Leu Ser Arg Phe Ser Trp
1               5                   10                  15

Gly Ala Phe Leu Gln Ile Tyr Lys Gln Gly Gly
            20                  25

<210> SEQ ID NO 75
<211> LENGTH: 27
<212> TYPE: PRT
<213> ORGANISM: Artificial Sequence
<220> FEATURE:
<223> OTHER INFORMATION: Synthetic construct

<400> SEQUENCE: 75

Pro Ser Gln Gly Lys Gly Arg Gly Leu Ser Leu Ser Arg Phe Ser Trp
1               5                   10                  15

Gly Ala Leu Gln Ile Tyr Lys Gln Gly Gly Phe
            20                  25
```

<210> SEQ ID NO 76
<211> LENGTH: 27
<212> TYPE: PRT
<213> ORGANISM: Artificial Sequence
<220> FEATURE:
<223> OTHER INFORMATION: Synthetic construct

<400> SEQUENCE: 76

Pro Ser Gln Gly Lys Gly Arg Gly Leu Ser Leu Ser Arg Phe Ser Trp
1               5                   10                  15

Gly Ala Gln Ile Tyr Lys Gln Gly Gly Phe Leu
            20                  25

<210> SEQ ID NO 77
<211> LENGTH: 27
<212> TYPE: PRT
<213> ORGANISM: Artificial Sequence
<220> FEATURE:
<223> OTHER INFORMATION: Synthetic construct

<400> SEQUENCE: 77

Pro Ser Gln Gly Lys Gly Arg Gly Leu Ser Leu Ser Arg Phe Ser Trp
1               5                   10                  15

Gly Ala Ile Tyr Lys Gln Gly Gly Phe Leu Gly
            20                  25

<210> SEQ ID NO 78
<211> LENGTH: 27
<212> TYPE: PRT
<213> ORGANISM: Artificial Sequence
<220> FEATURE:
<223> OTHER INFORMATION: Synthetic construct

<400> SEQUENCE: 78

Pro Ser Gln Gly Lys Gly Arg Gly Leu Ser Leu Ser Arg Phe Ser Trp
1               5                   10                  15

Gly Ala Tyr Lys Gln Gly Gly Phe Leu Gly Leu
            20                  25

<210> SEQ ID NO 79
<211> LENGTH: 27
<212> TYPE: PRT
<213> ORGANISM: Artificial Sequence
<220> FEATURE:
<223> OTHER INFORMATION: Synthetic construct

<400> SEQUENCE: 79

Pro Ser Gln Gly Lys Gly Arg Gly Leu Ser Leu Ser Arg Phe Ser Trp
1               5                   10                  15

Gly Ala Val Val Gln Leu Thr Leu Ala Phe Arg
            20                  25

<210> SEQ ID NO 80
<211> LENGTH: 27
<212> TYPE: PRT
<213> ORGANISM: Artificial Sequence
<220> FEATURE:
<223> OTHER INFORMATION: Synthetic construct

<400> SEQUENCE: 80

Pro Ser Gln Gly Lys Gly Arg Gly Leu Ser Leu Ser Arg Phe Ser Trp
1               5                   10                  15

Gly Ala Phe Asn Gln Tyr Lys Thr Glu Ala Ala
            20                  25

<210> SEQ ID NO 81
<211> LENGTH: 27
<212> TYPE: PRT
<213> ORGANISM: Artificial Sequence
<220> FEATURE:
<223> OTHER INFORMATION: Synthetic construct

<400> SEQUENCE: 81

Pro Ser Gln Gly Lys Gly Arg Gly Leu Ser Leu Ser Arg Phe Ser Trp
1               5                   10                  15

Gly Ala Asn Gln Tyr Lys Thr Glu Ala Ala Ser
            20                  25

<210> SEQ ID NO 82
<211> LENGTH: 27
<212> TYPE: PRT
<213> ORGANISM: Artificial Sequence
<220> FEATURE:
<223> OTHER INFORMATION: Synthetic construct

<400> SEQUENCE: 82

Pro Ser Gln Gly Lys Gly Arg Gly Leu Ser Leu Ser Arg Phe Ser Trp
1               5                   10                  15

Gly Ala Gln Tyr Lys Thr Glu Ala Ala Ser Arg
            20                  25

<210> SEQ ID NO 83
<211> LENGTH: 27
<212> TYPE: PRT
<213> ORGANISM: Artificial Sequence
<220> FEATURE:
<223> OTHER INFORMATION: Synthetic construct

<400> SEQUENCE: 83

Pro Ser Gln Gly Lys Gly Arg Gly Leu Ser Leu Ser Arg Phe Ser Trp
1               5                   10                  15

Gly Ala Tyr Lys Thr Glu Ala Ala Ser Arg Tyr
            20                  25

<210> SEQ ID NO 84
<211> LENGTH: 27
<212> TYPE: PRT
<213> ORGANISM: Artificial Sequence
<220> FEATURE:
<223> OTHER INFORMATION: Synthetic construct

<400> SEQUENCE: 84

Pro Ser Gln Gly Lys Gly Arg Gly Leu Ser Leu Ser Arg Phe Ser Trp
1               5                   10                  15

Gly Ala Gly Gln Leu Asp Ile Phe Pro Ala Arg
            20                  25

<210> SEQ ID NO 85
<211> LENGTH: 27
<212> TYPE: PRT
<213> ORGANISM: Artificial Sequence
<220> FEATURE:
<223> OTHER INFORMATION: Synthetic construct

<400> SEQUENCE: 85

Pro Ser Gln Gly Lys Gly Arg Gly Leu Ser Leu Ser Arg Phe Ser Trp
1               5                   10                  15

Gly Ala Lys Gly Leu Ile Leu Cys Leu Trp Ser 20                  25

<210> SEQ ID NO 86
<211> LENGTH: 27
<212> TYPE: PRT
<213> ORGANISM: Artificial Sequence
<220> FEATURE:
<223> OTHER INFORMATION: Synthetic construct

<400> SEQUENCE: 86

Pro Ser Gln Gly Lys Gly Arg Gly Leu Ser Leu Ser Arg Phe Ser Trp
1               5                   10                  15

Gly Ala Gly Leu Ile Leu Cys Leu Trp Ser Lys
            20                  25

<210> SEQ ID NO 87
<211> LENGTH: 27
<212> TYPE: PRT
<213> ORGANISM: Artificial Sequence
<220> FEATURE:
<223> OTHER INFORMATION: Synthetic construct

<400> SEQUENCE: 87

Pro Ser Gln Gly Lys Gly Arg Gly Leu Ser Leu Ser Arg Phe Ser Trp
1               5                   10                  15

Gly Ala Leu Ile Leu Cys Leu Trp Ser Lys Phe
            20                  25

<210> SEQ ID NO 88
<211> LENGTH: 27
<212> TYPE: PRT
<213> ORGANISM: Artificial Sequence
<220> FEATURE:
<223> OTHER INFORMATION: Synthetic construct

<400> SEQUENCE: 88

Pro Ser Gln Gly Lys Gly Arg Gly Leu Ser Leu Ser Arg Phe Ser Trp
1               5                   10                  15

Gly Ala Ile Leu Cys Leu Trp Ser Lys Phe Cys
            20                  25

<210> SEQ ID NO 89
<211> LENGTH: 27
<212> TYPE: PRT
<213> ORGANISM: Artificial Sequence
<220> FEATURE:
<223> OTHER INFORMATION: Synthetic construct

<400> SEQUENCE: 89

Pro Ser Gln Gly Lys Gly Arg Gly Leu Ser Leu Ser Arg Phe Ser Trp
1               5                   10                  15

Gly Ala Leu Cys Leu Trp Ser Lys Phe Cys Arg
            20                  25

<210> SEQ ID NO 90
<211> LENGTH: 27
<212> TYPE: PRT
<213> ORGANISM: Artificial Sequence
<220> FEATURE:
<223> OTHER INFORMATION: Synthetic construct

<400> SEQUENCE: 90

Pro Ser Gln Gly Lys Gly Arg Gly Leu Ser Leu Ser Arg Phe Ser Trp
1               5                   10                  15

Gly Ala Cys Leu Trp Ser Lys Phe Cys Arg Trp
            20                  25

<210> SEQ ID NO 91
<211> LENGTH: 27
<212> TYPE: PRT
<213> ORGANISM: Artificial Sequence
<220> FEATURE:
<223> OTHER INFORMATION: Synthetic construct

<400> SEQUENCE: 91

Pro Ser Gln Gly Lys Gly Arg Gly Leu Ser Leu Ser Arg Phe Ser Trp
1               5                   10                  15

Gly Ala Leu Trp Ser Lys Phe Cys Arg Trp Phe
            20                  25

<210> SEQ ID NO 92
<211> LENGTH: 27
<212> TYPE: PRT
<213> ORGANISM: Artificial Sequence
<220> FEATURE:
<223> OTHER INFORMATION: Synthetic construct

<400> SEQUENCE: 92

Pro Ser Gln Gly Lys Gly Arg Gly Leu Ser Leu Ser Arg Phe Ser Trp
1               5                   10                  15

Gly Ala Trp Ser Lys Phe Cys Arg Trp Phe Gln
            20                  25

<210> SEQ ID NO 93
<211> LENGTH: 27
<212> TYPE: PRT
<213> ORGANISM: Artificial Sequence
<220> FEATURE:
<223> OTHER INFORMATION: Synthetic construct

<400> SEQUENCE: 93

Pro Ser Gln Gly Lys Gly Arg Gly Leu Ser Leu Ser Arg Phe Ser Trp
1               5                   10                  15

Gly Ala Ser Lys Phe Cys Arg Trp Phe Gln Arg
            20                  25

<210> SEQ ID NO 94
<211> LENGTH: 27
<212> TYPE: PRT
<213> ORGANISM: Artificial Sequence
<220> FEATURE:
<223> OTHER INFORMATION: Synthetic construct

<400> SEQUENCE: 94

Pro Ser Gln Gly Lys Gly Arg Gly Leu Ser Leu Ser Arg Phe Ser Trp
1               5                   10                  15

Gly Ala Glu Ser Pro Leu Leu Leu Ala Ala Lys
            20                  25

<210> SEQ ID NO 95
<211> LENGTH: 27
<212> TYPE: PRT
<213> ORGANISM: Artificial Sequence
<220> FEATURE:
<223> OTHER INFORMATION: Synthetic construct

<400> SEQUENCE: 95

Pro Ser Gln Gly Lys Gly Arg Gly Leu Ser Leu Ser Arg Phe Ser Trp
1               5                   10                  15

Gly Ala Gln Ala Leu Asn Lys Leu Leu Lys Tyr
            20                  25

<210> SEQ ID NO 96
<211> LENGTH: 27
<212> TYPE: PRT
<213> ORGANISM: Artificial Sequence
<220> FEATURE:
<223> OTHER INFORMATION: Synthetic construct

<400> SEQUENCE: 96

Pro Ser Gln Gly Lys Gly Arg Gly Leu Ser Leu Ser Arg Phe Ser Trp
1               5                   10                  15

Gly Ala Asn Leu Val Arg Ala Leu Leu Ala Arg
            20                  25

<210> SEQ ID NO 97
<211> LENGTH: 27
<212> TYPE: PRT
<213> ORGANISM: Artificial Sequence
<220> FEATURE:
<223> OTHER INFORMATION: Synthetic construct

<400> SEQUENCE: 97

Pro Ser Gln Gly Lys Gly Arg Gly Leu Ser Leu Ser Arg Phe Ser Trp
1               5                   10                  15

Gly Ala Leu Val Arg Ala Leu Leu Ala Arg Arg
            20                  25

<210> SEQ ID NO 98
<211> LENGTH: 27
<212> TYPE: PRT
<213> ORGANISM: Artificial Sequence
<220> FEATURE:
<223> OTHER INFORMATION: Synthetic construct

<400> SEQUENCE: 98

Pro Ser Gln Gly Lys Gly Arg Gly Leu Ser Leu Ser Arg Phe Ser Trp
1               5                   10                  15

Gly Ala Val Arg Ala Leu Leu Ala Arg Arg Ala
            20                  25

<210> SEQ ID NO 99
<211> LENGTH: 27
<212> TYPE: PRT
<213> ORGANISM: Artificial Sequence
<220> FEATURE:
<223> OTHER INFORMATION: Synthetic construct

<400> SEQUENCE: 99

Pro Ser Gln Gly Lys Gly Arg Gly Leu Ser Leu Ser Arg Phe Ser Trp
1               5                   10                  15

Gly Ala Arg Ala Leu Leu Ala Arg Arg Ala Ser
            20                  25

<210> SEQ ID NO 100
<211> LENGTH: 27
<212> TYPE: PRT
<213> ORGANISM: Artificial Sequence
<220> FEATURE:
<223> OTHER INFORMATION: Synthetic construct

<400> SEQUENCE: 100

Pro Ser Gln Gly Lys Gly Arg Gly Leu Ser Leu Ser Arg Phe Ser Trp

```
                1               5                   10                  15
Gly Ala Ala Leu Leu Ala Arg Arg Ala Ser Val
            20                  25

<210> SEQ ID NO 101
<211> LENGTH: 27
<212> TYPE: PRT
<213> ORGANISM: Artificial Sequence
<220> FEATURE:
<223> OTHER INFORMATION: Synthetic construct

<400> SEQUENCE: 101

Pro Ser Gln Gly Lys Gly Arg Gly Leu Ser Leu Ser Arg Phe Ser Trp
1               5                   10                  15

Gly Ala Leu Leu Ala Arg Arg Ala Ser Val Ser
            20                  25

<210> SEQ ID NO 102
<211> LENGTH: 27
<212> TYPE: PRT
<213> ORGANISM: Artificial Sequence
<220> FEATURE:
<223> OTHER INFORMATION: Synthetic construct

<400> SEQUENCE: 102

Pro Ser Gln Gly Lys Gly Arg Gly Leu Ser Leu Ser Arg Phe Ser Trp
1               5                   10                  15

Gly Ala Leu Ala Arg Arg Ala Ser Val Ser Ala
            20                  25

<210> SEQ ID NO 103
<211> LENGTH: 27
<212> TYPE: PRT
<213> ORGANISM: Artificial Sequence
<220> FEATURE:
<223> OTHER INFORMATION: Synthetic construct

<400> SEQUENCE: 103

Pro Ser Gln Gly Lys Gly Arg Gly Leu Ser Leu Ser Arg Phe Ser Trp
1               5                   10                  15

Gly Ala Ala Arg Arg Ala Ser Val Ser Ala Arg
            20                  25

<210> SEQ ID NO 104
<211> LENGTH: 27
<212> TYPE: PRT
<213> ORGANISM: Artificial Sequence
<220> FEATURE:
<223> OTHER INFORMATION: Synthetic construct

<400> SEQUENCE: 104

Pro Ser Gln Gly Lys Gly Arg Gly Leu Ser Leu Ser Arg Phe Ser Trp
1               5                   10                  15

Gly Ala Arg Arg Ala Ser Val Ser Ala Arg Ala
            20                  25

<210> SEQ ID NO 105
<211> LENGTH: 27
<212> TYPE: PRT
<213> ORGANISM: Artificial Sequence
<220> FEATURE:
<223> OTHER INFORMATION: Synthetic construct

<400> SEQUENCE: 105
```

Pro Ser Gln Gly Lys Gly Arg Gly Leu Ser Leu Ser Arg Phe Ser Trp
1               5                   10                  15

Gly Ala Arg Ala Ser Val Ser Ala Arg Ala Thr
            20                  25

<210> SEQ ID NO 106
<211> LENGTH: 27
<212> TYPE: PRT
<213> ORGANISM: Artificial Sequence
<220> FEATURE:
<223> OTHER INFORMATION: Synthetic construct

<400> SEQUENCE: 106

Pro Ser Gln Gly Lys Gly Arg Gly Leu Ser Leu Ser Arg Phe Ser Trp
1               5                   10                  15

Gly Ala Ala Ser Val Ser Ala Arg Ala Thr Gly
            20                  25

<210> SEQ ID NO 107
<211> LENGTH: 27
<212> TYPE: PRT
<213> ORGANISM: Artificial Sequence
<220> FEATURE:
<223> OTHER INFORMATION: Synthetic construct

<400> SEQUENCE: 107

Pro Ser Gln Gly Lys Gly Arg Gly Leu Ser Leu Ser Arg Phe Ser Trp
1               5                   10                  15

Gly Ala Ser Val Ser Ala Arg Ala Thr Gly Thr
            20                  25

<210> SEQ ID NO 108
<211> LENGTH: 27
<212> TYPE: PRT
<213> ORGANISM: Artificial Sequence
<220> FEATURE:
<223> OTHER INFORMATION: Synthetic construct

<400> SEQUENCE: 108

Pro Ser Gln Gly Lys Gly Arg Gly Leu Ser Leu Ser Arg Phe Ser Trp
1               5                   10                  15

Gly Ala Val Ser Ala Arg Ala Thr Gly Thr Ala
            20                  25

<210> SEQ ID NO 109
<211> LENGTH: 27
<212> TYPE: PRT
<213> ORGANISM: Artificial Sequence
<220> FEATURE:
<223> OTHER INFORMATION: Synthetic construct

<400> SEQUENCE: 109

Pro Ser Gln Gly Lys Gly Arg Gly Leu Ser Leu Ser Arg Phe Ser Trp
1               5                   10                  15

Gly Ala Ser Ala Arg Ala Thr Gly Thr Ala Phe
            20                  25

<210> SEQ ID NO 110
<211> LENGTH: 27
<212> TYPE: PRT
<213> ORGANISM: Artificial Sequence
<220> FEATURE:
<223> OTHER INFORMATION: Synthetic construct

<400> SEQUENCE: 110

Pro Ser Gln Gly Lys Gly Arg Gly Leu Ser Leu Ser Arg Phe Ser Trp
1               5                   10                  15

Gly Ala Ala Arg Ala Thr Gly Thr Ala Phe Arg
            20                  25

<210> SEQ ID NO 111
<211> LENGTH: 27
<212> TYPE: PRT
<213> ORGANISM: Artificial Sequence
<220> FEATURE:
<223> OTHER INFORMATION: Synthetic construct

<400> SEQUENCE: 111

Pro Ser Gln Gly Lys Gly Arg Gly Leu Ser Leu Ser Arg Phe Ser Trp
1               5                   10                  15

Gly Ala Leu Gln Pro Asn Lys Thr Phe Ala Cys
            20                  25

<210> SEQ ID NO 112
<211> LENGTH: 27
<212> TYPE: PRT
<213> ORGANISM: Artificial Sequence
<220> FEATURE:
<223> OTHER INFORMATION: Synthetic construct

<400> SEQUENCE: 112

Pro Ser Gln Gly Lys Gly Arg Gly Leu Ser Leu Ser Arg Phe Ser Trp
1               5                   10                  15

Gly Ala Tyr Asn Leu Leu Leu Ser Tyr Asp Arg
            20                  25

<210> SEQ ID NO 113
<211> LENGTH: 27
<212> TYPE: PRT
<213> ORGANISM: Artificial Sequence
<220> FEATURE:
<223> OTHER INFORMATION: Synthetic construct

<400> SEQUENCE: 113

Pro Ser Gln Gly Lys Gly Arg Gly Leu Ser Leu Ser Arg Phe Ser Trp
1               5                   10                  15

Gly Ala Lys Arg Lys His Thr Gln Trp Thr Tyr
            20                  25

<210> SEQ ID NO 114
<211> LENGTH: 27
<212> TYPE: PRT
<213> ORGANISM: Artificial Sequence
<220> FEATURE:
<223> OTHER INFORMATION: Synthetic construct

<400> SEQUENCE: 114

Pro Ser Gln Gly Lys Gly Arg Gly Leu Ser Leu Ser Arg Phe Ser Trp
1               5                   10                  15

Gly Ala Leu Leu Glu Leu Ile Ile Thr Thr Lys
            20                  25

<210> SEQ ID NO 115
<211> LENGTH: 27
<212> TYPE: PRT
<213> ORGANISM: Artificial Sequence
<220> FEATURE:
<223> OTHER INFORMATION: Synthetic construct

```
<400> SEQUENCE: 115

Pro Ser Gln Gly Lys Gly Arg Gly Leu Ser Leu Ser Arg Phe Ser Trp
1               5                   10                  15

Gly Ala Leu Val Ser Leu Lys Trp Lys Arg Tyr
            20                  25

<210> SEQ ID NO 116
<211> LENGTH: 27
<212> TYPE: PRT
<213> ORGANISM: Artificial Sequence
<220> FEATURE:
<223> OTHER INFORMATION: Synthetic construct

<400> SEQUENCE: 116

Pro Ser Gln Gly Lys Gly Arg Gly Leu Ser Leu Ser Arg Phe Ser Trp
1               5                   10                  15

Gly Ala Val Ser Leu Lys Trp Lys Arg Tyr Gly
            20                  25

<210> SEQ ID NO 117
<211> LENGTH: 27
<212> TYPE: PRT
<213> ORGANISM: Artificial Sequence
<220> FEATURE:
<223> OTHER INFORMATION: Synthetic construct

<400> SEQUENCE: 117

Pro Ser Gln Gly Lys Gly Arg Gly Leu Ser Leu Ser Arg Phe Ser Trp
1               5                   10                  15

Gly Ala Ser Leu Lys Trp Lys Arg Tyr Gly Arg
            20                  25

<210> SEQ ID NO 118
<211> LENGTH: 27
<212> TYPE: PRT
<213> ORGANISM: Artificial Sequence
<220> FEATURE:
<223> OTHER INFORMATION: Synthetic construct

<400> SEQUENCE: 118

Pro Ser Gln Gly Lys Gly Arg Gly Leu Ser Leu Ser Arg Phe Ser Trp
1               5                   10                  15

Gly Ala Leu Lys Trp Lys Arg Tyr Gly Arg Pro
            20                  25

<210> SEQ ID NO 119
<211> LENGTH: 27
<212> TYPE: PRT
<213> ORGANISM: Artificial Sequence
<220> FEATURE:
<223> OTHER INFORMATION: Synthetic construct

<400> SEQUENCE: 119

Pro Ser Gln Gly Lys Gly Arg Gly Leu Ser Leu Ser Arg Phe Ser Trp
1               5                   10                  15

Gly Ala Lys Trp Lys Arg Tyr Gly Arg Pro Tyr
            20                  25

<210> SEQ ID NO 120
<211> LENGTH: 27
<212> TYPE: PRT
<213> ORGANISM: Artificial Sequence
<220> FEATURE:
<223> OTHER INFORMATION: Synthetic construct
```

```
<400> SEQUENCE: 120

Pro Ser Gln Gly Lys Gly Arg Gly Leu Ser Leu Ser Arg Phe Ser Trp
1               5                   10                  15

Gly Ala Asn Thr Leu Leu Gln Gln Lys Leu Leu
            20                  25

<210> SEQ ID NO 121
<211> LENGTH: 27
<212> TYPE: PRT
<213> ORGANISM: Artificial Sequence
<220> FEATURE:
<223> OTHER INFORMATION: Synthetic construct

<400> SEQUENCE: 121

Pro Ser Gln Gly Lys Gly Arg Gly Leu Ser Leu Ser Arg Phe Ser Trp
1               5                   10                  15

Gly Ala Thr Ile Met Ile Gln Lys Met Ile Phe
            20                  25

<210> SEQ ID NO 122
<211> LENGTH: 27
<212> TYPE: PRT
<213> ORGANISM: Artificial Sequence
<220> FEATURE:
<223> OTHER INFORMATION: Synthetic construct

<400> SEQUENCE: 122

Pro Ser Gln Gly Lys Gly Arg Gly Leu Ser Leu Ser Arg Phe Ser Trp
1               5                   10                  15

Gly Ala Lys Leu Pro Arg Cys Leu Trp Pro Arg
            20                  25

<210> SEQ ID NO 123
<211> LENGTH: 27
<212> TYPE: PRT
<213> ORGANISM: Artificial Sequence
<220> FEATURE:
<223> OTHER INFORMATION: Synthetic construct

<400> SEQUENCE: 123

Pro Ser Gln Gly Lys Gly Arg Gly Leu Ser Leu Ser Arg Phe Ser Trp
1               5                   10                  15

Gly Ala Leu Gly Asp Arg Trp Phe Leu Arg Val
            20                  25

<210> SEQ ID NO 124
<211> LENGTH: 27
<212> TYPE: PRT
<213> ORGANISM: Artificial Sequence
<220> FEATURE:
<223> OTHER INFORMATION: Synthetic construct

<400> SEQUENCE: 124

Pro Ser Gln Gly Lys Gly Arg Gly Leu Ser Leu Ser Arg Phe Ser Trp
1               5                   10                  15

Gly Ala Arg Tyr Ala Gln Ala Phe His Thr Arg
            20                  25

<210> SEQ ID NO 125
<211> LENGTH: 41
<212> TYPE: PRT
<213> ORGANISM: Artificial Sequence
<220> FEATURE:
```

```
<223> OTHER INFORMATION: Synthetic construct

<400> SEQUENCE: 125

Pro Ser Gln Gly Lys Gly Arg Gly Leu Ser Leu Ser Arg Phe Ser Trp
1               5                   10                  15

Gly Ala Pro Ser Gln Ala Ser Ser Gly Gln Ala Arg Met Phe Pro Asn
            20                  25                  30

Ala Pro Tyr Leu Pro Ser Cys Leu Glu
        35                  40

<210> SEQ ID NO 126
<211> LENGTH: 18
<212> TYPE: PRT
<213> ORGANISM: Homo sapiens

<400> SEQUENCE: 126

Asn Ala Gly Asp Arg Ser Thr Asp Tyr Gly Ile Phe Gln Ile Asn Ser
1               5                   10                  15

Arg Tyr

<210> SEQ ID NO 127
<211> LENGTH: 19
<212> TYPE: PRT
<213> ORGANISM: Homo sapiens

<400> SEQUENCE: 127

Pro Pro Ser Gln Gly Lys Gly Ala Glu Gly Gln Arg Pro Gly Phe Gly
1               5                   10                  15

Tyr Gly Gly
```

POLYPEPTIDES WITH AFFINITY FOR HEAT SHOCK PROTEINS (HSPS) AND HSP ASSOCIATED COMPLEXES (HACS) AND THEIR USE IN DIAGNOSIS AND THERAPY

RELATED APPLICATIONS

This application is a national phase application under 35 U.S.C. §371 of International Application No. PCT/CA2012/050175, filed Mar. 21, 2012, which claims priority to U.S. Provisional Application No. 61/454,718, filed Mar. 21, 2011. The entire text of each of the above referenced disclosures is specifically incorporated herein by reference.

FIELD

The present application is related to novel peptides and polypeptides and their use for example in protocols for affinity enrichment of substances with diagnostic and prognostic significance to pathological conditions, as well as for their inclusion in therapeutic strategies.

BACKGROUND

Heat Shock Proteins (HSPs)

The hydrophobic regions of proteins are generally secluded, internal features in an aqueous environment. However, due to the high protein concentration within cells as well as fluctuations in charged molecules and physical parameters ("cellular stress"), the risk of exposure of hydrophobic regions is probably constant between synthesis, transport and function (Frydman J. 2001; Yam et al. 2005). Aside from compromised function, exposed hydrophobic regions cause protein aggregation, membrane damage and apoptosis.

Heat shock proteins (HSPs), also known as chaperones, bind to exposed hydrophobic regions to minimize such damage. HSPs are broadly conserved throughout the spectrum of life, frequently exhibiting 70% homology or greater in amino acid sequence between bacterial and human representatives (Bukau and Horwich 1998; Daugaard et al. 2007). In bacteria there is generally a single gene for HSP60, HSP70 and HSP90. Expression may be increased during conditions that unfold proteins such as fluctuations in temperature and ion concentration.

In higher eukaryotic organisms such as mammals, there are distinct isoforms of HSPs that have restricted subcellular location. For HSP70, there are isoforms for general activity in the cytoplasm (HSP70-8), endoplasmic reticulum (HSP70-5; grp78 or BiP) and mitochondrion (HSP70-9; mortalin). However, during potential cellular crisis periods such as anoxia, nutrient limitation, or ionic imbalance, the unfolding of proteins induces the expression of additional isoforms such as HSP70-1 (Scriven et al. 2007; Qian et al. 2006).

Broadly, HSP isoforms may be referred to as un-inducible (constitutive expression) or inducible (expression stimulated by cellular stress). The probability of HSP binding to appropriate polypeptide ligands inside the cell is influenced by ATP hydrolysis. The repeated loading of ATP, and release of ADP, cause allosteric changes in HSPs; these changes in conformation determine accessibility of the peptide binding domain to candidate "clients". The binding and release of distorted proteins by HSPs may permit the clients to refold and continue function as cellular equilibrium is restored.

Some HSP family members (such as HSP90) also participate as facilitators, supporting the conformation of receptors and kinases for greater efficiency in their signaling activity or post-translational modification of other molecules (e.g. Bron et at. 2008). Alternatively, where protein distortion or fragmentation is beyond recovery, HSP family members participate in directing irreparably damaged proteins for further reduction into peptides (Young et al. 2004; Bukau et al. 2006). These peptides may ultimately end up on the surface of cells in association with molecules of the major histocompatibility complex (MHC) for inspection by cells of the immune system (Ishii et al. 1999; Binder et al. 2001).

However, even when released due to necrosis or other cellular trauma, HSPs retain their capability to stimulate immune responses to bound peptides and proteins even in the negligible presence of extracellular ATP/ADP (Henderson et al 2010a; Henderson et al 2010b; Suto and Srivastava 1995; Castellino et al 2000; Basu et at. 2001; Tobian et al 2004; Chen and Cao 2010)

HSP Directed Immunotherapy

The ability to harness the immunomodulatory capacity of HSPs is highly desirable (Binder 2008; Karapanagiotou et al 2009). Experimental evidence for artificial stimulation of the various immune responses is unequivocal, either when HSP complexes are enriched from diseased tissue or are prepared by genetic or chemical synthesis. However, the extrapolation of these observations to consistent clinically relevant results (i.e. reduced morbidity and recurrence free survival) remain elusive (Moroi et al. 2000; Vanaja et al. 2000).

The reason for the shortfall in expectations of HSP directed immunotherapy may include the possibility that contemporary protocols do not provide sufficient antigenic information to account for genetic variability within the population at risk (Davila et al. 2010; Jacobson 2004). Furthermore there will be different affinities of different proteins and peptides for different HSPs—only a small fraction of peptides may bind efficiently and these may out compete or exclude those necessary for a robust immune response (Flechtner et al. 2006).

To date, in vitro methods permit preparation of HSP70 (Bolhassani et al. 2008; Nishikawa et al., 2008) complexes with single peptides, chemically cross-linked or expressed in tandem with recombinant HSP70. Individually such preparations may not reflect natural conformations desirable for successful engagement of relevant receptors (Becker et al. 2002; Binder R J 2009). The recombinant approach may also be prohibitively expensive in the provision of comprehensive antigen coverage.

Stability and longevity may also be a limiting factor to clinical success of contemporary HSP immunotherapy methods; following vaccination, HSP-conjugates may not be sufficiently robust to establish contact with antigen presenting cells (APCs) due to susceptibility to serum peptidases (Micheilin et al. 2005).

Availability of vaccine material is an additional factor governing success of HSP immunotherapy: restricted sources of antigenic material may preclude a strong primary, sustained or anamnestic immune response. Inadequate amounts of starting material may be the most important limitation for HSP based immunotherapy. Restricted availability of HSP based immunotherapeutic material may be due to economically prohibitive number of required epitopes to provide individual or population wide coverage. Further, some important antigens may be difficult to produce in the laboratory. Such antigens include membrane proteins or those that require post translational translation (e.g. glycosylation: the addition of carbohydrate groups). Contemporary methodologies may also prone to reductive losses during the sequences of fractionation and preparation (e.g. during ADP chromatography). Where a patient's own tumor material is used as the source of HSP conjugate, obvious limitations exist predicated by the amount of starting source material. For example, a recent phase III trial incorporating HSP complexes enriched from individual patient tumors yielded largely unremarkable results. However, the study indicated that patients receiving repeated doses (predicated by larger tumors) had better parameters of immune response and median survival (Binder 2008). This important observation indicates that availability of material for sustained vaccination will be a factor in determining the success of HSP-based immunotherapy. This issue has been addressed by Katsanis, Graner and colleagues in which whole cancer cell lysates have been fractionated to produce chaperone rich lysates using free solution isoelectric focusing (FS-IEF) (Kislin et al. 2007; Bleifuss et al. 2008).

HSPs in Cancer Cells

HSPs are both cytoprotectants and powerful modulators of the immune system (Henderson et al. 2010c). However, as cytoprotectants, HSP expression is considerably over-extended in cancer cells where their function has been exploited to an extraordinary degree (Jäättelä 1995; Cappello et al 2003; Daugaard et al 2005; Rohde et al 2005; Sherman and Multhoff 2007). During oncogenesis, for example, overexpression of HSPs such as HSP90 provides structural support for constitutively active proteins that drive unregulated cell multiplication (Lewis et al. 2000; Broemer et al. 2004) Up-regulated HSPs may also promote survival and stall apoptosis within an otherwise prohibitively hostile environment characterized by anoxia and low nutrient availability (Powers et al 2009).

Over-expression of HSPs, as is typical of cancer, may also cause confusion and subversion of immune effectors directed against out of context expression of proteins permitting uninhibited cell division or survival in hostile environments (Chalmin et al. 2010; Su et al. 2010; Coelho et al. 2008). Due to the support and stabilisation necessary for continued function of membrane proteins, unlike normal cells, HSPs are found on the external surface of cancer cells (Graner et al. 2009; Cappello et al. 2008). (Horváth et al 2008). Consequently vesicular material released by cancer cells are also richly accessorised by HSPs (Broquet et al 2003; Lancaster and Febbraio 2005; Evdonin et al 2006; Mambula and Calderwood 2006).

Cumulatively, the above functions render cancer cells to become addicted to HSP over-expression: Without such increases, many cancer proteins would unravel and be directed toward degradation. Such losses would deny the cancer cell of important survival factors causing apoptosis and cell lysis. Indeed, many cancer therapies currently in development are depending upon the efficacy of HSP inhibitors (Banerji 2009; Powers et al. 2007; Powers et al. 2010; Davenport et al. 2010).

The use of cell derived vesicles (CDVs), such as exosomes for detecting biomarkers for diagnostic, therapy-related or prognostic methods to identify phenotypes is described in WO 2010/056337, the contents of which are specifically incorporated herein by reference.

SUMMARY OF THE APPLICATION

In the present application, novel polypeptide reagents are provided as well as protocols that serve to simplify the collection of HSP associated complexes (HACs) and cell derived vesicles (CDVs) from both in vitro and in vivo sources in a timely manner with limited manipulation and in a format that facilitates the processing of a large volume of samples or adaptation to automation. Because CDVs are anticipated to become the fastest growing area of research and translational medicine due to their role as transfer agents, availability of such reagents and protocols is anticipated to be highly useful, for example, in any area where repetitive and non-injurious collection and analysis of biological fluid is desired.

The present application includes an isolated peptide consisting of 8 to 50 amino acids and comprising an α-helix forming-amino acid sequence that binds a heat shock protein, the α-helix-forming amino acid sequence selected from:

(i) a sequence comprising at least 8 to 12 contiguous amino acids of $X^1$-$X^2$-$X^3$-$X^4$-$X^5$-$X^6$-$X^7$-$X^8$-$X^9$-$X^{10}$-$X^{11}$-$X^{12}$ [SEQ ID NO:1], wherein
$X^1$ is G, A, D, or E;
$X^2$ is R, H or K;
$X^3$ is G, A, S or T;
$X^4$ is R, H, K, N or Q;
$X^5$ is G, A, S or T;
$X^6$ is A, V, I, L, M, F or W;
$X^7$ is G, A, S or T;
$X^8$ is A, V, I, L or G;
$X^9$ is S, T, M, A, V, I or L;
$X^{10}$ is R, H, K, N or Q;
$X^{11}$ is A, V, I, L M, F or W; and
$X^{12}$, is D, E, S, or T; and ii) a functionally equivalent peptide to the sequences of (i).

In yet another embodiment, the isolated peptide is selected from:

| | | |
|---|---|---|
| (i) | PSQGKGRGLSLSRFSWGA; | [SEQ ID NO 2:] |
| (ii) | PSQGKGRG; | [SEQ ID NO: 3] |
| (iii) | GRGLSLSRF; | [SEQ ID NO: 4] |
| (iv) and | SLSRFSWGA; | [SEQ ID NO: 5] |
| (v) | GWGDRGNGFGLMQVDKRY; | [SEQ ID NO: 6] | and ii) functionally equivalent peptides to the sequences of (i)-(v).

In yet another embodiment, the isolated peptide is selected from:

| | | |
|---|---|---|
| (i) and | PSQGKGRGLSLSRFSWGA; | [SEQ ID NO 2:] |
| (v) | GWGDRGNGFGLMQVDKRY. | [SEQ ID NO: 6] |

In an embodiment of the application the isolated peptides further comprise at least one second peptide portion comprising an antigenic amino acid sequence and/or an α-helix stabilizing amino acid sequence.

Accordingly, in another embodiment, the present application includes novel polypeptides that comprise a first peptide portion and at least one second peptide portion. The first peptide portion comprises a sequence that, on its own, has an affinity for heat shock proteins, specifically for corynebacterial HSPs, for example HSP70 from *Mycobacterium* or *Arthrobacterium* species. This first peptide portion has a central α-helix made up of hydrophobic, uncharged polar and basic amino acids. In an embodiment, the first peptide portion is an isolated peptide as defined above. At least one flanking peptide portion serves to stabilize the α-helix in the first peptide portion and/or increases the affinity of the entire polypeptide for peptide binding domains on target proteins.

Modulating behaviour of alpha helices is known in the art (e.g. Drahl 2008; Patgiri et al 2008). However in the current application following synthesis, no further chemical modification is required to facilitate binding. In an embodiment, the at least one second peptide portion alters the binding behavior of the first peptide portion so that it binds to HSPs from many sources.

The present application therefore includes a polypeptide comprising (a) a first peptide portion that comprises an α-helix-forming amino acid sequence that binds a heat shock protein; and (b) at least one second peptide portion comprising an antigenic amino acid sequence and/or an α-helix-stabilizing amino acid sequence that increases the interaction of the first peptide portion with the heat shock protein.

In an embodiment, the first peptide portion of the polypeptide of the application is a peptide consisting of 8 to 50 amino acids and comprising an α-helix forming-amino acid sequence that binds a heat shock protein, the α-helix-forming amino acid sequence selected from:

i) a sequence comprising at least 8 to 12 contiguous amino acids of $X^1$-$X^2$-$X^3$-$X^4$-$X^5$-$X^6$-$X^7$-$X^8$-$X^9$-$X^{10}$-$X^{11}$-$X^{12}$ [SEQ ID NO: 1], wherein
$X^1$ is G, A, D, or E;
$X^2$ is R, H or K;
$X^3$ is G, A, S or T;
$X^4$ is R, H, K, N or Q;
$X^5$ is G, A, S or T;
$X^6$ is A, V, I, L, M, F or W;
$X^7$ is G, A, S or T;
$X^8$ is A, V, I, L or G;
$X^9$ is S, T, M, A, V, I or L;
$X^{10}$ is R, H, K, N or Q;
$X^{11}$ is A, V, I, L M, F or W; and
$X^{12}$ is D, E, S, or T; and
ii) functionally equivalent peptides of the sequences of (i).

In yet another embodiment, the first peptide portion is selected from:

(i) PSQGKGRGLSLSRFSWGA; [SEQ ID NO 2:]
(ii) PSQGKGRG; [SEQ ID NO: 3]
(iii) GRGLSLSRF; [SEQ ID NO: 4]
(iv) SLSRFSWGA; [SEQ ID NO: 5]
and
(v) GWGDRGNGFGLMQVDKRY; [SEQ ID NO: 6]

and
ii) functionally equivalent peptides to the sequences of (i)-(v).

In yet another embodiment, the first peptide portion is selected from:

(i) PSQGKGRGLSLSRFSWGA; [SEQ ID NO 2:]
and
(v) GWGDRGNGFGLMQVDKRY. [SEQ ID NO: 6]

In an embodiment of the application, the at least one second peptide portion comprises clinically or physiologically relevant amino acid sequences, such as immunomodulatory epitopes of cancer proteins that are compatible with being adsorbed and re-presented in association with MHC complexes. Accordingly, in one embodiment, the at least one second peptide portion comprises an amino acid sequence that has previously been shown to prompt or augment an immune response, for example to pathologic events such as cancer, infectious disease, developmental or spontaneous conditions. In another embodiment, the at least one second peptide portion comprises an immunostimulatory epitope from a tumor associated antigen, such as survivin, mucin-1, transient receptor potential cation channel subfamily V, member 6 (TRPV6) or Wilms tumor protein-1 (WT1).

In another embodiment, the at least one second peptide portion comprises one or more of:

STFKNWPFL, [SEQ ID NO: 7]

LTLGEFLKL; [SEQ ID NO: 8]

LRRKCAVPS; [SEQ ID NO: 9]

GVTSAPDTR; [SEQ ID NO: 10]

MFLQIYKQG; [SEQ ID NO: 11]

FLQIYKQGG; [SEQ ID NO: 12]

LQIYKQGGF; [SEQ ID NO: 13]

QIYKQGGFL; [SEQ ID NO: 14]

IYKQGGFLG; [SEQ ID NO: 15]

YKQGGFLGL; [SEQ ID NO: 16]

VVQLTLAFR; [SEQ ID NO: 17]

FNQYKTEAA; [SEQ ID NO: 18]

NQYKTEAAS; [SEQ ID NO: 19]

QYKTEAASR; [SEQ ID NO: 20]

YKTEAASRY; [SEQ ID NO: 21]

GQLDIFPAR; [SEQ ID NO: 22]

KGLILCLWS; [SEQ ID NO: 23]

GLILCLWSK; [SEQ ID NO: 24]

LILCLWSKF; [SEQ ID NO: 25]

ILCLWSKFC; [SEQ ID NO: 26]

LCLWSKFCR; [SEQ ID NO: 27]

CLWSKFCRW; [SEQ ID NO: 28]

LWSKFCRWF; [SEQ ID NO: 29]

WSKFCRWFQ; [SEQ ID NO: 30]

SKFCRWFQR; [SEQ ID NO: 31]

ESPLLLAAK; [SEQ ID NO: 32]

QALNKLLKY; [SEQ ID NO: 33]

NLVRALLAR; [SEQ ID NO: 34]

LVRALLARR; [SEQ ID NO: 35]

VRALLARRA; [SEQ ID NO: 36]

RALLARRAS; [SEQ ID NO: 37]

ALLARRASV; [SEQ ID NO: 38]

LLARRASVS; [SEQ ID NO: 39]

LARRASVSA; [SEQ ID NO: 40]

ARRASVSAR; [SEQ ID NO: 41]

RRASVSARA; [SEQ ID NO: 42]

RASVSARAT; [SEQ ID NO: 43]

ASVSARATG; [SEQ ID NO: 44]

SVSARATGT; [SEQ ID NO: 45]

VSARATGTA; [SEQ ID NO: 46]

SARATGTAF; [SEQ ID NO: 47]

ARATGTAFR; [SEQ ID NO: 48]

LQPNKTFAC; [SEQ ID NO: 49]

YNLLLSYDR; [SEQ ID NO: 50]

KRKHTQWTY; [SEQ ID NO: 51]

LLELIITTK; [SEQ ID NO: 52]

LVSLKWKRY; [SEQ ID NO: 53]

VSLKWKRYG; [SEQ ID NO: 54]

SLKWKRYGR; [SEQ ID NO: 55]

LKWKRYGRP; [SEQ ID NO: 56]

KWKRYGRPY; [SEQ ID NO: 57]

NTLLQQKLL; [SEQ ID NO: 58]

TIMIQKMIF; [SEQ ID NO: 59]

KLPRCLWPR; [SEQ ID NO: 60]

LGDRWFLRV; [SEQ ID NO: 61]

RYAQAFHTR; [SEQ ID NO: 62]
or

PSQASSGQARMFPNAPYLPSCLE, [SEQ ID No: 63]
or functionally equivalent sequences of
[SEQ ID NOs 7-62].

In another embodiment of the application, the first and at least one second peptide portions are joined by a linker moiety. In an embodiment of the application the linker moiety is a peptide comprising from 1 to 15, 2 to 10 or 3 to 5 amino acids. In another embodiment, the first and second peptide portions are joined by a covalent bond. In an embodiment the linker moiety comprises glycine and/or serine amino acids. In a further embodiment, the linker moiety comprises sites that are cleaved by enzymes in vivo.

In yet another embodiment of the application, the first peptide portion is at the N-terminus of the polypeptide and comprises one second peptide portion at the C-terminus. In another embodiment, the first peptide portion of the polypeptide is located centrally between two second peptide portions, which may be the same or different.

In yet another embodiment the polypeptides of the present application comprise, consist essentially of or consists of any combination of the first petide portions ([SEQ ID NOs: 1-6]) and second peptide portions ([SEQ ID NOs: 7-63]) listed above.

In yet another embodiment the polypeptides of the present application comprise, consist essentially of or consists of an amino acid sequence selected from:

PSQGKGRGLSLSRFSWGASTFKNWPFL; [SEQ ID NO: 64]

PSQGKGRGLSLSRFSWGALTLGEFLKL; [SEQ ID NO: 65]
and

PSQGKGRGLSLSRFSWGALRRKCAVPS [SEQ ID NO: 66]

PSQGKGRGLSLSRFSWGAPSQASSGQARMFPNAPYLPSCLE [SEQ ID NO: 67]

PSQGKGRGSTFKNWPFL; [SEQ ID NO: 68]

GRGLSLSRFSTFKNWPFL; [SEQ ID NO: 69]

SLSRFSWGALRRKCAVPS; [SEQ ID NO: 70]

SLSRFSWGALTLGEFLKL; [SEQ ID NO: 71]

PSQGKGRGLSLSRFSWGAGVTSAPDTR; [SEQ ID NO: 72]

PSQGKGRGLSLSRFSWGAMFLQIYKQG; [SEQ ID NO: 73]

PSQGKGRGLSLSRFSWGAFLQIYKQGG; [SEQ ID NO: 74]

PSQGKGRGLSLSRFSWGALQIYKQGGF; [SEQ ID NO: 75]

PSQGKGRGLSLSRFSWGAQIYKQGGFL; [SEQ ID NO: 76]

PSQGKGRGLSLSRFSWGAIYKQGGFLG; [SEQ ID NO: 77]

PSQGKGRGLSLSRFSWGAYKQGGFLGL; [SEQ ID NO: 78]

PSQGKGRGLSLSRFSWGAWQLTLAFR; [SEQ ID NO: 79]

PSQGKGRGLSLSRFSWGAFNQYKTEAA; [SEQ ID NO: 80]

PSQGKGRGLSLSRFSWGANQYKTEAAS; [SEQ ID NO: 81]

PSQGKGRGLSLSRFSWGAQYKTEAASR; [SEQ ID NO: 82]

PSQGKGRGLSLSRFSWGAYKTEAASRY; [SEQ ID NO: 83]

PSQGKGRGLSLSRFSWGAGQLDIFPAR; [SEQ ID NO: 84]

PSQGKGRGLSLSRFSWGAKGLILCLWS; [SEQ ID NO: 85]

PSQGKGRGLSLSRFSWGAGLILCLWSK; [SEQ ID NO: 86]

PSQGKGRGLSLSRFSWGALILCLWSKF; [SEQ ID NO: 87]

PSQGKGRGLSLSRFSWGAILCLWSKFC; [SEQ ID NO: 88]

PSQGKGRGLSLSRFSWGALCLWSKFCR; [SEQ ID NO: 89]

PSQGKGRGLSLSRFSWGACLWSKFCRW; [SEQ ID NO: 90]

PSQGKGRGLSLSRFSWGALWSKFCRWF; [SEQ ID NO: 91]

PSQGKGRGLSLSRFSWGAWSKFCRWFQ; [SEQ ID NO: 92]

PSQGKGRGLSLSRFSWGASKFCRWFQR; [SEQ ID NO: 93]

PSQGKGRGLSLSRFSWGAESPLLLAAK; [SEQ ID NO: 94]

PSQGKGRGLSLSRFSWGAQALNKLLKY; [SEQ ID NO: 95]

PSQGKGRGLSLSRFSWGANLVRALLAR; [SEQ ID NO: 96]

PSQGKGRGLSLSRFSWGALVRALLARR; [SEQ ID NO: 97]

PSQGKGRGLSLSRFSWGAVRALLARRA; [SEQ ID NO: 98]

PSQGKGRGLSLSRFSWGARALLARRAS; [SEQ ID NO: 99]

PSQGKGRGLSLSRFSWGAALLARRASV; [SEQ ID NO: 100]

PSQGKGRGLSLSRFSWGALLARRASVS; [SEQ ID NO: 101]

PSQGKGRGLSLSRFSWGALARRASVSA; [SEQ ID NO: 102]

PSQGKGRGLSLSRFSWGAARRASVSAR; [SEQ ID NO: 103]

PSQGKGRGLSLSRFSWGARRASVSARA; [SEQ ID NO: 104]

PSQGKGRGLSLSRFSWGARASVSARAT; [SEQ ID NO: 105]

PSQGKGRGLSLSRFSWGAASVSARATG; [SEQ ID NO: 106]

PSQGKGRGLSLSRFSWGASVSARATGT; [SEQ ID NO: 107]

PSQGKGRGLSLSRFSWGAVSARATGTA; [SEQ ID NO: 108]

PSQGKGRGLSLSRFSWGASARATGTAF; [SEQ ID NO: 109]

PSQGKGRGLSLSRFSWGAARATGTAFR; [SEQ ID NO: 110]

PSQGKGRGLSLSRFSVVGALQPNKTFAC; [SEQ ID NO: 111]

PSQGKGRGLSLSRFSWGAYNLLLSYDR; [SEQ ID NO: 112]

PSQGKGRGLSLSRFSWGAKRKHTQWTY; [SEQ ID NO: 113]

PSQGKGRGLSLSRFSWGALLELIITTK; [SEQ ID NO: 114]

PSQGKGRGLSLSRFSWGALVSLKWKRY; [SEQ ID NO: 115]

PSQGKGRGLSLSRFSWGAVSLKWKRYG; [SEQ ID NO: 116]

PSQGKGRGLSLSRFSWGASLKWKRYGR; [SEQ ID NO: 117]

PSQGKGRGLSLSRFSWGALKWKRYGRP; [SEQ ID NO: 118]

PSQGKGRGLSLSRFSWGAKWKRYGRPY; [SEQ ID NO: 119]

PSQGKGRGLSLSRFSWGANTLLQQKLL; [SEQ ID NO: 120]

PSQGKGRGLSLSRFSWGATIMIQKMIF; [SEQ ID NO: 121]

-continued

PSQGKGRGLSLSRFSWGAKLPRCLWPR;  [SEQ ID NO: 122]

PSQGKGRGLSLSRFSWGALGDRWFLRV;  [SEQ ID NO: 123]

PSQGKGRGLSLSRFSWGARYAQAFHTR;  [SEQ ID NO: 124]
and

PSQGKGRGLSLSRFSWGAPSQASSGQARMFPNAPYLPSCLE,  [SEQ ID No: 125]
and functionally equivalent sequences of
[SEQ ID NOs 64-125].

In yet another embodiment, the polypeptides of the present application are linked to a solid support. Solid supports may include but are not restricted to microscopic beads (e.g. magnetic or chemically activated) or any materials used for the preparation of microarrays, microfluidic devices or titre plate based high volume analysis.

It is another embodiment of the application that the isolated peptides and polypeptides of the application, further comprise a secondary modification and/or label selected from phosphorylation, acylation, acetylation, formylation, glycosylation, amidation, incorporation of chromophores, fluorescent dyes/fluorogenic groups, PEGylation, biotinylation and sulfation. For example, the secondary structure or label comprises biotin.

The peptides and polypeptides of the present application are useful for diagnostic and therapeutic applications. Accordingly, the present application also includes compositions comprising one or more of peptides and/or polypeptides of the present application and one or more additives, excipients and/or adjuvants. In one embodiment, the one or more additives comprises a detergent matrix, such as a detergent matrix that may be used for directly mixing with fractions of laboratory grown cells or biological fluids previously collected from plant, animal, patient and/or environmental samples. The detergents minimize non-specific co-enrichment of cellular materials that may occlude or dilute the affinity enriched molecules of interest.

Due to the immunomodulatory influence of HSPs, one aspect of the current application is to facilitate the use of HSP-directed immunotherapy in a more flexible, accessible manner, providing a sufficient supply of HSP-conjugated antigen(s) to accommodate sequential vaccinations and to prevent immunological escape of an infectious agent or cancer. Modification of epitopes by tandem linear synthesis with heat shock binding peptides increases their immunogenicity (Ciupitu et al. 1998; Flechtner et al. 2006; Moroi et al. 2000). The peptide approach in this application represents a flexible universal approach in which flanking peptides of the core sequence may be co-linearly synthesised with the bMBP core sequence according to MHC specificity or other biological prerequisite or desired outcome (Stocki et al. 2010).

Another aspect of the present application is that, due to high affinity binding of the peptides and polypeptides disclosed herein for HSPs, molecules interacting with HSPs will also be enriched using standard methods. The ability to capture proteins dependent upon HSPs using the peptides and polypeptides of the present application permits the identification of discrete features of disease-associated cells (such as cancer cells) that are informative in staging, prognosis and sensitivity to treatment.

Analyses involving cultured metastatic breast and prostate cancer cells confirmed the capability of the peptides and polypeptides of the present application to bind and facilitate the sedimentation of vesicular material from extracellular medium (for example, platelet free plasma) as determined by the immuno-detection of HSPs and glycolytic enzymes. Moreover, analysis of the peptide sedimented vesicular material determined that mRNA of multiple proteins over-expressed in cancer were preserved intact within the vesicular material. The range of possibilities for peptide and polypeptide utilization in cancer biology thus includes the capture of proteins and RNA species protected in extracellular material, with the potential for analysis by down-stream clinical methods such ELISA, Western blotting, mass spectrometry and qRT-PCR.

Therefore, the present application also includes a method of fractionating one or more substances relevant for discovery, research or clinical analysis from a biological sample comprising: (a) contacting the biological sample with one or more of the peptides and/or polypeptides of the present application under conditions suitable for binding of the one or more polypeptides to the one or more substances to form complexes, and (b) fractionating the complexes.

Cell derived vesicles (CDVs) are normally used as vehicles for intercellular communication without the necessity for direct contact. However, excessive vesicle release into the surrounding environment is a common feature of tumor cells. Capture of CDVs from the extracellular matrix is regarded as an important source of potential biomarkers, since proteins secreted by cancer cells may reflect the closest facsimile of biological interface between the cancer and the surrounding host tissue environment of the patient. Capture of vesicles from plasma and other body fluids is also regarded as highly significant in that the encapsulated material represents a source of biologic materials otherwise inaccessible by contemporary methods. Molecules associated with vesicles may thus permit informed decisions regarding the earlier staging of cancer patients, treatment, monitoring and recurrence free survival. Peptide capture of vesicular material may thus facilitate clinical analysis by microarray and qRT-PCR. Therefore the present application also includes a method of diagnosing or determining prognosis of a cancer in a subject comprising: (a) contacting a sample from the subject with one or more peptides and/or polypeptides of the present application under conditions suitable for the binding of the of the one or more polypeptides to one or more cancer relevant substances to form complexes, (b) fractionating the complexes, and (c) detecting the presence of the one or more cancer relevant substances in the complexes, wherein the presence of the one or more cancer relevant substances is indicative of the diagnosis or prognosis of the cancer.

In HSP augmented immunotherapy, previous attempts have resulted in increased immune cell activity in vitro, but have failed to translate into recurrence free survival. Administration of the peptides and/or polypeptides of the application may circumvent earlier shortcomings caused by availability of vaccine material or poor epitope coverage enabling immune escape. Peptides and polypeptides of the present application can be synthesised to include single or multiple disease epitopes.

Furthermore, because the biological potential of peptides is limited due to their proteolytic instability, stabilizations by flanking peptides in association with an alpha helix may provide resistance against degradation in contrast to naked beta sheet structure (Tyndall et al 2005). Also, the peptides and polypeptides of the present application are highly basic.

This property is likely to enhance cellular uptake and transport through the cell membrane unlike non-cationic peptides (Rezai et al 2006).

The properties of the peptides and polypeptides mentioned above may explain that when included in the extracellular medium of the cancer cell lines such as PC3 (prostate cancer) and MCF7 (breast cancer), one of the polypeptides, [SEQ ID NO 66], caused drastic inhibition of protein synthesis and cell lysis at concentrations 7-25 µg/mL within 24 hours of administration (see relevant example). This observation suggests that the peptides and/or polypeptides of the present application may include molecules that either inhibit the support function for oncoproteins provided by HSPs and/or activate apoptosis pathways. The alpha helix and flanking sequences may permit the peptides of the application to resist the protease rich medium of cancer cells, a trait shared by human tissue fluids (e.g. serum). Administration of the peptides and/or polypeptides may therefore have resulted in degradation of oncoproteins and reduced signaling capability imperative for cancer survival. Since all major cancer causing species rely upon scaffolding by HSPs for stability and function, the peptides may represent a source of direct therapeutic application.

The present application further includes a method of treating cancer and other diseases comprising administering an effective amount of one or more of the peptides and/or polypetides of the present application to a subject in need thereof.

In another aspect of the present application, there is included a complex comprising a peptide or the polypeptide of the application and a heat shock protein, wherein the peptide or polypeptide and heat shock protein (HSP) are affinity associated. In an embodiment, the complex the heat shock protein is selected from HSP60, HSP70, HSP90 or HSP27 or an isoform thereof. In a further embodiment, the HSP is on a CDV and a complex is formed between the peptide or polypeptide of the application and the CDV.

A further aspect of the present application includes an agent comprising a peptide, polypeptide or a complex described herein and a bead which functions to link the polypeptide and/or peptide portions together.

In an embodiment, the peptide portions a) and b) are conjugated to the bead.

Any bead can be used including for example Dynal beads.

A further aspect includes an agent comprising a nucleic acid encoding a peptide or polypeptide described herein.

In an embodiment, the agent comprises a nucleic acid encoding the peptide portion a); and a nucleic acid encoding the peptide portion b).

The peptide, polypeptide, complex and/or agent can be in a composition with one or more additives, excipients and/or adjuvants.

A further aspect includes a method of fractionating one or more substances relevant for discovery, research or clinical analysis from a biological sample comprising: (a) contacting the biological sample with one or more of the peptide and/or polypeptides of the application under conditions suitable for binding of the one or more polypeptides to CDVs to form complexes, and (b) fractionating the complexes.

The CDVS contain for example heat shock proteins that allow for identifying substances in the CDVs relevant for disease research and/or clinical analysis. Accordingly, in an embodiment, the one or more substances relevant for discovery, research or clinical analysis are proteins, for example, cancer-related proteins or other molecules including for example nucleic acids such as RNA, miRNA, large intergenic non-coding RNAs (lincRNAs), as well as other molecules such as linear and branched polysaccharides, which are comprised in the complexes.

The disease proteins can be for example associated with HSP either directly or through associated pathways and/or from other from CDVs.

Also provided is a method of diagnosing an infectious disease such as a parasitic disease or cancer in a subject comprising: (a) contacting a sample from the subject with one or more peptides and/or polypeptides of the application under conditions suitable for the binding of the of the one or more peptides and/or polypeptides to CDVs to form complexes, (b) fractionating the complexes, and (c) detecting the presence of one or more infection and/or cancer relevant substances in the complexes, wherein the presence of the one or more cancer relevant substances is indicative of the diagnosis or prognosis of the cancer.

A further aspect includes a method of inducing an immune response and/or treating cancer comprising administering an effective amount of one or more of the peptides, polypeptides, complex, nucleic acid and/or the agent described herein to a subject in need thereof.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The application will now be described in greater detail with reference to the drawings in which.

Figure 1:
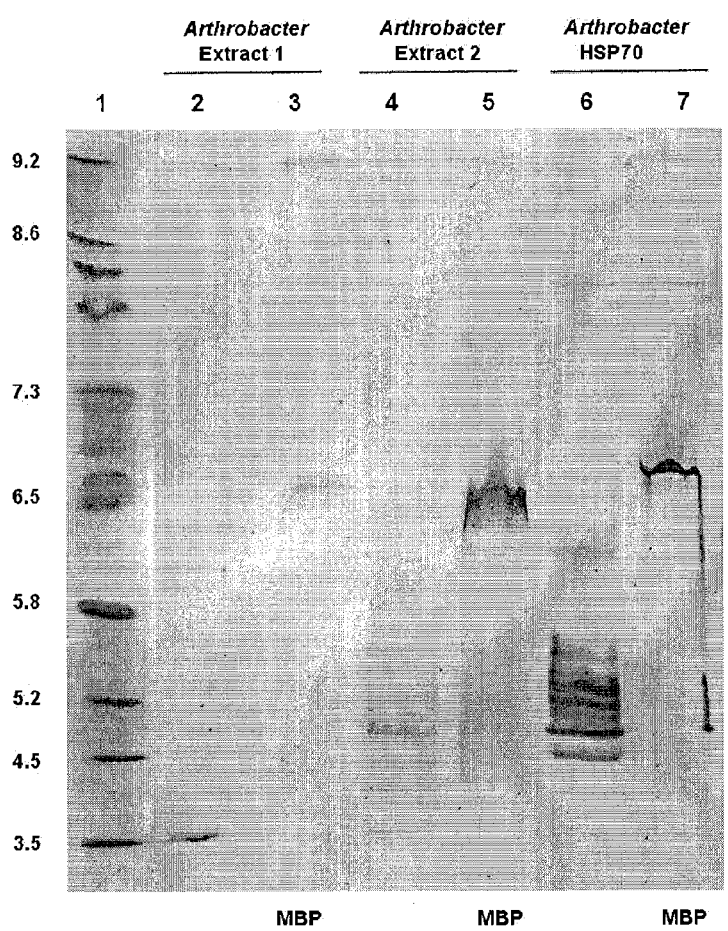
FIG. 1 shows the binding of extracts and recombinant proteins of A. davidanieli to myelin basic protein as determined by affinity isoelectric focusing. Lane 1: isoelectric point (pI) standards applied at the cathode (bottom of gel). Basic proteins (e.g. pI 9.2) migrate to the anode (top of gel) while acidic proteins migrate near to cathode. Proteins extracted from A. davidanieli using extraction buffer 1 were applied close to the anode in lanes 2 and 3. Similarly, proteins extracted using extraction buffer 2 were applied in lanes 4 and 5. 10 g of recombinant A. davidanieli HSP70 was applied in lanes 6 and 7. 50 µg of myelin basic protein in 3.5M urea were applied at the cathode of lanes 3, 5 and 7. The CHIEF complex between MBP and adHSP70 focuses near the 6.5 pH marker.

DETAILED DESCRIPTION OF THE APPLICATION (i) Definitions

The following definitions, unless otherwise stated, apply to all aspects and embodiments of the present application.

The term "HSP associated complex" as used herein refers to a complex formed between a HSP and one or more substances, for e.g. proteins, that bind to HSPs.

The term "binds a heat shock protein" refers to a polypeptide or peptide portion that forms a complex with a heat shock protein (HSP), such as HSP70 or a particular HSP such as a corynebacterial HSP.

The term "peptide of the present application" or "polypeptide of the application" as used herein refers to any of the generic or specific peptides or polypeptides encompassed by the present application, including, for example, [SEQ ID NOs: 1-127] and functionally equivalent peptides and polypeptides thereof and mixtures thereof. Generic peptides and polypeptides refer to peptides and polypeptides that have been identified by name, for example, survivin (SVV), Wilms tumor protein 1 (WT1), mylin basic protein (MBP), mucin-1, transient receptor potential cation channel subfamily V, member 6 (TRPV-6), and include forms from all species, such as mammal, including human.

The term "cancer" as used herein means a metastatic and/or a non-metastatic cancer, and includes primary and secondary cancers.

The terms "polypeptide," "peptide" and "protein" refer to a polymer of amino acid residues. The terms apply to naturally occurring amino acid polymers as well as amino acid polymers in which one or more amino acid residues are a non-naturally encoded amino acid. As used herein, the terms encompass amino acid chains of any length, including full length proteins, wherein the amino acid residues are linked by covalent peptide bonds. The polypeptides, peptides and proteins are written using standard sequence notation, with the nitrogen terminus being on the left and the carboxy terminus on the right. Standard single letter notations have been used as follows:

A—alanine
C—cysteine
D—aspartic acid
E—glutamic acid
F—phenylalanine
G—glycine
H—histidine
S—Isoleucine
K—lysine
L—leucine
M—methionine
N—asparagine P—proline
Q—glutamine
R—arginine
S—serine
T—threonine
V—valine
W—tryptophan
Y—tyrosine The term "peptide portion" as used herein can refer to a polymer of amino acids that has a length of at least 8, 9, 10, 11, 12, 13, 14, 15, 16, 17 or more amino acids, for example 20 amino acids, 30, amino acids, 40 amino acids, 50 amino acids, for example 8 to 50 amino acids, 9 to 50 amino acids, 10 to 50 amino acids etc 8 to 40 amino acids, 8 to 30 amino acids, 8 to 20 amino acids, 9 to 40 amino acids, 9 to 30 amino acids etc or a full length protein.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs, including non-naturally occurring amino acids and modified naturally occurring amino acids, refers to compounds that have the same basic chemical structure as a naturally occurring amino acid, i.e., a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as .beta.-alanine, ornithine, etc.; and chemically synthesized compounds having properties known in the art to be characteristic of amino acids. Examples of non-naturally occurring amino acids include, but are not limited to, .alpha.-methyl amino acids (e.g., .alpha.-methyl alanine), D-amino acids, histidine-like amino acids (e.g., 2-amino-histidine, .beta.-hydroxy-histidine, homohistidine, .alpha.-fluoromethyl-histidine and .alpha.-methyl-histidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids or substituted amino acids, may be advantageous in a number of different ways.

The terms "functionally equivalent peptide" and "functionally equivalent polypetide" as used herein means a peptide or polypeptide that bears the similar electrostatic and sterochemical attributes of the sequence under consideration comprising one or more conservative amino acid substitutions, analog amino acids substitutions and/or deletions and/or additions of amino acids that do not significantly affect or alter the function of the peptide. "Functionally equivalent peptides" and "functionally equivalent polypetides" also includes peptides and polypetides having homologous amino acid sequences to a referenced peptide or polypeptide.

"Conservative substitutions" applies to both amino acid and nucleic acid sequences. With respect to particular nucleic acid sequences, "conservatively substitution" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is "conservatively substituted" where the alteration results in the deletion of an amino acid, addition of an amino acid, or substitution of an amino acid with a chemically similar amino acid. Conservative substitution tables providing functionally similar amino acids are known to those of ordinary skill in the art.

Conservative substitution tables providing functionally similar amino acids are known to those of ordinary skill in the art. The following eight groups each contain amino acids that are conservative substitutions for one another:
The term "conservative amino acid substitutions" refers to all substitutions wherein the substituted amino acid has similar structural or chemical properties with the corresponding amino acid in the reference sequence. By way of example, conservative amino acid substitutions involve substitution of one aliphatic or hydrophobic amino acids, e.g., alanine, valine, leucine, isoleucine, methionine, phenylalanine, or tryptophan with another; substitution of one hydroxyl-containing amino acid, e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine and histidine, with another; and replacement of one small amino acid, e.g., alanine, serine, threonine, and glycine, with another.

As used herein "deletions" and "additions" in reference to amino acid sequence, means deletion or addition of one or more amino acids to the amino terminus, the carboxy terminus, the interior of the amino acide sequence or a combination thereof, for example the addition can be to one of the sequences of the present application.

As used herein, "homologous sequences" have an amino acid sequences which are at least 70%, at least 80%, at least 90%, at least 95%, or at least 99% homologous to the corresponding reference sequences. Sequences which are at least 90% identical have no more than 1 alteration, i.e., any combination of deletions, additions or substitutions, per 10 amino acids of the reference sequence. Percent homology is determined by comparing the amino acid sequence of the variant with the reference sequence using, for example, MEGA-LIGN™ project in the DNA STAR™ program.

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, may be obtained by a process comprising the steps of screening a library under stringent hybridization conditions with a labeled probe having a polynucleotide sequence of the invention or a fragment thereof, and isolating full-length cDNA and genomic clones containing said polynucleotide sequence. Such hybridization techniques are well known to the skilled artisan.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, including but not limited to, by the local homology algorithm of Smith and Waterman (1970) Adv. Appl. Math. 2:482c, by the homology alignment algorithm of Needleman and Wunsch (1970) J. Mal. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

One example of an algorithm that is suitable for determining percent sequence identity and sequence similarity are the BLAST and BLAST 2.0 algorithms, which are described in Altschul et al. (1997) Nuc. Acids Res. 25:3389-3402, and Altschul et al. (1990) J. Mol. 215:403-410, respectively. Software for performing BLAST analyses is publicly available through the National Center for Biotechnology Information available at the World Wide Web at ncbi.nlm.nih.gov. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1992) Proc. Natl. Acad, Sci. USA 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, PNA, or other nucleic acid mimics, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, Laboratory Techniques in Biochemistry and Molecular Biology—Hybridization with Nucleic Probes, "Overview of principles of hybridization and the strategy of nucleic acid assays" (1993). Generally, stringent conditions are selected to be about 5-10.degree. C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, typically about 0.01 to 1.0 M sodium ion concentration (or other salts) at pH 7.0 to 8.3 and the temperature is at least about 30.degree. C. for short probes (including but not limited to, 10 to 50 nucleotides) and at least about 60.degree. C. for long probes (including but not limited to, greater than 50 nucleotides). Stringent conditions may also be achieved with the addition of destabilizing agents such as formamide. For selective or specific hybridization, a positive signal may be at least two times background, optionally 10 times background hybridization. Exemplary stringent hybridization conditions can be as following: 50% formamide, 5.times.SSC, and 1% SDS, incubating at 42.degree. C., or 5.times.SSC, 1% SDS, incubating at 65.degree. C., with wash in 0.2.times.SSC, and 0.1% SDS at 65.degree. C. Such washes can be performed for 5, 15, 30, 60, 120, or more minutes.

The term "linker peptide" as used herein means any short stretch of amino acids, for example 3-20 amino acids or any number in between, for example comprising glycine and serine amino acids and/or comprising a cleavage site.

The term "pharmaceutically acceptable" means compatible with the treatment of animals, in particular humans.

The term "subject" as used herein includes all living organisms, including members of the animal and plant kingdom. In an embodiment of the application, the subject is a mammal, and suitably a human.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. For example, a subject with early stage cancer can be treated to prevent progression or metastases, or alternatively a subject in remission can be treated with a compound or composition described herein to prevent recurrence. Treatment methods comprise administering to a subject a therapeutically effective amount of a polypeptide of the application, and optionally consist of a single administration (or alternatively comprises) a series of applications. For example, the polypeptides of the application may be administered at least once a week. However, in another embodiment, the polypeptides may be administered to the subject from about one time per three weeks, or about one time per week to about once daily for a given treatment. In another embodiment, the polypeptide is administered 1 to 6 times daily. The length of the treatment period depends on a variety of factors, such as the severity of the disease, the age of the patient, the concentration, the activity of the polypeptides described herein, and/or a combination thereof. It will also be appreciated that the effective dosage of the polypeptide used for the treatment or prophylaxis may increase or decrease over the course of a particular treatment or prophylaxis regime. Changes in dosage may result and become apparent by standard diagnostic assays known in the art. In some instances, chronic administration may be required. For example, the polypeptides are administered to the subject in an amount and duration sufficient to treat the patient.

The term "disease associated antigen" or "DAA" or "disease associated peptide" or DAP which are used interchangeably as used herein means any antigenic substance produced and/or associated with a disease or pathological event, such as an infectious and/or parasitic disease such as a bacterial, fungal, protozoal, viral and/or worm infection and/or cancer (e.g. tumour associated antigens). Developmental and spontaneous conditions which are associated with a disease associated antigen are also contemplated An example includes as Hodgkin's disease Ki-1 antigen. The DAA when proteinaceous can for example be a sequence of 8, 9, 10 or more amino acids up to the full protein and/or any number of amino acids in between 8 and the full length protein which comprises at least one antigenic fragment of the full length protein that can be represented in a MHC complex.

The term "tumour antigen" (i.e. TA) or "tumour associated antigen" (i.e. TAA) as used herein means any antigenic substance produced in tumor cells that triggers an immune response in a host (e.g. which can be re-presented by MHC complexes). For example, TAs include tumour associated antigens as well as tumour specific antigens such as antigenic peptides from Wilms tumour 1 (WT1), survivan, mucin-1 and TRPV-6 as well as p53, Ras, alphafetoprotein (AFP), carcinoembryonic antigen (CEA) and dermcidin. The TAA when proteinaceous can for example be a sequence of 8 or more amino acids up to the full protein any number of amino acids in between 8 and the full length protein which comprises at least one antigenic fragment of the full length protein that can be represented in a MHC complex.

As used herein, the term "effective amount" or "therapeutically effective amount" means an amount effective, at dosages and for periods of time necessary to achieve the desired result. For example, in the context or treating cancer, an effective amount is an amount that, for example, induces remission, reduces tumor burden, and/or prevents tumor spread or growth compared to the response obtained without administration of the compound. Effective amounts may vary according to factors such as the disease state, age, sex, weight of the subject. The amount of a given polypeptide that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art.

As used in this specification and the appended claims, the singular forms "a", "an" and "the" include plural references unless the content clearly dictates otherwise. Thus for example, a composition containing "a polypeptide" includes one such peptide or a mixture of two or more additional peptides.

In embodiments comprising an "additional" or "second" component, the second component as used herein is chemically different from the other components or first component. A "third" component is different from the other, first, and second components, and further enumerated or "additional" components are similarly different.

The term "suitable" as used herein means that the selection of the particular conditions would depend on the specific method to be performed, but the selection would be well within the skill of a person trained in the art. All method or process steps described herein are to be conducted under conditions sufficient to provide the desired result. Unless otherwise indicated, a person skilled in the art would understand that all method or process conditions, including, for example, solvent, time, temperature, pressure, reactant ratio and whether or not the method should be performed under an anhydrous or inert atmosphere, can be varied to optimize the desired result and it is within their skill to do so.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

(ii) Peptides and Polypeptides and Agents of the Application

Gel isoelectric focusing was initially used to combine HSP70 from the salmon vaccine *Arthrobacter davidanieli* as a counter migrant to a basic peptide portion identified within the amino acid sequence of bovine myelin basic protein (bMBP). This initial discovery garnered further interest when it was subsequently determined that, antigenic amino acid sequences from known tumor antigens (TAs) could be conjugated to the MBP sequence, with the resulting polypeptides bound to all classes of HSPs (HSP60, HSP70 and HSP90) and their variants normally restricted to specific subcellular compartments (e.g. GRP78 and gp96). The method used to combine the peptides/polypeptides and HSPs is referred to as counter HSP isoelectric focusing (CHIEF).

During the initial investigations into the binding properties of the peptides and polypeptides of the present application, it was determined that these entities had a potential application in the profiling of cellular HSP associated complexes (HACs). CHIEF of the polypeptides with cytoplasmic or membrane-associated proteins from cancer cells lead to the creation and focusing of co-migrating complexes of HACs. Mass spectrometry of the HACs determined that CHIEF captured between 50-100 other proteins characteristically upregulated by cancer cells. It was subsequently determined that peptide capture of HACs for example cancer cell HACs could also be achieved by admixture and low speed centrifugation.

Because cancer cells require HSPs for protein function and overall survival, the affinity enrichment of HSP-dependent proteins represents a universal approach to harvest discrete protein profiles from individual cancers with a single method. Such profiles may contain biomarkers for patient staging as well as determinants of drug sensitivity and recurrence free survival.

It was also determined that the peptides and polypeptides of the present application can be used to capture HACs such as found on cells and in cell derived vesicles (CDVs) as found for example in the extracellular medium (ECM) of cancer cells, infected cells and in body fluids. This latter property of peptides and polypeptides of the application may be due to anomalous surface location of HSPs in cancer an infected cells. However it has been subsequently determined that vesicular material with little or no detectable HSPs could be sedimented from platelet free plasma (PFP). This observation suggests that the peptides bind to additional vesicular components that have yet to be identified.

Western blot and mass spectrometry further confirmed that the protein content of peptide- and polypeptide-affinity enriched vesicular material from cultured breast and prostate cancer cells was similar to that of exosomes pelleted from culture medium by ultracentrifugation (identity confirmed by transmission electron microscopy). Further investigation determined that CDVs from the culture medium of breast and prostate cancer cells also contained intact mRNA. mRNA species were identifiable qualitatively and quantitatively by direct hybridisation to 22,000 oligo microarray slides, without the need for PCR amplification.

The present application therefore includes an isolated peptide consisting of 8 to 50 amino acids and comprising an α-helix forming-amino acid sequence that binds a heat shock protein, the α-helix-forming amino acid sequence selected from:

i) a sequence comprising at least 8 to 12 contiguous amino acids of $X^1$-$X^2$-$X^3$-$X^4$-$X^5$-$X^6$-$X^7$-$X^8$-$X^9$-$X^{10}$-$X^{11}$—$X^{12}$ [SEQ ID NO:1], wherein
$X^1$ is G, A, D, or E;
$X^2$ is R, H or K;
$X^3$ is G, A, S or T;
$X^4$ is R, H, K, N or Q;
$X^5$ is G, A, S or T;
$X^6$ is A, V, I, L, M, F or W;
$X^7$ is G, A, S or T;
$X^8$ is A, V, I, L or G;
$X^9$ is S, T, M, A, V, I or L;
$X^{10}$ is R, H, K, N or Q;
$X^{11}$ is A, V, I, L M, F or W; and
$X^{12}$ is D, E, S, or T; and ii) functionally equivalent peptides of the sequences of (i).

It is an embodiment of the application that:
$X^1$ is G or A;
$X^2$ is R, H or K;
$X^3$ is G, A, S or T;
$X^4$ is R, H or K;
$X^5$ is G, A, S or T;
$X^6$ is A, V, I, L, M, F or W;
$X^7$ is G, A, S or T;
$X^8$ is A, V, I, L or G;
$X^9$ is S or T;
$X^{10}$ is R, H or K;
$X^{11}$ is A, V, I, L M, F or W; and
$X^{12}$ is S, or T.

In another embodiment of the application the isolated peptide comprises 10-12, suitably 12, contiguous amino acids of $X^1$-$X^2$-$X^3$-$X^4$-$X^5$-$X^6$-$X^7$-$X^8$-$X^9$-$X^{10}$-$X^{11}$-$X^{12}$.

In another embodiment of the application, the isolated peptide consists of 18 amino acids, in particular, the isolated peptide consists of 3 amino acids on each of the carbon and nitrogen termini of [SEQ ID NO. 1].

In yet another embodiment, the isolated peptide is selected from:

(i)  PSQGKGRGLSLSRFSWGA;  [SEQ ID NO 2:]

(ii)  PSQGKGRG;  [SEQ ID NO: 3]

(iii)  GRGLSLSRF;  [SEQ ID NO: 4]

(iv)  SLSRFSWGA;  [SEQ ID NO: 5]
and

```
                                                [SEQ ID NO: 6]
        (v)          GWGDRGNGFGLMQVDKRY;
```
and ii) functionally equivalent peptides to the sequences of (i)-(v).

In yet another embodiment, the isolated peptide is selected from:

```
                                                [SEQ ID NO 2:]
        (i)   PSQGKGRGLSLSRFSWGA;
        and

[SEQ ID NO: 6]
        (v)   GWGDRGNGFGLMQVDKRY.
```

It is another embodiment of the application that the isolated peptide, further comprises a linker moiety, a secondary modification and/or label selected from phosphorylation, acylation, acetylation, formylation, glycosylation, amidation, incorporation of chromophores, fluorescent dyes/fluorogenic groups, PEGylation, biotinylation and sulfation. For example, the linker moiety comprises a linker peptide sequence, and/or the secondary structure or label comprises biotin.

In an embodiment of the application the isolated peptides further comprise at least one second peptide portion comprising an antigenic amino acid sequence and/or an α-helix stabilizing amino acid sequence The present application therefore includes novel polypeptides comprising a first α-helical peptide portion comprising hydrophobic, uncharged non-polar and basic amino acids, for example such a sequence derived from myelin basic protein (MBP), lysozyme or histone. The first portion has an affinity for heat shock proteins (HSPs) such as corynebacterial HSPs (e.g. *Mycobacterium* and *Arthrobacterium* spp.). The binding proclivity of the first peptide portion is considerably enhanced by the addition of certain flanking peptides (second peptide portions). These flanking peptides are believed to stabilise the α-helix and increase the affinity of the polypeptide for HSPs. The second peptide portions may include, for example, the immunostimulatory epitopes of one or more tumor associated antigens. In an embodiment of the application, these have been derived from the well established TAAs, survivin and Wilms tumor protein 1.

Accordingly, the present application includes a polypeptide comprising (a) a first peptide portion that comprises an α-helix-forming amino acid sequence that binds a heat shock protein; and (b) at least one second peptide portion comprising an antigenic amino acid sequence and/or an α-helix-stabilizing amino acid sequence that increases the interaction of the first peptide portion with the heat shock protein.

In an embodiment of the application, the first peptide portion comprises a fragment from a protein that comprises basic, uncharged polar and hydrophobic amino acids and binds, on its own, to corynebacterial HSPs, such as HSPs from a *Mycobacterium* or *Arthrobacterium* species. In another embodiment, the first peptide portion comprises hydrophobic amino acids in the center positions of the peptide, few or no acidic amino acids, and non-charged polar, basic and/or aromatic amino acids flanking the hydrophobic groups. In yet another embodiment the non-charged polar, hydrophobic and basic amino acids are interpolated with smaller amino acids, for example, serine and glycine. While not wishing to be limited by theory, it is believed that these smaller amino acids permit some spacing of the binding amino acids allowing steric interaction and flexibility of the binding amino acids residues with compatible electrostatic regions of the binding cleft of the interacting protein. In another embodiment, the first peptide portion comprises a fragment from a non-pathogenic region of myelin basic protein (MBP), lysozyme or histone that comprises basic, uncharged polar and hydrophobic amino acids. In another embodiment, the first peptide portion is a fragment from a non-pathogenic region of bovine MBP that comprises basic, uncharged polar and hydrophobic amino acids.

The first peptide portion as mentioned comprises an α-helix forming amino acid sequence. Short peptides can be constrained in α-helical conformation using method known in the art. For example, Patgiri et al 2008 describes methods of stabilizing short peptide α-helical conformations by for example introduction of stabilizing hydrogen bonds into the peptide sequence.

In an embodiment, the first peptide portion of the polypeptide of the application is a peptide consisting of 8 to 50 amino acids and comprising an α-helix forming-amino acid sequence that binds a heat shock protein, the α-helix-forming amino acid sequence selected from:

i) a sequence comprising at least 8 to 12 contiguous amino acids of $X^1$-$X^2$-$X^3$-$X^4$-$X^5$-$X^6$-$X^7$-$X^8$-$X^9$-$X^{10}$-$X^{11}$-$X^{12}$ [SEQ ID NO:1], wherein $X^1$ is G, A, D, or E;

$X^2$ is R, H or K;

$X^3$ is G, A, S or T;

$X^4$ is R, H, K, N or Q;

$X^5$ is G, A, S or T;

$X^6$ is A, V, I, L, M, F or W;

$X^7$ is G, A, S or T;

$X^8$ is A, V, I, L or G;

$X^9$ is S, T, M, A, V, I or L;

$X^{10}$ is R, H, K, N or Q;

$X^{11}$ is A, V, I, L M, F or W; and $X^{12}$ is D, E, S, or T; and ii) functionally equivalent peptides of the sequences of (i).

In yet another embodiment, the first peptide portion is selected from:

```
                                      [SEQ ID NO 2:]
  (i)          PSQGKGRGLSLSRFSWGA;

[SEQ ID NO: 3]
  (ii)         PSQGKGRG;

[SEQ ID NO: 4]
  (iii)        GRGLSLSRF;

[SEQ ID NO: 5]
  (iv)         LSRFSWGA;
  and

[SEQ ID NO: 6]
  (v)          GWGDRGNGFGLMQVDKRY;
``` and ii) functionally equivalent peptides to the sequences of (i)-(v).

In yet another embodiment, the first peptide portion is selected from:

```
                                      [SEQ ID NO 2:]
      (i) PSQGKGRGLSLSRFSWGA;
      and

[SEQ ID NO: 6]
      (v) GWGDRGNGFGLMQVDKRY.
```

In an embodiment of the application, the at least one second peptide portion comprises clinically or physiologically relevant amino acid sequences, such as immunomodulatory epitopes of cancer proteins that are compatible with being adsorbed and re-presented in association with MHC complexes. Accordingly, in one embodiment, the at least one second peptide portion comprises an amino acid sequence that has previously been shown to prompt or augment an immune response, for example to pathologic events such as cancer, infectious disease, developmental or spontaneous conditions. In another embodiment, the at least one second peptide portion comprises an immunostimulatory epitope from a tumor associated antigen, such as survivin, mucin-1, transient receptor potential cation channel subfamily V, member 6 (TRPV6) or Wilms tumor protein-1 (WT1).

In another embodiment, the at least one second peptide portion comprises one or more of:

STFKNWPFL, [SEQ ID NO: 7]

LTLGEFLKL; [SEQ ID NO: 8]

LRRKCAVPS; [SEQ ID NO: 9]

GVTSAPDTR; [SEQ ID NO: 10]

MFLQIYKQG; [SEQ ID NO: 11]

FLQIYKQGG; [SEQ ID NO: 12]

LQIYKQGGF; [SEQ ID NO: 13]

QIYKQGGFL; [SEQ ID NO: 14]

IYKQGGFLG; [SEQ ID NO: 15]

YKQGGFLGL; [SEQ ID NO: 16]

VVQLTLAFR; [SEQ ID NO: 17]

FNQYKTEAA; [SEQ ID NO: 18]

NQYKTEAAS; [SEQ ID NO: 19]

QYKTEAASR; [SEQ ID NO: 20]

YKTEAASRY; [SEQ ID NO: 21]

GQLDIFPAR; [SEQ ID NO: 22]

KGLILCLWS; [SEQ ID NO: 23]

GLILCLWSK; [SEQ ID NO: 24]

LILCLWSKF; [SEQ ID NO: 25]

ILCLWSKFC; [SEQ ID NO: 26]

LCLWSKFCR; [SEQ ID NO: 27]

CLWSKFCRW; [SEQ ID NO: 28]

LWSKFCRWF; [SEQ ID NO: 29]

WSKFCRWFQ; [SEQ ID NO: 30]

SKFCRWFQR; [SEQ ID NO: 31]

ESPLLLAAK; [SEQ ID NO: 32]

QALNKLLKY; [SEQ ID NO: 33]

NLVRALLAR; [SEQ ID NO: 34]

LVRALLARR; [SEQ ID NO: 35]

VRALLARRA; [SEQ ID NO: 36]

RALLARRAS; [SEQ ID NO: 37]

ALLARRASV; [SEQ ID NO: 38]

LLARRASVS; [SEQ ID NO: 39]

LARRASVSA; [SEQ ID NO: 40]

ARRASVSAR; [SEQ ID NO: 41]

RRASVSARA; [SEQ ID NO: 42]

RASVSARAT; [SEQ ID NO: 43]

ASVSARATG; [SEQ ID NO: 44]

SVSARATGT; [SEQ ID NO: 45]

VSARATGTA; [SEQ ID NO: 46]

SARATGTAF; [SEQ ID NO: 47]

ARATGTAFR; [SEQ ID NO: 48]

LQPNKTFAC; [SEQ ID NO: 49]

YNLLLSYDR; [SEQ ID NO: 50]

KRKHTQWTY; [SEQ ID NO: 51]

LLELIITTK; [SEQ ID NO: 52]

LVSLKWKRY; [SEQ ID NO: 53]

VSLKWKRYG; [SEQ ID NO: 54]

SLKWKRYGR; [SEQ ID NO: 55]

LKWKRYGRP; [SEQ ID NO: 56]

KWKRYGRPY; [SEQ ID NO: 57]

NTLLQQKLL; [SEQ ID NO: 58]

TIMIQKMIF; [SEQ ID NO: 59]

KLPRCLWPR; [SEQ ID NO: 60]

LGDRWFLRV; [SEQ ID NO: 61]

RYAQAFHTR; [SEQ ID NO: 62]
or

PSQASSGQARMFPNAPYLPSCLE [SEQ ID No: 63]
or functionally equivalent sequences of [SEQ ID NOs 7-62].

In another embodiment, the at least one second peptide portion contributes to the selectivity of the affinity of the polypeptide. For example, HACs from sub-cellular extracts are more efficiently fractionated using [SEQ ID NO:9], while [SEQ ID NO:8] is more efficient at fractionating vesicular material from culture medium or biological fluid.

In another embodiment of the application, the first and at least one second peptide portions are joined by a linker moiety. In an embodiment of the application the linker moiety is a peptide comprising from 1 to 15, 2 to 10 or 3 to 5 amino acids. In another embodiment, the first and second peptide portions are joined by a covalent bond. In an embodiment the linker moiety comprises glycine and/or serine amino acids. In a further embodiment, the linker moiety comprises sites that are cleaved by enzymes in vivo.

In yet another embodiment of the application, the first peptide portion is at the N-terminus of the polypeptide and comprises one second peptide portion at the C-terminus. In another embodiment, the first peptide portion of the polypeptide is located centrally between two second peptide portions, which may be the same or different.

In yet another embodiment the polypeptides of the present application comprise, consist essentially of or consists of any combination of the first petide portions ([SEQ ID NOs: 1-6]) and second peptide portions ([SEQ ID NOs: 7-63]) listed above.

In yet another embodiment the polypeptides of the present application comprise, consist essentially of or consists of an amino acid sequence selected from:

PSQGKGRGLSLSRFSWGASTFKNWPFL; [SEQ ID NO: 64]

PSQGKGRGLSLSRFSWGALTLGEFLKL; [SEQ ID NO: 65]
and

PSQGKGRGLSLSRFSWGALRRKCAVPS [SEQ ID NO: 66]

PSQGKGRGLSLSRFSWGAPSQASSGQARMFPNAPYLPSCLE; [SEQ ID NO: 67]

PSQGKGRGSTFKNWPFL; [SEQ ID NO: 68]

GRGLSLSRFSTFKNWPFL; [SEQ ID NO: 69]

SLSRFSWGALRRKCAVPS; [SEQ ID NO: 70]

SLSRFSWGALTLGEFLKL; [SEQ ID NO: 71]

PSQGKGRGLSLSRFSWGAGVTSAPDTR; [SEQ ID NO: 72]

PSQGKGRGLSLSRFSWGAMFLQIYKQG; [SEQ ID NO: 73]

PSQGKGRGLSLSRFSWGAFLQIYKQGG; [SEQ ID NO: 74]

PSQGKGRGLSLSRFSWGALQIYKQGGF; [SEQ ID NO: 75]

PSQGKGRGLSLSRFSWGAQIYKQGGFL; [SEQ ID NO: 76]

PSQGKGRGLSLSRFSWGAIYKQGGFLG; [SEQ ID NO: 77]

PSQGKGRGLSLSRFSWGAYKQGGFLGL; [SEQ ID NO: 78]

PSQGKGRGLSLSRFSWGAVVQLTLAFR; [SEQ ID NO: 79]

PSQGKGRGLSLSRFSWGAFNQYKTEAA; [SEQ ID NO: 80]

PSQGKGRGLSLSRFSWGANQYKTEAAS; [SEQ ID NO: 81]

PSQGKGRGLSLSRFSWGAQYKTEAASR; [SEQ ID NO: 82]

PSQGKGRGLSLSRFSWGAYKTEAASRY; [SEQ ID NO: 83]

PSQGKGRGLSLSRFSWGAGQLDIFPAR; [SEQ ID NO: 84]

PSQGKGRGLSLSRFSWGAKGLILCLWS; [SEQ ID NO: 85]

PSQGKGRGLSLSRFSWGAGLILCLWSK; [SEQ ID NO: 86]

PSQGKGRGLSLSRFSWGALILCLWSKF; [SEQ ID NO: 87]

PSQGKGRGLSLSRFSWGAILCLWSKFC; [SEQ ID NO: 88]

PSQGKGRGLSLSRFSWGALCLWSKFCR; [SEQ ID NO: 89]

PSQGKGRGLSLSRFSWGACLWSKFCRW; [SEQ ID NO: 90]

PSQGKGRGLSLSRFSWGALWSKFCRWF; [SEQ ID NO: 91]

PSQGKGRGLSLSRFSWGAWSKFCRWFQ; [SEQ ID NO: 92]

PSQGKGRGLSLSRFSWGASKFCRWFQR; [SEQ ID NO: 93]

PSQGKGRGLSLSRFSWGAESPLLLAAK; [SEQ ID NO: 94]

PSQGKGRGLSLSRFSWGAQALNKLLKY; [SEQ ID NO: 95]

PSQGKGRGLSLSRFSWGANLVRALLAR; [SEQ ID NO: 96]

PSQGKGRGLSLSRFSWGALVRALLARR; [SEQ ID NO: 97]

PSQGKGRGLSLSRFSWGAVRALLARRA; [SEQ ID NO: 98]

PSQGKGRGLSLSRFSWGARALLARRAS; [SEQ ID NO: 99]

PSQGKGRGLSLSRFSWGAALLARRASV; [SEQ ID NO: 100]

PSQGKGRGLSLSRFSWGALLARRASVS; [SEQ ID NO: 101]

PSQGKGRGLSLSRFSWGALARRASVSA; [SEQ ID NO: 102]

PSQGKGRGLSLSRFSWGAARRASVSAR; [SEQ ID NO: 103]

PSQGKGRGLSLSRFSWGARRASVSARA; [SEQ ID NO: 104]

PSQGKGRGLSLSRFSWGARASVSARAT; [SEQ ID NO: 105]

PSQGKGRGLSLSRFSWGAASVSARATG; [SEQ ID NO: 106]

PSQGKGRGLSLSRFSWGASVSARATGT; [SEQ ID NO: 107]

PSQGKGRGLSLSRFSWGAVSARATGTA; [SEQ ID NO: 108]

PSQGKGRGLSLSRFSWGASARATGTAF; [SEQ ID NO: 109]

PSQGKGRGLSLSRFSWGAARATGTAFR; [SEQ ID NO: 110]

PSQGKGRGLSLSRFSWGALQPNKTFAC; [SEQ ID NO: 111]

PSQGKGRGLSLSRFSWGAYNLLLSYDR; [SEQ ID NO: 112]

PSQGKGRGLSLSRFSWGAKRKHTQWTY; [SEQ ID NO: 113]

PSQGKGRGLSLSRFSWGALLELIITTK; [SEQ ID NO: 114]

PSQGKGRGLSLSRFSWGALVSLKWKRY; [SEQ ID NO: 115]

PSQGKGRGLSLSRFSWGAVSLKVVKRYG; [SEQ ID NO: 116]

PSQGKGRGLSLSRFSWGASLKWKRYGR; [SEQ ID NO: 117]

PSQGKGRGLSLSRFSWGALKWKRYGRP; [SEQ ID NO: 118]

PSQGKGRGLSLSRFSWGAKWKRYGRPY; [SEQ ID NO: 119]

PSQGKGRGLSLSRFSWGANTLLQQKLL; [SEQ ID NO: 120]

PSQGKGRGLSLSRFSWGATIMIQKMIF; [SEQ ID NO: 121]

PSQGKGRGLSLSRFSWGAKLPRCLWPR; [SEQ ID NO: 122]

PSQGKGRGLSLSRFSWGALGDRWFLRV; [SEQ ID NO: 123]

PSQGKGRGLSLSRFSWGARYAQAFHTR; [SEQ ID NO: 124]
and

PSQGKGRGLSLSRFSWGAPSQASSGQARMFPNAPYLPSCLE, [SEQ ID No: 125]
and functionally equivalent sequences of [SEQ ID NOs 64-125].

In yet another embodiment the polypeptides of the present application comprise, consist essentially of or consists of an amino acid sequence selected from:

PSQGKGRGLSLSRFSWGASTFKNWPFL; [SEQ ID NO: 64]

PSQGKGRGLSLSRFSWGALTLGEFLKL; [SEQ ID NO: 65]
and

PSQGKGRGLSLSRFSWGALRRKCAVPS, [SEQ ID NO: 66]
and functionally equivalent sequences of [SEQ ID NOs 64-125].

Functional equivalents of the peptide and polypeptide sequences of the present application are identified by modifying the sequence of the peptide or polypeptide and then assaying the resulting peptide or polypeptide for the ability to interact with heat shock proteins, in the case of the first peptide portion, and to bind the MHC or augment the immune response, in the case of the second peptide portion. Functional equivalents of the peptides and polypeptides of the present application are identified by modifying the sequence of the peptide or polypeptide and then assaying the resulting peptide or polypeptide for the ability to bind HSPs. Peptides and polypetides that exhibit at least 50%, at least 60%, at least 70%, at least 80% or at least 90% of the binding activity of the non-modified sequence are considered functionally equivalent.

The peptides and polypeptides of the present application may be synthesized using commercially available peptide synthesizers. For example, the chemical methods described in Kaumaya et al. (1994), "DE NOVO" ENGINEERING OF PEPTIDE IMMUNOGENIC AND ANTIGENIC DETERMINANTS AS POTENTIAL, VACCINES, in Peptides, Design, Synthesis and Biological Activity (1994), pp 133-164, which is specifically incorporated herein by reference, may be used. For example, the first peptide portion may be synthesized in tandem with the one or more second peptide portions to form a polypeptide. Peptoids would be synthesized by modifications of the chemistry on similar equipment.

The peptides and polypeptides of the present application may also be produced using cell-free translation systems and RNA molecules derived from DNA constructs that encode the peptide. Alternatively, the peptides and polypeptides are made by transfecting host cells with expression vectors that comprise a DNA sequence that encodes the respective peptide and then inducing expression of the peptide or polypeptide in the host cells. For recombinant production, recombinant constructs comprising one or more of the sequences which encode the peptide or polypeptide, or a variant thereof are introduced into host cells by conventional methods such as calcium phosphate transfection, DEAE-dextran mediated transfection, transvection, microinjection, cationic lipid-mediated transfection, electroporation, transduction, scrape lading, ballistic introduction or infection. The peptide or polypeptide may be expressed in suitable host cells, such as for example, mammalian cells, yeast, bacteria, insect cells or other cells under the control of appropriate promoters using conventional techniques. Suitable hosts include, but are not limited to, E. coli, P. pastoris, Cos cells and 293 HEK cells. Following transformation of the suitable host strain and growth of the host strain to an appropriate cell density, the cells are harvested by centrifugation, disrupted by physical or chemical means, and the resulting crude extract retained for further purification of the peptide or polypeptide. Conventional procedures for isolating recombinant peptides from transformed host cells may be used, such as isolation by initial extraction from cell pellets or from cell culture medium, followed by salting-out, and one or more chromatography steps, including aqueous ion exchange chromatography, size exclusion chromatography steps, high performance liquid chromatography (HPLC), and affinity chromatography.

In yet another embodiment, the peptides or polypeptides of the present application are linked to a solid support. The solid support is one which facilitates isolation of the peptides or polypeptides, and any complexes formed with the peptides or polypeptides, from a mixture. Solid supports may include but are not restricted to microscopic beads (e.g. magnetic or chemically activated) or any materials used for the preparation of microarrays, microfluidic devices or titre plate based high volume analysis. Examples of such supports include, for example, polystyrene resins, polyamide resins, polyethylene glycol (PEG)-hybrid polystyrene resins, PEG resins and Dynal™ magnetic beads. Methods for coupling peptides to solid supports are well known in the art.

The peptide and polypeptide of the present application are useful for diagnostic and therapeutic applications. Accordingly, the present application also includes compositions comprising one or more of peptides and/or polypeptides of the present application and one or more additives, excipients and/or adjuvants. In one embodiment, the one or more additives comprises a detergent matrix, such as a detergent matrix that may be used for directly mixing with fractions of laboratory grown cells or biological fluids previously collected from plant, animal, patient and/or environmental samples. The detergents minimize non-specific co-enrichment of cellular materials that may occlude or dilute the affinity enriched molecules of interest. In an embodiment the composition is a diagnostic composition suitable for use in in vitro assays. In another embodiment, the composition is a pharmaceutical composition and the one or more additives, excipients and/or adjuvants are pharmaceutically acceptable.

The present application also includes a kit for fractionating one or more substances relevant for discovery, research or clinical analysis comprising one or more peptides and/or polypeptides of the present application or a composition comprising one or more peptides and/or polypeptides of the present application. In an embodiment, the kit is for fractionating CDVs from biological samples. In a further embodiment, the kit comprises instructions for use.

Typically the kit would contain a known amount of one or more peptides and/or polypeptides of the application. In addition the kit optionally includes accessories for washing such as tubes and bottles of phosphate buffered saline, detergents, protease inhibitors and any other material that might be required for straight-out-of-the-box immediate application. The kits optionally include detailed protocols and illustrations for enrichment of HAC and/or CDV and subsequent simple steps for the extraction of RNA, lipid and/or protein for down stream applications such as microarray, qRT-PCR, Western blot, mass spectrometry and other methods. The kits would be available in various sizes depending on the volume required by the user.

In another aspect of the present application, there is included a complex comprising a peptide or the polypeptide of the application and a heat shock protein, wherein the peptide or polypeptide and heat shock protein are affinity associated. In an embodiment, the complex the heat shock protein is selected from HSP60, HSP70, HSP90 or HSP27 or an isoform thereof.

A further aspect of the present application includes an agent comprising a peptide, polypeptide or a complex described herein and a bead which functions to link the polypeptide and/or peptide portions together.

In an embodiment, the peptide portions a) and b) are conjugated to the bead.

Any bead can be used including for example Dynal beads.

A further aspect includes an agent comprising a nucleic acid encoding a peptide or polypeptide described herein.

In an embodiment, the agent comprises a nucleic acid encoding the peptide portion a); and a nucleic acid encoding the peptide portion b).

The peptide, polypeptide, complex and/or agent can be in a composition with one or more additives, excipients and/or adjuvants.

(III) Uses of the Polypeptide of the Present Application

Because of the vital role played by HSPs and their interaction with cancer proteins, the fractionation of HSP associated complexes (HACs) from laboratory grown cells or cancer patient tissues and body fluids can provide information regarding malignancy and drug sensitivity (Redlak et al. 2010; Zhang et al. 2009; Bebawy et al. 2009), as well as providing a source of potential vaccine material (Li et al. 2008) and materials to study mode of action (Cantrell et al. 2010).

An overlap exists between the addictions of cancers to excessive and cell surface HSP expression and another criterion for aggressive behaviour: The abundant production and release of cell derived vesicles (CDVs) into surrounding tissue fluids. CDVs exist as structurally robust viral sized packages (30-200 nM) that deliver protein, nucleic acids and lipids from donor cells to recipients without the need for contact (Quesenberry et al. 2010a; Camussi et al. 2010; Simons et al. 2009; Lakkaraju et at. 2008). However, CDV release can also exacerbate human pathology (Anderson et al. 2010; Quesenberry et al. 2010b). This process has also been co-opted and frequently accelerated by cancer cells to distribute cancer promoting molecules among sister cells or to subvert the function of normal cells (Renzulli et al. 2010; Webber et al.

2010). Cancer CDVs imbibed by immune cells may thus interfere with rejection (Valenti et al. 2007; Xie et al. 2009; Szajnik et al. 2010; Xiang et al. 2010) and redirect blood vessel growth to nourish the cancer (Meckes et al. 2010; Park et al. 2010; Hong et al. 2009; Rak J. 2010). CDVs may also assist in the destruction of underlying matrix tissue and the subsequent migration and colonization of other sites by cancer cells within the host (Jung et al. 2009; Corcoran et al. 2010; Iguchi et al. 2010; McCready et al. 2010; Hendrix et al. 2010). Due to the prevalence and unusual membrane association of HSPs on cancer cells, it follows that cancer CDVs are richly accessorised by HSPs. Cancer activity is sometimes enabled directly through the accessorisation of CDVs with HSPs (Chalmin et al. 2010), (see also McCready et al 2010) and may render them more resistant to chemical and physical stimuli; perhaps due to increased membrane rigidity which in turn provides better resistance to chemo or radiotherapy (Pfister et al. 2007; Dempsey et al. 2010). As such, cancer CDVs are HSP associated complexes and perhaps the largest such complex that can exist being essentially an anucleate and robust miniature version of the originating cancer cell, albeit with particular emphasis on the packaging of lipids, RNA, and proteins that promote tumor growth (Keller et al. 2009; Liu et al. 2006). In a nice twist, survivin (one of the universal tumor associated antigens yielding peptides in this application) has recently been found to be exported to external environment via exosomes (Khan et al. 2010). Because of this distillation or selection of molecules to be exported that has occurred either during earlier stages of cancer evolution or progression toward malignancy, some proteins, RNA or lipids may only be seen after purification of the CDVs due to the removal of the overwhelming abundance of other material in whole cell lysates or even subcellular fractions (Valadi et al. 2007; Al-Nedawi et al. 2008; Skog et al. 2008; Chen et al. 2010; Nilsson et al 2009; Garcia et al. 2008; Hong et al. 2009). Accordingly, the enrichment or purification of HSP accessorized complexes such as CDVs (that may include exosomes, microvesicles, microparticles, apoptotic bodies or other allonyms) represents an opportunity to identify indices for cancer patient staging, monitoring, prognosis and suitability of individuals for treatment. Due to the relatively recent recognition of CDVs as a profound influence in health and disease, it is inevitable that any innovations that promote their reproducible and simple enrichment will create substantial interest in all fields of human and animal biology, particularly in expediting detection, characterization, treatment and monitoring of pathologies such as cancer.

(i) Diagnostics

HSPs bind basic hydrophobic peptides. In one embodiment of the present application, this characteristic is used herein along with affinity and counter electrophoresis methods to identify HSP binding proteins and peptides associated with a biological system of interest for direct analysis or the comparison of a disturbed, compromised or treated state, with a condition from the same system that more closely conforms to normalcy or standard (e.g. diseased vs. healthy, polluted vs. undisturbed, treated vs. non-treated, test vs. control).

In one manifestation of the application, counter HSP isoelectric focusing electrophoresis (CHIEF) is used herein directly to determine the binding capability of broad specificity binding molecules such as HSPs, or their clinically relevant interacting partners, with the peptides and/or polypeptides of the application. Isoelectric focusing (IEF) was used as the medium for counter-electrophoresis since it could be conducted from an analytic perspective on gels, while the option for preparative manipulation existed in high volume free solution systems (2-50 mL). The HSPs captured by the peptides and/or polypeptides of the present application during CHIEF included isoforms of HSP60, HSP70 and HSP90 as well as the non-canonical HSP, HSP27. The ease with which the formation of HSP complexes was achieved may prove more efficient and provide higher yields of target molecules for immunotherapy, or other suitable application, than contemporary methods such as nucleotide affinity chromatography or chemical cross-linking.

It was also found that an increase in energy accelerated the binding and improved binding of HSPs and the peptides and/or polypeptides of the application. Cytoplasmic proteins from a cancer cell line were subjected to a simple admixture with the polypeptides by microwave pulses at 42° C. and were compared to identical admixtures placed in a 42° C. heating block or at room temperature. Complexes of peptide-HSP and associated proteins were formed within 15 seconds of a microwave pulse of 42° C. However, in control experiments, similar complexes formed between 1-2 hours when incubated by heating block and after three hours when left at room temperature (~20° C.). Subsequently it was determined that overnight incubation at 4° C. was sufficient to produce HSP complexes. Therefore direct mixture and centrifugation can be used to capture HSP complexes using the polypeptides of the application.

It was then investigated whether the peptides and/or polypeptides of the present application could be used to capture HSPs directly from cancer cells. It was found that CHIEF captured multiple HSP family members using the polypeptides, the HSP family members being in association with a macromolecular complex of other proteins characteristic of the cancer proteome such as glycolytic enzymes, non-canonical chaperones and membrane proteins (as determined by mass spectrometry). The co-capture of multiple HSPs is of particular significance in that HSPs are known to optimize antigen processing: the captured complexes can include HSPs already loaded with cancer specific peptides and thus be valuable as immunotherapeutants. Of newly recognized significance, however, is that, because any proteins associated with HSPs in the context of cancer may be significant for a cancer cell's continued survival in the host, the present approach can be of extraordinary interest to proteomic discovery and profiling. In short, the polypeptides of the present application represent a means to harvest biomarkers of diagnostic and prognostic significance, as well as, novel targets for therapy.

The peptides and/or polypeptides of the present application were also used to bind constituents of vesicular material released by cancer cells to the surrounding environment. The vesicular material, variously referred to as exosomes or microvesicles, have recently been appreciated as a cellular function that has been co-opted from normal cellular physiology by cancer and accelerated to deliver coordinating proteins, RNA, lipids and metabolites. The vesicles are now recognised as vehicles that coordinate cellular function among cancer diaspora, negatively influence host immune response, or modulate phenotype of immediately adjacent host tissues or distal locations to facilitate metastasis. Reflecting the cancer cell membrane systems of origin, cancer cell vesicles are accessorised externally with a variety of HSPs. The enrichment of vesicles from complex dilute sources was of particular interest since material shed by cancer cells in vitro is considered the most likely source of undiscovered biomarkers in an artificial system. The overlap of the so-called "secretome" has been reported to be significantly higher when in vitro subcellular fractions are compared to material shed by cancer cells in vivo. Indeed, analysis of molecules present in biologically active vesicles may not be detectable in whole cell preparation due to the overwhelming presence of abundant molecules. Although in earlier stages of the application, unequivocal binding of the peptides could be demonstrated as counter ions to recombinant HSPs, the protrusion of basic and hydrophobic side chains of the basic alpha helix may assist in the association and insertion of the Vn peptides with the anionic bilayer membrane of the CDVs (Flechtner et al. 2006; Andreev et al. 2010; Bechinger B, 2010).

Furthermore, vesicular material shed by cancer cells into the patient, captured by a robust and simple method, would enable clinical analysis of cancer development, response to treatment, and monitoring via a non-invasive method (such as might be achieved by regularly scheduled blood sampling). Initial analysis involving cultured metastatic breast and prostate cancer cells confirmed the capability of the peptides and/or polypeptides of the present application to bind and facilitate the sedimentation of vesicular material from extracellular medium as determined by the immuno-detection of HSPs and glycolytic enzymes. The CDVs prepared by ultra-centrifugation were all—to varying degrees—HSP70 positive. Moreover, RNA analysis of the peptide and/or polypeptide sedimented vesicular material determined that mRNA of proteins over-expressed in cancer are preserved intact within the vesicular material. The range of possibilities for peptide utilization in cancer biology thus includes the capture of proteins and RNA species protected in extracellular material, with the potential for analysis by down-stream clinical methods such ELISA, Western blotting, mass spectrometry and qRT-PCR.

Therefore, the present application includes a method of fractionating one or more substances relevant for discovery, research or clinical analysis from a biological sample comprising: (a) contacting the biological sample with one or more of the peptides and/or polypeptides of the present application under conditions suitable for binding of the one or more peptides and/or polypeptides to the one or more substances to form complexes, and (b) fractionating the complexes.

In an embodiment of the present application the substances relevant for discovery, research or clinical analysis are proteins, for example, cancer-related proteins. In another embodiment one or more substances relevant for discovery, research or clinical analysis are cell derived vesicles (CDVs). In a further embodiment the CDVs contain a multitude of cancer-related proteins and/or nucleic acids.

In another embodiment, the cancer-related proteins are associated with HSPs which, while not oncoproteins per se, are imperative for the continued function of cancer proteins they are associated with. In a further embodiment the HSP is HSP60, HSP70, HSP90 or HSP27 or an isoform thereof.

A further aspect includes a method of fractionating one or more substances relevant for discovery, research or clinical analysis from a biological sample comprising: (a) contacting the biological sample with one or more of the peptide and/or polypeptides of the application under conditions suitable for binding of the one or more polypeptides to CDVs to form complexes, and (b) fractionating the complexes.

The CDVS contain for example heat shock proteins that allow for identifying substances in the CDVs relevant for disease research and/or clinical analysis. Accordingly, in an embodiment, the one or more substances relevant for discovery, research or clinical analysis are proteins, for example, cancer-related proteins or other molecules including for example nucleic acids such as RNA, miRNA, large intergenic non-coding RNAs (lincRNAs), as well as other molecules such as linear and branched polysaccharides, which are comprised in the complexes.

The disease proteins can be for example associated with HSP either directly or through associated pathways and/or from other from CDVs.

In another embodiment of the present application, the biological sample is a bodily fluid, such as blood, plasma, urine, cerebrospinal fluid, lymph, ascites, saliva, lavage, semen, glandular secretions, feces, exudate, contents of cysts or other sources.

In an embodiment, the "conditions suitable for binding of the one or more polypeptides to the one or more substances to form complexes" comprise counter affinity isoelectric focusing. In a further embodiment, the "conditions suitable for binding of the one or more polypeptides to the one or more substances to form complexes" comprise contacting solutions of the one or more peptides with the biological sample in a biologically relevant solution and applying agitation, heat and/or microwaves.

In an embodiment of the application, fractionation is performed by sedimentation. In another embodiment, the one or more peptides and/or polypeptides are attached to a solid support and fractionation is performed using methods specific to the solid supports, for example, when the solid support is a magnetic bead (e.g. Dynal™ beads from Invitrogen), fractionation is performed by collection of the beads using a magnetic source.

Alternatively the peptides and/or polypeptides of the present application may be mixed and incubated with agitation at temperatures predicated by final application. Incubations may be conducted with detergents or other molecules that prevent non-specific binding. Following the sedimentation of peptide- and/or polypeptide-affinity enriched HACs, including CDV preparations, the resulting material may be further washed with a variety of detergent or chaotropic reagents in an protocol-determined gradient of stringency (for example where saline would be considered a mild wash, and stringent washing solutions would include SDS or urea).

Cell derived vesicles (CDVs) are normally used as vehicles for intercellular communication without the necessity for direct contact. However excessive vesicle release into the surrounding environment is a common feature of tumor cells. Capture of CDVs from the extra cellular matrix is regarded as an important source of potential biomarkers, since proteins secreted by cancer cells may reflect the closest facsimile of biological interface between the cancer and the surrounding host tissue environment of the patient. Capture of vesicles from plasma and other body fluids is also regarded as highly significant in that the encapsulated material represents a source of biologic materials otherwise inaccessible by contemporary methods. Molecules associated with vesicles may thus permit informed decisions regarding the earlier staging of cancer patients, treatment, monitoring and recurrence free survival. Peptides and/or polypeptide capture of vesicular material may thus facilitate clinical analysis by microarray and qRT-PCR. Therefore, in a specific embodiment, the present application also includes a method of diagnosing an infectious, disease such as a parasitic disease or cancer in a subject comprising: (a) contacting a sample from the subject with one or more peptides of the application and/or one or more polypeptides of the application under conditions suitable for the binding of the of the one or more peptides or polypeptides to one or more infectious disease and/or cancer relevant substances to form complexes, (b) fractionating the complexes, and (c) detecting the presence of the one or more infectious disease and/or cancer relevant substances in the complexes, wherein the presence of the one or more infectious disease and/or cancer relevant substances is indicative of the diagnosis of the cancer or infectious disease. In an embodiment the presence of the one or more infectious disease and/or cancer relevant substances is compared to control samples, for example samples from a same system that more closely conforms to normalcy or standard (e.g. diseased vs. healthy, polluted vs. undisturbed, treated vs. non-treated).

(ii) Therapeutics

When the peptides of the present application were included in the extracellular medium of the cancer cell lines (at concentrations of 7-25 μg/mL) such as PC3 (prostate cancer) and MCF7 (breast cancer), there was an inhibition of the protein synthesis and cell lysis within 24 hours. This observation suggests that the peptides and/or polypeptides of the present application may inhibit the support function for oncoproteins provided by competitive inhibition for HSPs. Administration of the peptides and/or polypeptides may therefore have resulted in degradation of oncoproteins and reduced signaling capability imperative for cancer survival. Since all major cancer causing species rely upon scaffolding by HSPs for stability and function, the peptides may represent a source of direct therapeutic application.

In HSP augmented immunotherapy, previous attempts have resulted in increased immune cell activity in vitro, but have failed to translate into recurrence free survival. Administration of the peptides and/or polypeptides of the application may circumvent earlier shortcomings caused by availability of vaccine material or poor epitope coverage enabling immune escape. Peptides and/or polypeptides of the present application can be synthesised to include single or multiple disease epitopes.

Therefore, the present application further includes a method of inducing an immune response and/or treating cancer comprising administering an effective amount of one or more of: the peptides or polypeptides of the application to a subject in need thereof.

A further aspect includes a method of inducing an immune response and/or treating cancer comprising administering an effective amount of one or more of the peptides, polypeptides, complex, nucleic acid and/or the agent described herein to a subject in need thereof.

It was determined that a lyophilized preparation of the innocuous mycobacterial relative *Arthrobacter davidanieli* (known to generously express HSP70 and HSP60 at the cell surface) could be reconstituted in buffer containing the peptides and/or polypeptides of the application. Following overnight incubation at 4° C., it was determined that the peptides and/or polypeptides were stably bound to the cell surface of *A. davidanieli*, resisting washing with the membrane disrupting detergent Triton X-100. These observations suggest that is possible to extend the utility of immunomodulatory bacteria by accessorizing and thereby increasing immune response to selected tumor associated antigens or indeed any other compatible peptide of interest comprised in the polypeptides of the application, to in vitro or in vivo research, discovery of clinical application. In this manner the bacteria, already approved for use as a live vaccine in human food products (Atlantic salmon), would act as an immunostimulatory vehicle coated with polypeptide(s) representing any key protein(s) of cancer or infectious disease.

(IV) EXAMPLES

The following Examples are set forth to aid in the understanding of the application, and are not intended and should not be construed to limit in any way the application set forth in the claims which follow thereafter.

All peptides were prepared at New England Peptide (Gardner Mass.) using solid-phase peptide synthesis to synthetically produce peptides (Sabatino et al. 2008).

Example 1

Corynebacterial HSP70 Binding to Basic Proteins

*Arthrobacter davidanieli* (Accession No ATCC 55921) is a bacterium isolated from cultured Chinook salmon brain as a co-culture to *Renibacterium salmoninarum*. The bacterium was determined to be closely related to a salmon pathogen, *Renibacterium salmoninarum*, the etiologic agent of bacterial kidney disease (BKD), although not a disease agent in its own right (Wiens et al 2008). When used as a live suspension reconstituted in saline, *A. davidanieli* provided significant protection against BKD in both laboratory and field trials (Griffiths and Salonius 2005, U.S. Pat. No. 6,913,754). It was later determined that *A. davidanieli* also provided protection against an unrelated pathogen *Piscirickettsia salmonis* (Salonius and Griffiths 2007 U.S. Pat. No. 7,302,913).

*A. davidanieli* was examined, with emphasis placed on cell surface molecules that might contribute to multivalent protection against taxonomically disparate pathogens. SDS-PAGE analysis of *A. davidanieli* cell surface extracts identified two major proteins between 50 and 75 kDa molecular weight. The proteins were only weakly observed when bacteria were washed in phosphate buffered saline containing digitonin. However, the proteins were observed as major bands when the bacteria were washed with buffers of greater stringency (such as containing Triton X-100 or SDS). Following SDS-PAGE, resolved proteins were blotted to PVDF and submitted for N-terminal amino acid sequencing (Midwest Analytical, St Louis Mo.). The first 15 amino acids of the first major band were found to be identical to that of *R. salmoninarum* and *Mycobacterium tuberculosis* HSP70. The second major protein was determined to be HSP60, with a similar extensive homology to orthologues expressed by the same corynebacterial species. The HSP60 and HSP70 genes were subsequently sequenced and recombinant versions expressed in *E. coli* (Griffiths et al. 2007, U.S. Pat. No. 7,297,783; Griffiths et al 2010, U.S. Pat. No. 7,674,892).

The identification of a rich source of corynebacterial HSP70 and HSP60 prompted further inquiry into immunomodulatory properties. Many literature citations existed for the considerable immunomodulatory potential afforded by mycobacterial HSP70 when complexed with protein fragments or peptides (e.g. see Huang et al 2000). *A. davidanieli* HSP70 was convenient because it was simple to cultivate and innocuous enough to receive licensing approval as a live vaccine for fish intended for human consumption from Canadian Food Inspection Agency (Ottawa, ON).

Traditionally, preparation of HSP70-peptide complexes is achieved by nucleotide affinity purification (chromatography) or via the genetic engineering of chimeric recombinant proteins (e.g. Li et al. 2008). Contemporary approaches appeared prohibitively costly or inefficient for high volume preparation and flexibility. Accordingly alternative methods were considered.

Given the promiscuous affinity of HSP70 for sequences containing hydrophobic and basic amino acids, isoelectric focusing (IEF) was considered as method by which corynebacterial HSP70 could interact with peptides by positioning them to migrate into one another as counter ions. During migration, converging wave fronts of prospective binding partners would serve to force molecules to associate with one another "face to face". IEF would also provide for the departure of unbound material that might include modulators such as nucleotides. IEF titration could be conducted by gel, while scaled up production could be achieved by preparative or free solution IEF.

To validate the counter HSP IEF (CHIEF) concept, it was determined that recombinant *A. davidanieli* HSP70 (adHSP70) focused at an isoelectric point (pI) between 4.5 and 5.0. A highly basic protein was required as a counter ion. Bovine myelin basic protein (bMBP), pI 11.0, was provided by Dr. Bruce Allen (see Chevalier and Allen 2000). Given that HSP70 was a major surface protein of *A. davidanieli*, buffers containing digitonin and Triton-X 100 detergent were used to prepare cell surface extracts for running adjacent to recombinant adHSP70. As shown in FIG. 1, adHSP70 whether in cell extracts or as recombinant preparation, bound bMBP at a pI midway between those of uncomplexed counter migrants (~pI 6.5 marker; FIG. 1, lane 1). adHSP70 did not interact with recombinant carbonic anhydrase, myoglobin or trypsinogen but did bind to another basic protein lysozyme. Recombinant *Mycobacterium tuberculosis* HSP70 (Aalto, Eire) also complexed with basic proteins such as bMBP and lysozyme, corroborating the similarity between Arthrobacterial and Mycobacterial orthologues. However, similar complexes were not formed with recombinant mammalian HSP70 or the *E. coli* orthologue, dnaK.

Example 2

Counter Migration of Corynebacterial HSP70 with Cancer Cell Nucleus Proteins

Figure 2:
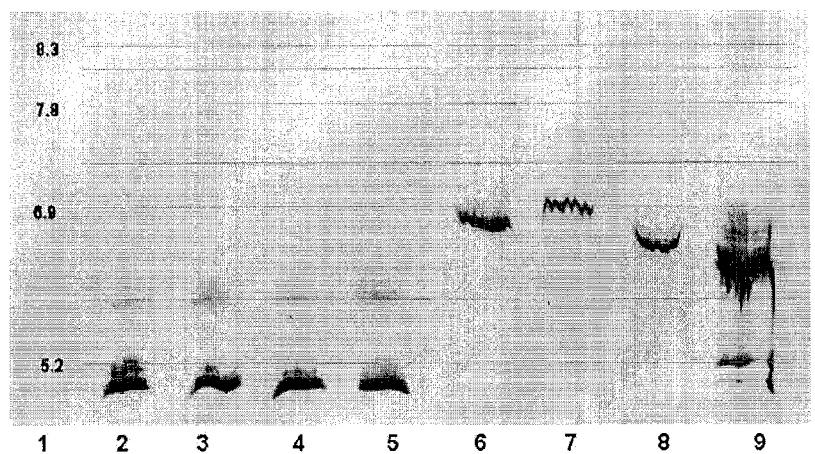
FIG. 2 shows CHIEF of recombinant A. davidanieli HSP70 with membrane-associated or nuclear proteins from cancer cells. Lane 1: isoelectric point (pI) standards. Lanes 2, 3, 4 and 5: membrane proteins from cell lines Raji, Nalm-6 MCF-7 and TA respectively counter migrating against 2 µg of recombinant AdHSP70. Lanes 6, 7, 8 and 9: 20 g of nuclear proteins from cell lines Raji, Nalm-6 MCF-7 and TA respectively counter migrating against 2 µg of recombinant AdHSP70.

Corynebacterial HSP70 was exposed to a more comprehensive collection of potential basic ligands. The eukaryotic nuclear proteome was regarded as a source of basic ligands due to the requirement for interaction with nucleic acids. It was determined, by preparative IEF, that the majority of proteins present in the nuclear fraction of leukemic and breast cancer cell lines have a pI greater than 9. Breast cancer and leukemia cell lines were prepared to yield fractions enriched with membrane associated or nuclear proteins. Fractions were standardized to 20 µg by bicinchoninic acid (BCA) assay for anodal application and counter migration against 2 µg of recombinant adHSP70 applied at the cathode. In anticipation that complexes of adHSP70 and proteins from the cancer nucleus might be difficult to observe by conventional staining (Coomassie Blue), the gel was blotted to nitrocellulose and probed with rabbit antiserum raised against the recombinant adHSP70 (New England Peptide, Gardner, Mass.). As shown in FIG. 2, immunoreactivity was chiefly restricted to adHSP70 that had migrated directly to the cathode, focusing without interference from counter migrating membrane proteins (lanes 2 to 5). In contrast, when nuclear proteins served as counter ions, immunoreactivity was generally restricted to a position close to pI standard 6.6. Some indication of minor bands was observed in lane 9 representing the nuclear proteins of the immortalized but non-transformed B-cell line TA.

Example 3

Identity of Nuclear Proteins forming Complexes with Corynebacterial HSP70

Figure 3:
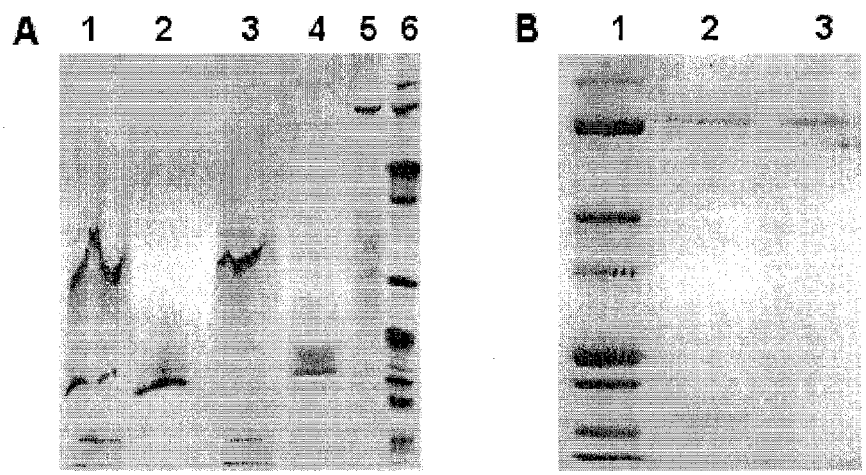
FIG. 3 shows CHIEF of corynebacterial HSP70 with nuclear proteins and disruption for identification of ligand by mass spectrometry. Gel A Lanes 1-5: 10 µg of nuclear proteins were applied at the anode end of the IEF gel. In lanes 1 and 2, 3 µg of recombinant M. tuberculosis HSP70 were placed as counter migrants at the cathode; in lanes 3 and 4, 3 µg of recombinant A. davidanieli HSP70. Lane 6: isoelectric point standards. Gel B CHIEF complex in Gel A, lane 3 and uncontested HSP70 in Gel A lane 4 were excised by scalpel and heated in Laemmli buffer. Lane 2 Laemmli buffer supernatant from CHIEF complex excised from Gel A lane 3. Lane 3: Laemmli buffer supernatant from uncontested HSP70 excised from Gel A lane 4. Lane 1: molecular weight standards.

To confirm that the formation of CHIEF complexes with nuclear proteins was not solely restricted to the HSP70 of *A. davidanieli*, CHIEF was conducted with recombinant HSP70 from *M. tuberculosis*. In FIG. 3A, the coomassie blue stained gel demonstrates that *A. davidanieli* and *M. tuberculosis* yield similar mid-gel complexes with counter migrating nuclear proteins from the B-cell line TA. The complex was excised from the gel, minced and boiled in Laemmli buffer. The resulting mixture was centrifuged and the supernatant applied to second dimension separation by sodium dodecyl sulphate polyacrylamide gel electrophoresis (SDS-PAGE). The resulting gel was stained with coomassie blue (FIG. 3B). A band migrating near to the 75 kDa molecular weight marker was observed in the lane containing material originating from uncontested HSP70 as well as the lane containing material originating from the complex formed during counter migration with nuclear proteins. However, two additional bands were identifiable near the 15 kDa molecular weight marker in material originating from HSP70 and nuclear protein interaction (FIG. 3B, lane 3). Mass spectrometry analysis determined that bands corresponded to histone 2A and histone 2B. Recombinant histone 2A (Sigma Aldrich) yielded an identical complex when used as a counter ion to adHSP70.

Example 4

Identification of Corynebacterial HSP70 Compatible Amino Acid Sequences Within bMBP The unequivocal binding of bMBP with adHSP70 suggested the existence of peptide sequences within bMBP that might be used to facilitate the binding of immunologically relevant antigens to HSPs. The amino acid sequence of bMBP was screened for candidate non-pathogenic polypeptides between 15 and 25 residues long, exhibiting criteria for potential HSP70 binding polypeptides: The inclusion of hydrophobic and basic amino acids with the central positioning of hydrophobic residues, avoiding acidic residues but permitting flanking basic and aromatic residues.

Figure 4:
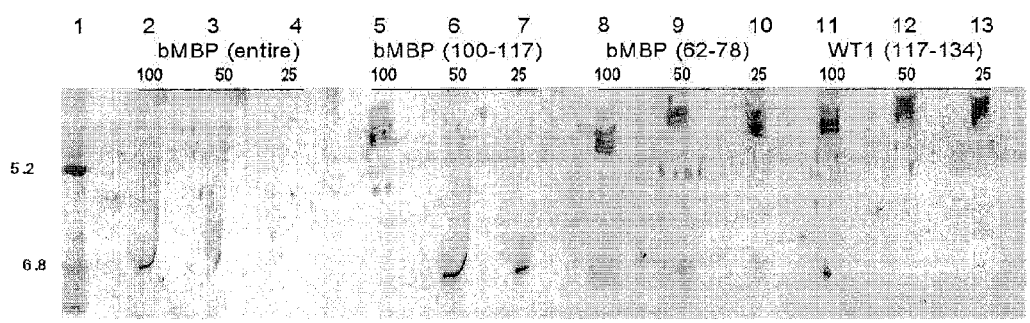
FIG. 4 shows CHIEF of MBP 62-78 and MBP 100-117 with *Arthrobacter davidanieli* HSP70. Comparison of CHIEF binding with bovine myelin basic protein (MBP) and two candidate binding peptides with 2 µg of adHSP70. Lanes 2-4: binding of 100, 50 and 25 µg of MBP with adHSP70. Lanes 5-6: binding of 100, 50 and 25 µg of MBP peptide 100-117. Lanes 8-10: negligible binding of 100, 50 and 25 µg of MBP 62-78. Lanes 11-12: no evidence of binding with WT1 117-134 peptide. Lane 1 contained pI standards. Note that at high concentrations of MBP 100-117 (100 µg, lane 5), the peptide appears to inhibit complex formation with adHSP70.

Three peptide candidates were chosen but only one of these, 100-117, produced counter ion complexes with adHSP70 and mtHSP70 (FIG. 4).

Example 5

Reactivity of bMBP100-117 with Non-Bacterial HSP70

Figure 5:
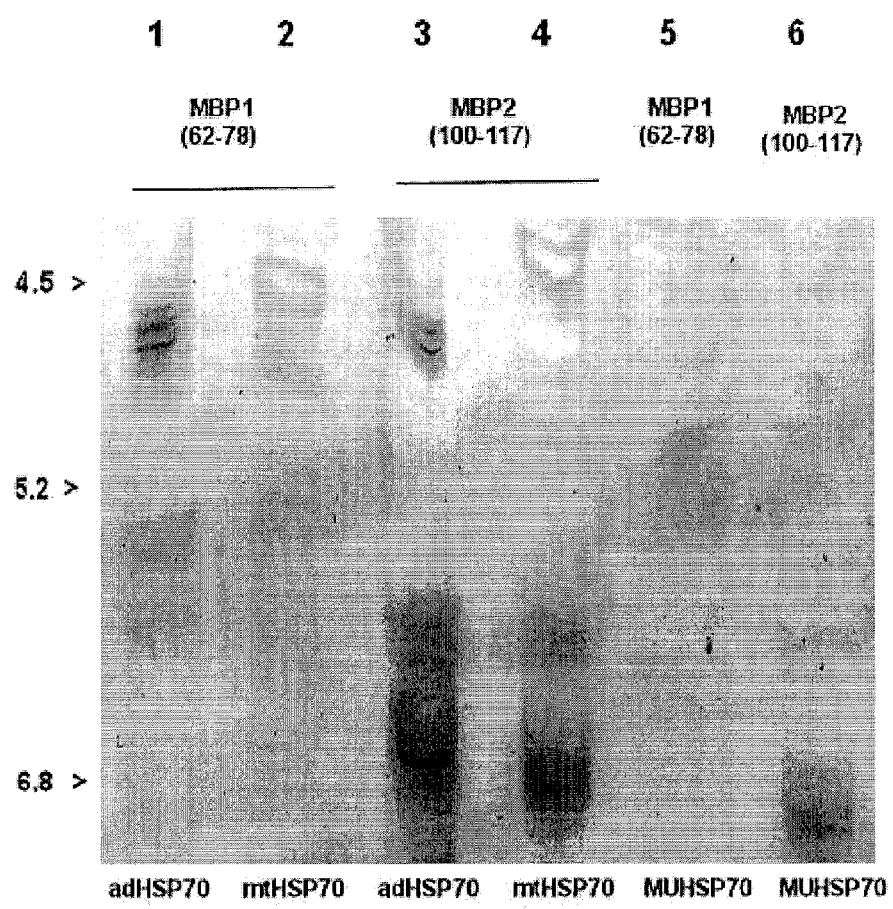
FIG. 5 shows CHIEF of peptide MBP 100-117 with corynebacterial and murine HSP70. Silver stained CHIEF gel in which MBP peptides 1 (62-78) and MBP 2 (100-117) were placed as counter migrants opposite adHSP70 (lanes 1 and 3), mtHSP70 (lanes 2 and 4) and murine HSP70 (lanes 5 and 6). Focusing positions of pI standards are indicated on the left hand side of the figure. The HSP peptide complex is seen as a dark smudge near the pI 6.8 marker. Silver stain was used due to poor staining of murine HSP70 by Coomassie blue (Note: silver staining has caused negative staining of the *M. tuberculosis* band near pI 4.5 (lanes 2 and 4)).

Given that bMBP 100-117 yielded complexes when used as a counter ion for corynebacterial HSP70, compatibility of the polypeptide for HSP70 from other species was investigated. Recombinant murine HSP70 was placed as counter migrant to 40 µg of MBP100-117 and compared to recombinant *A. davidanieli* and *M. tuberculosis* HSP70 (FIG. 5). In contrast to the whole protein, the 18 mer peptide complexed with mammalian HSP70 (FIG. 5 lanes 3, 4 and 6).

Example 6

Modification of bMBP100-117 by Addition of Flanking Regions of Disease Associated Peptides This example examines the possibility that the MBP100-117 peptide can facilitate binding of epitopes to HSPs when appropriate amino acid sequences are co-synthesized as flanking peptides. For example cancer associated peptides can be synthesized as flanking regions for the bMBP 100-117. The choice of epitope can be predicated by MHC compatibility or the prior identification of dominant proteins in a patient's cancer by histopathology or immunoassay. The HSP-bMBP-disease peptide complexes can then be prepared by counter ion electrophoresis in the manner described above.

By stable association with HSP, the disease peptide flanking the core HSP affinity region might be rendered more immunogenic. The strategy of combining drug-induced apoptosis of cancer cells (which renders them more immunogenic) with immunotherapy targeted against specific TAAs is currently considered one of the more promising possibilities for the combinatorial therapy of cancer (e.g. Spisek and Dhodapakar 2007; Andersen et al 2008). The preparation of MBP100-117 peptide cocktails might thus enhance immunogenicity through association with HSP family members while also simultaneously reducing the possibility of immune escape through the provision of multiple epitopes of one or more TAAs (immune escape is a prevalent feature of aggressive tumors: Dunn et al 2002). It is now well established that tumor cells express antigens that can be recognized by the host's immune system. Many antigenic peptides, which can be recognized by cytotoxic T-lymphocytes (CTLs), have been identified. Most clinical trials did not demonstrate sufficient anti-tumor clinical responses. Thus, it is now regarded that strategies are required to augment peptide-based immunotherapy in order to induce sufficient clinical responses that translate into improved survival in animal models and patients. The HSP-TAA peptide complexes prepared by CHIEF might prove useful for this purpose.

Tumor associated antigens (TAAs) were considered as a source of immunomodulatory epitopes. Of particular value to cancer immunotherapy are proteins that are not normally expressed in adult tissues but are upregulated in a variety of neoplasia to increase transcription or block apoptosis. Consistent with these criteria Wilms Tumor protein 1 (WT1) and Survivin (SVV) were chosen for further investigation.

WT1 is a transcription factor whose expression has been suggested to be vital for breast cancer, especially those of an aggressive phenotype (Tuna et al 2005). It is expressed in a broad variety of malignancies, indicating promise for broad immunotherapeutic application, especially since WT1 has been shown to be highly immunogenic in cancer patients. Strategies for further improvements might include combination with HSP in the manner described above. Various peptides from within the protein have been investigated for their property of stimulating anti-cancer immune responses.

SVV is aberrantly expressed in various cancer cells but is undetectable in normal differentiated adult tissues, with the exception of the testis, thymus and placenta. The protein, an inhibitor of apoptosis (IAP), is specifically up-regulated in breast tumors with poor prognosis. Survivin ranked 18th of the top 100 genes associated with poor prognosis in the supervised reanalysis (Brennan et al 2008; Rexhepaj et al 2010). Similar to WT1, given the universality of its up-regulation in tumors, the amino acid sequence of SW (~16.5 kDa) has been rigourously investigated for peptides that might prove useful for immunotherapy. The sequence has also yielded therapeutic peptides such as shepherdin (SW 79-87; later shortened to hexapeptide 79-83) that interfere with HSP90 folding of cancer proteins (Gyurkocza et al 2006[1]). Also similar to WT1, immune responses against the SW protein have been detected in cancer patients. For example, strong frequent CTL responses were detected against various SVVpeptides in cancer patients of different origin (Reker et al 2004). The criteria for the peptides chosen to flank bMBP 100-117 were compatibility with the major histocompatibility proteins class I and a basic isoelectric point (pI). A 23 amino acid peptide, 117-139, contain epitopes known to facilitate the killing of WT1 expressing murine and human cancer cells through both CTL and helper T-cell stimulating epitopes (Oka et al 2004). WT1 117-139 is identical in both human and murine WT1 orthologues. In vitro efficacy of killing cancer cells did not translate to increased survival of the mouse model of prostate cancer. The authors suggested the lack of prolonged survival might be due to insufficient immune response. One possibility to increase efficacy might be the delivery of the peptide in association with HSP70 via co-synthesis with bMBP100-117. Intriguingly, when an epitope from within the WT1 23-mer peptide (126-134) was injected at the same site as an injection of mycobacterial BCG cell wall skeleton (CWS), there followed a rejection of WT1 leukemia or lung cancer cells (Nakajima et al 2004). This further corroborates the potential use as an adjuvant for products derived from innocuous relatives of *Mycobacteria* such as *A. davidanieli*. It has been found that whole cells of *A. davidanieli* will strongly bind basic polypeptides by admixture.

Three peptides were chosen from the SW sequence for C-terminal co-synthesis with the MBP100-117 peptide. These included the aforementioned SVV20-28 in addition to SVV96-104. The 96-104 sequence, included in the adjuvant Montanide, provided the first successful demonstration of SVV based vaccination in a clinical setting (Wobser et al 2006). An uninvestigated sequence from SVV isoform 3, (88-96) was also chosen because isoform 3 had been shown to have a marked decrease in anti-apoptotic effects in comparison to the wild-type (Mahotka, et al 1999). These were considered as possibly augmenting complex formation when co-synthesised at the C-terminus of MBP100-117.

Figure 6:
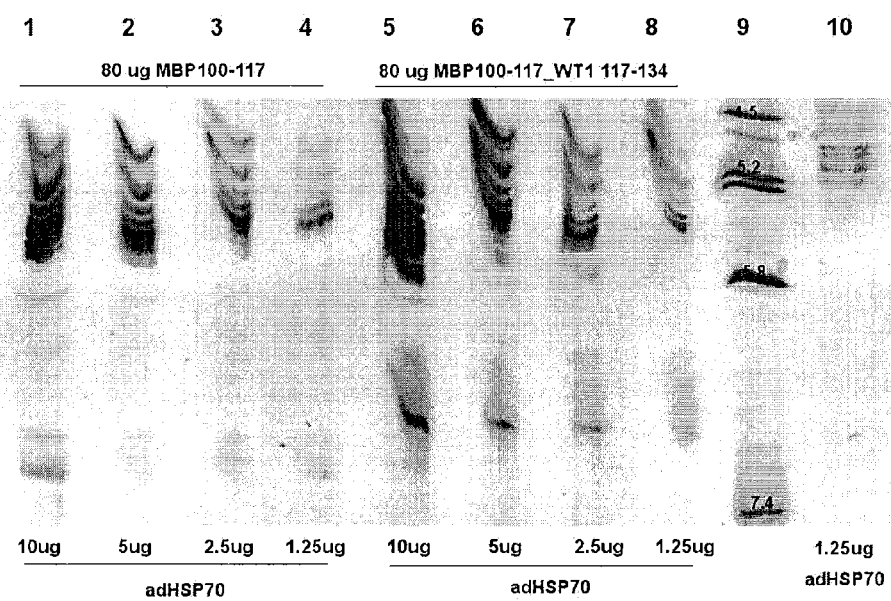
FIG. 6 shows CHIEF of MBP 100-117 and MBP 100-117_WT1 117-134 with *Arthrobacter davidanieli* HSP70. 80 µg of peptide MBP100-117 (lanes 1-4 or MBP100-117_WT1 117-134 (lanes 5-8) were applied to the anode of a 3.5-9.5 precast IEF gel. A range of adHSP70 concentrations were placed in direct opposition: 10 µg in lanes 1 and 5; 5 µg in lanes 2 and 6; 2.5 µg in lanes 3 and 7; 1.25 µg in lanes 4, 8 and 10. Isoelectric point standards are shown in lane 9.

Compared to MBP100-117, counter migration of the MBPWT1 against adHSP70 appeared to augment the formation of the complex formed ~pI 6.8 (FIG. 6).

Figure 7:
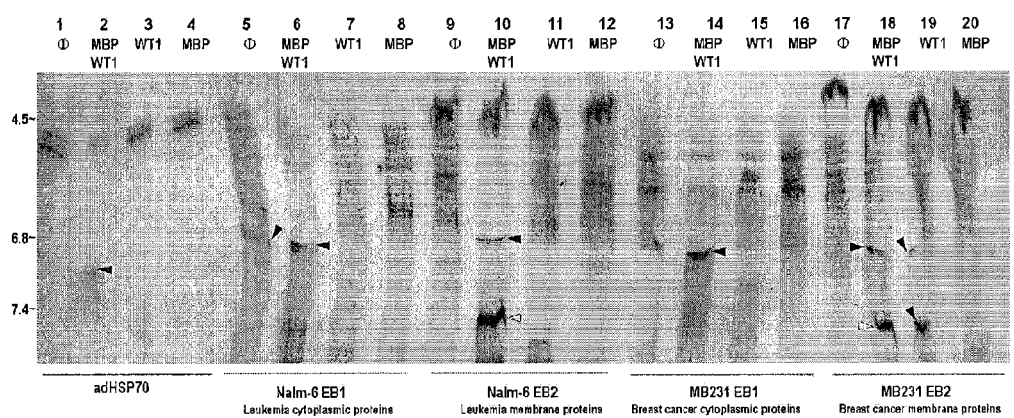
FIG. 7 shows CHIEF of MBP 100-117 and MBP 100-117$_{13}$ WT117-134 with *Arthrobacter davidanieli* HSP70 and subcellular fractions from an acute lymphoblastic leukemia cell line (Nalm-6) and a breast cancer cell line (MDA MB231). Abbreviations: φ=No peptide added at anode; MBPWT1, MBP100-117_WT1 117-134; MBP, MBP100-117; WT1, WT1 117-134. All peptides applied at cathode at a concentration of 80 µg (sic); subcellular fractions applied at cathode at a concentration of 10 µg. The arrowheads in lanes 2, 6, 10 (top), 14 and 18 (top) indicate expected CHIEF complex focusing near the 6.8 pI marker. The arrowheads in lanes 10 (bottom) and 18 (bottom) indicate the appearance of a CHIEF complex focusing near the 7.4 pI marker. The arrowheads in lane 5 and 19 (top and bottom) indicate where there has been cross over of the MBP117-134WT1 peptide into an adjacent lane causing a drive-by or swipe CHIEF complex formation (lane 5, lane 19).

Example 7 bMBP-TAA Polypeptides Forming Complexes when Used as Counterions for Cancer Cell Lysates The example investigates the possibility that the bMBPWT1 peptide binds HSPs directly from cell lysates in a similar manner to when single recombinant HSP was used as a counter ion. Cancer cells are addicted to the overexpression of HSPs to support growth under poor environmental conditions, to facilitate the function of otherwise unstable oncoproteins and the ablation of apoptosis. Most, if not all, cancer cells should provide a rich source of human HSPs to serve as complex forming counter migrants for the MBP peptide co-synthesised with WT1 and SW peptides. To investigate this possibility, subcellular fractions enriched in cytoplasmic proteins (extraction buffer 1) and membrane associated proteins (extraction buffer 2) were prepared from a leukemia cell line, Nalm-6, and a breast cancer cell line, MDA MB231 (FIG. 7). The individual MBP and WT1 peptides were also included as potential counter migrants.

Similar to the results observed in FIG. 6, the MBP peptide yielded a far more limited complex formation with adHSP70 when compared to MBPWT1. The WT1 counter migrant showed limited complex formation but was not as effective at combining with, and depleting, the adHSP70 when WT1 was co-synthesized with MBP (FIG. 7, lane 2, arrowhead). Cytoplasmic proteins from the leukemic and breast cancer cell lines yielded similar CHIEF complexes to that seen during the counter migration of recombinant adHSP70 and MBPWT1 (arrowheads, FIG. 7, lanes 2, 6 and 14). However using the membrane associated cell fractions from either cell line, a more cathodal complex focused closer to the 7.4 pI marker (bottom arrowheads FIG. 7, lanes 10 and 18). A "drive-by" or "swipe" effect of counter migrant complex formation was also observed in lanes in which cell proteins were focused in the presence of counter migrants expected to have reduced binding capacity, but adjacent to lanes in which MBPWT1 was being run (e.g. MBP and WT1 as individual counter ions or in the absence of peptide, lane 5). These effects were seen in future experiments where application points for counter migrating HSP source and cationic peptides were not completely aligned or inconsistencies in IEF gel rehydration had occurred.

In summary the MBP100-117 peptide, co-synthesized with amino acid sequences, such as WT1, yielded complexes in two distinct subcellular fractions from two discrete cancer cell lines.

Example 8

Figure 8:
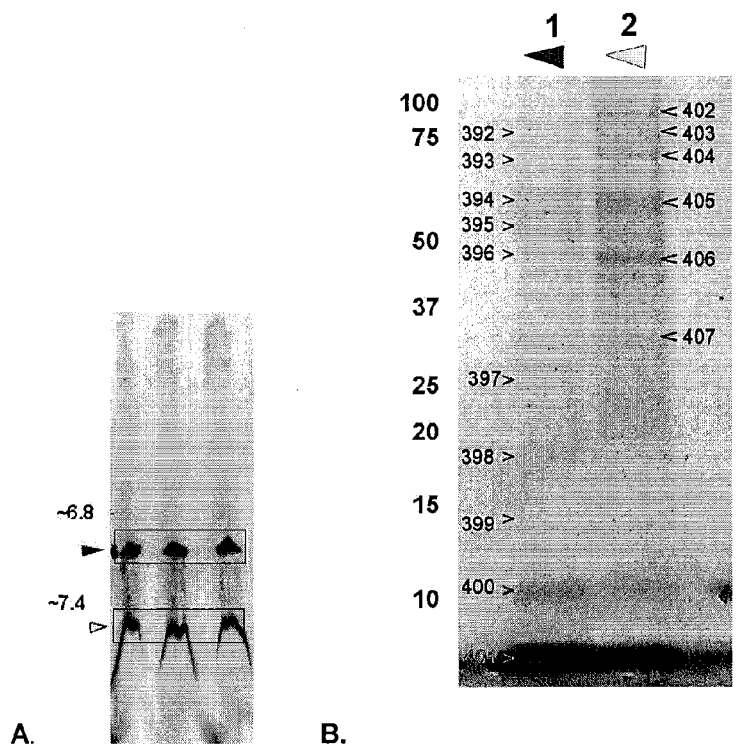
FIG. 8a shows CHIEF gel used to generate second dimension SDS-PAGE profile for mass spectrometry analysis. Three identical lanes were prepared for the generation of CHIEF complexes between MBP100-117WT1 117-134 (80 µg) and 10 µg of Nalm-6 membrane associated proteins.
FIG. 8b shows the second dimension SDS-PAGE of CHIEF complexes excised from gel of counter migrating MBP100-117WT1-134 and membrane associated proteins of leukemic cell line Nalm-6.

Mass Spectrometry Analysis of Complexes Formed between bMBPWT1 as Counter Migrant for Leukemic Cell Proteins Bands representing counter migrant complexes typical of the pI ~6.8 and pI ~7.4 observed in FIG. 7 were excised by scalpel. The gel pieces were boiled in Laemmli buffer and resolved by SDS-PAGE (FIG. 8 a-b). In the manner previously described for the detection of proteins binding to corynebacterial HSP70, it was anticipated that binding partners of the bMBPWT1 peptide would become denatured and migrate into the SDS-PAGE gel. However rather than two bands, a more complex profile of dissociated bands was observed (FIG. 8b). The resulting gel was sent to McGill Proteomics Facility (Genome Quebec) where a selection of bands were excised and processed for protein identity by mass spectrometry. The counter migrant complex focusing near 6.8 was found to contain HSP90, HSP60, calreticulin, 14-3-3 zeta and calmodulin. The counter migrant complex focusing near the pI 7.4 contained HSP90 (both cytoplasmic and gp96 isoforms), and at least 20 other proteins that were not heat shock proteins.

In summary this data represented the first occasion that complexes formed when the peptides were used as counterions against cancer cell proteins.

Example 9

Comparison of bMBPTAA Peptide/Cancer Cell Protein Counter Migrant Complexes with that Produced by a Published Peptide Sequence The reactivity of the MBPWT1 was compared to a previously reported sequence determined to be compatible with HSP70, the peptide JVL2 (Flechtner et al 2006). JVL2 was co-synthesized with the WT1 peptide sequence. Additionally it was determined if the MBPWT1 would bind to recombinant HSP70 from other species and the ER isoform, GRP78. GRP78 is frequently over expressed in cancer cells and appears at the cell surface (Liu et al 2007; Whitaker et al 2007; Kelber et al 2009; Misra et al 2009).

The MBPWT1 peptide was also positioned on IEF gel as counter migrant to recombinant HSP90 isoforms: cytoplasmic recombinant human HSP90 and, the ER isoforms glycoprotein 96 (gp96; canine). Various isoforms of HSP90 are universally over expressed in cancer cells and aberrantly exposed on the exterior surface of cancer cells membranes (Tsutsumi and Neckers 2007; Tsutsumi et al 2008; Sidera and Patsavoudi 2008 a, b). HSP90 bound peptides, particularly of the gp96 isoform have for two decades been identified as carriers of immunogenic peptides of powerful in vitro modulation and encouraging clinical trials. However successful application to patients appears to be predicated by amount of starting material available.

Figure 9:
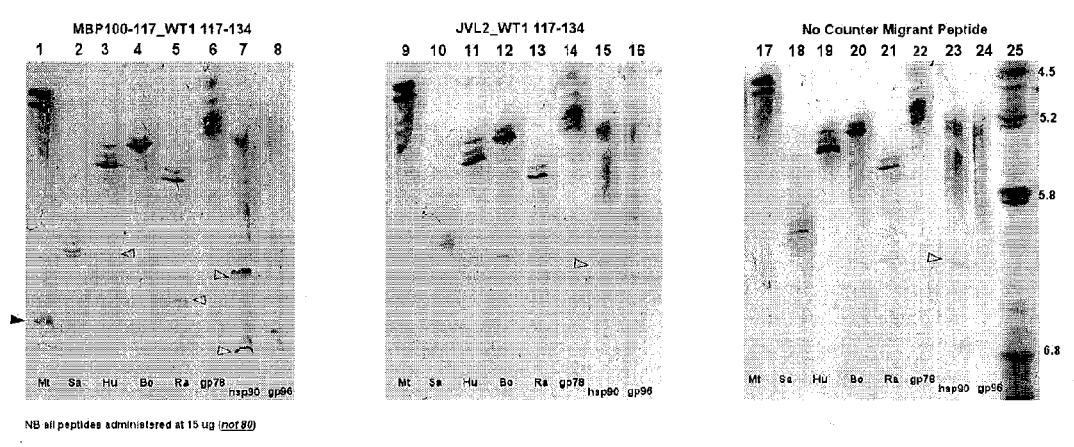
FIG. 9 shows MBP 100-117WT1 117-134 as IEF counter migrant to isoforms of recombinant HSP70 and HSP90. 1 µg of recombinant HSP70s were placed opposite 15 µg MBP peptide 100-117 co-synthesised with Wilms tumor protein 1 peptide 117-134 as indicated on the figure. Mt (lanes 1, 9 and 17) *Mycobacterium tuberculosis*; Sa (lanes 2, 10 and 18) Chinook salmon; Hu (lanes 3, 11 and 19) human; Bo (lanes 4, 12 and 20) cow; Ra (lanes 5, 13 and 21) rat; gp78 (lanes 6, 14 and 22) hamster HSP70-5, endoplasmic reticulum isoforms of HSP70; hsp90 (lanes7, 15 and 23) human recombinant heat shock protein 90; gp96 (lanes 8, 16 and 24) canine glycoprotein 96 endoplasmic reticulum isoform of HSP90. pI standards are in lane 25. Counter migrant peptides are MBP100-117 in lanes 1-8, Javelin 2 peptide co-synthesised with WT1 peptide 117-134 in lanes 9-16. No counter migrant peptides were applied at the anode in lanes 17-25. Binding with recombinant HSP90 confirmed corroborating result seen in mass spectrometry of SDS-PAGE separated complexes from leukemic cell line Nalm-6.

As previously observed, a counter migrant complex formed between *Mycobacteria* HSP70 and the MBP peptide (FIG. 9, lane 1, arrowhead). A complex was only weakly observed when JVL2 was used (lane 9) and absent in the uncontested mtHSP70 (lane 17). Some evidence of counter migrant complex formation was also seen between MBPWT1 peptide and human HSP70 (lane 3, arrowhead) and rat HSP70 (lane 5, arrowhead). The MBPWT1 peptide produced complexes when used as a counter migrant to HSP90 and the ER isoform gp96 (lanes 7 and 8). One of these complexes (lane 7, top arrowhead) appeared to be in the same position as a weakly staining band arising from uncontested HSP90 (lane 23). However the more cationic protein band (Lane 7, bottom arrowhead) was not present when the counter migrant peptide was JVL2WT1 or when HSP90 were applied to the IEF gel without counter ions (lane 23).

The identification of a counter migration complex forming between HSP90 isoforms and MBPWT1 corroborated the identification of HSP90 in mass spectrometry (Example 8). The affinity of the peptides for HSP90 indicated the possibility for simultaneous capture or inhibition of cancer proteins dependent upon HSP90 for survival and metastasis including c-KIT, HER2, VEGF, RAF AKT, HIFα among many others, for example via their HSP associated complexes (HACs) with these proteins.

Example 10

MBPTAA peptides as Counter Ions to SKBR3 Cytoplasmic Proteins

At concentrations below 80 μg, the MBPWT1 peptide occasionally produced only modest complexes with Nalm-6 proteins. MBPWT1 peptide was tested as a counter ion to proteins from breast cancer cell line SKBR3. MBP co-synthesised with survivin peptides were also used as alternative sources of counter ions (FIG. 10).

Figure 10:
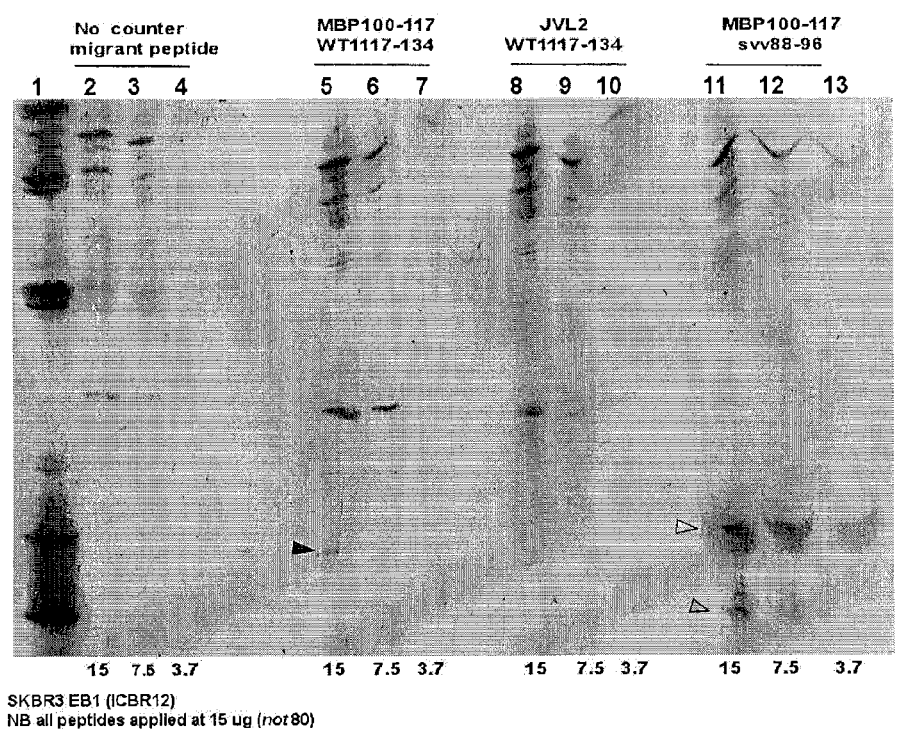
FIG. 10 shows CHIEF of MBPTAA peptides as counter ions to SKBR3 cytoplasmic proteins.

Small counter migrant complexes formed near the pI 6.8 marker when MBPWT1 peptide was placed as counter ion to SKBR3 proteins (FIG. 10, lane 5; arrowhead). However, a much larger band formed when MBPSVV88 was used as a counter ion against the same source of material (FIG. 10, lanes 9-13; top arrowhead). The increased degree of complex formation observed in FIG. 10 prompted a closer evaluation of MBP co-synthesized with the three chosen survivin peptides 20-28, isoform 3 88-96 and 96-104.

As seen in FIG. 10, there are some distinguishing bands in the first dimension IEF. However when these areas were excised from the CHIEF gel and processed for SDS-PAGE, the resulting profiles indicated the presence of both distinct and shared bands between the cytoplasmic proteins by MBPTAA peptide. The IEF process is non-denaturing and individual bands may represent multiple interacting proteins that remain in association in the non-ionic extraction buffer (in this instance containing the membrane permeabilising, but otherwise mild detergent, digitonin).

The presence of bands that could differentiate between a non-cancerous cell line (MCF10A), a weakly cancerous cell line (MCF7) and an aggressive metastasizing cell line (SKBR3) suggests the possibility of identifying virulence factors that could be used as early diagnostic, prognostic or therapeutic markers (for example, if cell lysates were prepared from biopsy material). The creation of a counter ion profile from specific clinical sample would only require limited material (note 7 µg is run per lane in FIG. 10). Further, multiple patients, or multiple points of reference for a single patient, could be run on the same gel. The possibility of identifying specific indices of cancer presence or progression also emphasized the discovery potential of mass spectrometry from even small amounts of material (µg range).

Example 11

Cell derived vesicles (CDVs) are normally used as vehicles for intercellular communication without the necessity for direct contact. However excessive vesicle release into the surrounding environment is a common feature of tumor cells and during inflammatory and immune response conditions as well as other diseases. Capture of CDVs from the extra cellular matrix is regarded as an important source of potential biomarkers, since proteins secreted by diseased cells such as cancer cells and/or infected cells may reflect the closest facsimile of biological interface between the diseased cell and the surrounding host tissue environment of the patient. CDVs for example comprise proteins and nucleic acids such as RNAs (coding and non) as well as miRNA, large intergenic non-coding RNAs (lincRNAs), as well as other molecules such as linear and branched polysaccharides. Capture of vesicles from plasma and other body fluids is also regarded as highly significant in that the encapsulated material represents a source of biologic materials otherwise inaccessible by contemporary methods. Molecules associated with vesicles may thus permit informed decisions regarding for example the earlier staging of cancer patients, treatment, monitoring and recurrence free survival. Peptide capture of vesicular material may thus facilitate clinical analysis by microarray and qRT-PCR.

Disease biomarkers can be identified for example by obtaining a biological fluid sample from a series of test subjects, e.g. subjects with a same disease such as cancer or disease stage) and isolating the CDVS. The isolation method utilizes a method disclosed herein and can further include one or more concentration steps, filtration steps and the like. Molecules such as RNA can be extracted from the CDVs and amplified for example using RT-PCR. Sequence analysis or mircroarray profiling can be used to determine the identity of such proteins. The results can be compared for example to a series of samples of control subjects not having the disease in question. Biomarkers that are statistically different between the two groups identify the biomarker as a disease biomarker.

Diagnostically and/or prognostically, the method can involve obtaining a biological fluid sample from a test subject with a disease such as cancer, isolating CDVs using a polypeptide described herein to form a complex with the CDV and determining the presence of one or more disease relevant substances in the complex (e.g. in the CDVs).

(a) contacting the sample from the subject with one or more peptides or polypeptides of the present application under conditions suitable for the binding of the of the one or more peptides or polypeptides to one or more CDVs to form complexes, (b) fractionating the complexes, and (c) detecting the presence of one or more substances in the CDVs The CDV substance detected can be for example be a specific protein or nucleic acid such as RNA associated with the disease or prognosis. The CDV substances can alternatively be profiled for example, using microarray to assess expression levels of a number of RNAs or proteins. The CDV substance can also be for example a miRNA, large intergenic non-coding RNAs (lincRNAs), and/or a linear and branched polysaccharides or any relevant molecule present in the CDV.

The presence of the one or more CDV substances for example a cancer relevant substance can be compared to a control sample, for example a sample from a same system that more closely conforms to normalcy or standard (e.g. diseased vs. healthy, polluted vs. undisturbed, treated vs. non-treated) .In other cases for example where expression or expression of a particular level of a protein or RNA is known to be associated with a disease, the control can be a numerical value.

CDVs being derived from cells carry with them molecules such as nucleic acids from their cell-of-origin, allowing real-time access to molecular genetic information about cells in the body without direct access to the diseased cells, thereby bypassing the requirement for biopsy which may be difficult or otherwise unattainable.

Example 12

Comparison of the amino acid sequence of MBP100-117 and lysozyme identifies sequence similarities.

```
                                           SEQ ID NO: 2
      PSQGKGRGLSLSRFSWGA MBP (bovine)

SEQ ID NO: 6
      GWGDRGNGFGLMQVDKRY Lysozyme (chicken)
       .:*.*:.*  :.
```

Where "*" means identical; ":" means conserved substitutions and "." means semi-conserved substitution (similar shapes).
Human lysozyme and chicken lysozyme have the following alignment.

```
      GWGDRGNGFGLMQVDKRY   SEQ ID NO: 6
      ..|||...:|:.|:::.||
      NAGDRSTDYGIFQINSRY   SEQ ID NO: 126
```

Similarly comparing bovine MBP 100-117 with human MBP identified similarities, bovine

```
      1   -PSQGKGRGLSLSRFSWGA   SEQ ID NO: 2
           ||||||........|.:|.
      101  PPSQGKGAEGQRPGFGYGG   SEQ ID NO: 127
```

Bovine MBP 100-117 aligns to amino acids 102 to 119 in human MBP.

The α-helix forming amino acid sequence that binds a heat shock protein comprises one or more hydrophobic or basic amino acids dispersed throughout the sequence, most importantly in the center positions (e.g. for a 18-mer, positions 5, 6, 7, 8, 9, 10, 11, 12, and 13 are considered center positions of the peptide), few or no acidic amino acids, and one or more uncharged polar, basic and/or aromatic amino acids flanking the hydrophobic groups.

The hydrophobic and basic amino acids are interpolated with smaller amino acids that allow for steric rotation, for example, serine and glycine. While not wishing to be limited by theory, it is believed that these smaller amino acids permit some spacing of the binding amino acids allowing them to interact with compatible electrostatic regions of the binding cleft of the associated protein (that being bound).

Accordingly, the amino acid types above are preferred to be intermittently spaced, so that a larger basic, uncharged polar and/or hydrophobic amino acid is followed by a smaller amino acid, in a repeating fashion.

Example 13

Polypeptides comprising the following were made:

```
MBP 100-108/Survivin 20-28,
                                    [SEQ ID NO: 68]
PSQGKGRGSTFKNWPFL MBP 105-113/Survivin 20-28,
                                    [SEQ ID NO: 69]
GRGLSLSRFSTFKNWPFL MBP 109-117/Survivin isoform 3 88-96,
                                    [SEQ ID NO: 70]
SLSRFSWGALRRKCAVPS MBP 109-117/Survivin 96-104
                                    [SEQ ID NO: 71]
SLSRFSWGALTLGEFLKL
```

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Full Citations for Documents Referred to in the specification

Al-Nedawi K, Meehan B, Micallef J, Lhotak V, May L, Guha A, Rak J. (2008) Intercellular transfer of the oncogenic receptor EGFRvIII by microvesicles derived from tumour cells. Nat Cell Biol. May; 10(5):619-24.

Anderson H C, Mulhall D, Garimella R. (2010) Role of extracellular membrane vesicles in the pathogenesis of various diseases, including cancer, renal diseases, atherosclerosis, and arthritis. Lab Invest. 90(11):1549-57.

Andersen M H, Sørensen R B, Schrama D, Svane I M, Becker J C, Thor Straten P Cancer treatment: the combination of vaccination with other therapies. Cancer Immunol Immunother. 2008 November; 57(11):1735-43.

Andreev O A, Engelman D M, Reshetnyak Y K. (2010) pH-sensitive membrane peptides (pHLIPs) as a novel class of delivery agents. Mol Membr Biol. 27(7):341-52.

Banerji U. (2009) Heat shock protein 90 as a drug target: some like it hot. Clin Cancer Res. 15(1):9-14.

Basu S, Binder R J, Ramalingam T, Srivastava P K. (2001) CD91 is a common receptor for heat shock proteins gp96, hsp90, hsp70, and calreticulin. Immunity. 14(3):303-13.

Bebawy M, Combes V, Lee E, Jaiswal R, Gong J, Bonhoure A, Grau G E. (2009) Membrane microparticles mediate transfer of P-glycoprotein to drug sensitive cancer cells. Leukemia. September; 23(9):1643-9.

Bechinger B. (2010); Membrane association and pore formation by alpha-helical peptides. Adv Exp Med. Biol. 677: 24-30.

Becker T, Hartl F U, Wieland F. (2002) CD40, an extracellular receptor for binding and uptake of Hsp70-peptide complexes. J. Cell Biol. 158(7):1277-85.

Bleifuss E, Bendz H, Sirch B, Thompson S, Brandl A, Milani V, Graner M W, Drexler I, Kuppner M, Katsanis E, Noessner E, Issels R D. (2008) Differential capacity of chaperone-rich lysates in cross-presenting human endogenous and exogenous melanoma differentiation antigens. Int J Hyperthermia. 24(8):623-37.

Binder R J, Blachere N E, Srivastava P K. (2001) Heat shock protein-chaperoned peptides but not free peptides introduced into the cytosol are presented efficiently by major histocompatibility complex I molecules. J Biol. Chem. 276 (20):17163-71.

Binder R J. (2008) Heat-shock protein-based vaccines for cancer and infectious disease. Expert Rev Vaccines. 7(3):383-93.

Binder R J. (2009) CD40-independent engagement of mammalian hsp70 by antigen-presenting cells. J. Immunol. 182(11):6844-50.

Bolhassani A, Rafati S. (2008) Heat-shock proteins as powerful weapons in vaccine development. Expert Rev Vaccines. 7(8):1185-99.

Brennan D J, Rexhepaj E, O'Brien S L, McSherry E, O'Connor D P, Fagan A, Culhane A C, Higgins D G, Jirstrom K, Millikan R C, Landberg G, Duffy M J, Hewitt S M, Gallagher W M Altered cytoplasmic-to-nuclear ratio of survivin is a prognostic indicator in breast cancer. Clin Cancer Res. 2008 May 1; 14(9):2681-9.

Broemer M, Krappmann D, Scheidereit C. (2004) Requirement of Hsp900 activity for IkappaB kinase (IKK) biosynthesis and for constitutive and inducible IKK and NF-kappaB activation. Oncogene. 23(31):5378-86.

Broquet A H, Thomas G, Masliah J, Trugnan G, Bachelet M. (2003) Expression of the molecular chaperone Hsp70 in detergent-resistant microdomains correlates with its membrane delivery and release. J Biol. Chem. 278(24):21601-6.

Bron P, Giudice E, Rolland J P, Buey R M, Barbier P, Diaz J F, Peyrot V, Thomas D, Garnier C. (2008) Apo-Hsp90 coexists in two open conformational states in solution.Biol Cell. 100(7):413-25.

Bukau B, Horwich A L. (1998) The Hsp70 and Hsp600 chaperone machines. Cell. 92(3):351-66.

Bukau B, Weissman J, Horwich A. (2006) Molecular chaperones and protein quality control. Cell. 125(3):443-51.

Camussi G, Deregibus M C, Bruno S, Cantaluppi V, Biancone L. (2010) Exosomes/microvesicles as a mechanism of cell-to-cell communication. Kidney Int. 78(9):838-48.

Cantrell J, Larmonier C, Janikashvili N, Bustamante S, Fraszczak J, Herrell A, Lundeen T, J LaCasse C, Situ E, Larmonier N, Katsanis E. (2010) Signaling pathways induced by a tumor-derived vaccine in antigen presenting cells. Immunobiology. 215(7):535-44.

Cappello F, Bellafiore M, Palma A, David S, Marcianò V, Bartolotta T, Sciume C, Modica G, Farina F, Zummo G, Bucchieri F. (2003) 60 KDa chaperonin (HSP60) is overexpressed during colorectal carcinogenesis. Eur J Histochem. 47(2):105-10.

Cappello F, Conway de Macario E, Marasa L, Zummo G, Macario A J. (2008) Hsp60 expression, new locations, functions and perspectives for cancer diagnosis and therapy. Cancer Biol Ther. 7(6):801-9.

Castellino F, Boucher P E, Eichelberg K, Mayhew M, Rothman J E, Houghton A N, Germain R N. (2000) Receptor-mediated uptake of antigen/heat shock protein complexes results in major histocompatibility complex class I antigen presentation via two distinct processing pathways. J Exp Med. June 5; 191(11):1957-64.

Chalmin F, Ladoire S, Mignot G, Vincent J, Bruchard M, Remy-Martin J P, Boireau W, Rouleau A, Simon B, Lanneau D, De Thonel A, Multhoff G, Hamman A, Martin F, Chauffert B, Solary E, Zitvogel L, Gamido C, Ryffel B, Borg C, Apetoh L, Rébé C, Ghiringhelli F. (2010) Membrane-associated Hsp72 from tumor-derived exosomes mediates STAT3-dependent immunosuppressive function of mouse and human myeloid-derived suppressor cells. J Clin Invest. 120(2):457-71.

Chen T, Cao X. (2010) Stress for maintaining memory: HSP70 as a mobile messenger for innate and adaptive immunity. Eur J. Immunol. 40(6):1541-4.

Chen C, Skog J, Hsu C H, Lessard R T, Balaj L, Wurdinger T, Carter B S, Breakefield X O, Toner M, Irimia D. (2010) Microfluidic isolation and transcriptome analysis of serum microvesicles. Lab Chip. 10(4):505-11

Ciupitu A M, Petersson M, O'Donnell C L, Williams K, Jindal S, Kiessling R, Welsh R M. (1998) Immunization with a lymphocytic choriomeningitis virus peptide mixed with heat shock protein 70 results in protective antiviral immunity and specific cytotoxic T lymphocytes. J Exp Med. 187(5): 685-91.

Coelho V, Broere F, Binder R J, Shoenfeld Y, Moudgil K D. (2008) Heat-shock proteins: inflammatory versus regulatory attributes. Cell Stress Chaperones. 13(2):119-25.

Corcoran C, Friel A M, Duffy M J, Crown J, O'Driscoll L. (2010) Intracellular and Extracellular MicroRNAs in Breast Cancer. Clin Chem. November EPub.

Davenport E L, Zeisig A, Aronson L I, Moore H E, Hockley S, Gonzalez D, Smith E M, Powers M V, Sharp S Y, Workman P, Morgan G J, Davies F E. (2010) Targeting heat shock protein 72 enhances Hsp90 inhibitor-induced apoptosis in myeloma. Leukemia. 24(10):1804-7.

Daugaard M, Jäättelä M, Rohde M. (2005) Hsp70-2 is required for tumor cell growth and survival. Cell Cycle. 4(7): 877-80.

Daugaard M, Rohde M, Jäättelä M. (2007) The heat shock protein 70 family: Highly homologous proteins with overlapping and distinct functions. FEBS Lett. 581:3702-10.

Davila S, Froeling F E, Tan A, Bonnard C, Boland G J, Snippe H, Hibberd M L, Seielstad M. (2010) New genetic associations detected in a host response study to hepatitis B vaccine. Genes Immun. 11(3):232-8.

Dempsey N C, Ireland H E, Smith C M, Hoyle C F, Williams J H. (2010) Heat Shock Protein translocation induced by membrane fluidization increases tumor-cell sensitivity to chemotherapeutic drugs. Cancer Lett. 296(2):257-67.

Drahl C (2008) Harnessing Helices Chemical & Engineering News 86(22): 18-23.

Enomoto Y, Bharti A, Khaleque A A, Song B, Liu C, Apostolopoulos V, Xing P X, Calderwood S K, Gong J (2006). Enhanced immunogenicity of heat shock protein 70 peptide complexes from dendritic cell-tumor fusion cells. J. Immunol. 177(9):5946-55.

Dunn G P, Bruce A T, Ikeda H, Old L J, Schreiber R D. Cancer immunoediting: from immunosurveillance to tumor escape. Nat. Immunol. 2002 November; 3(11):991-8

Evdonin A L, Martynova M G, Bystrova O A, Guzhova I V, Margulis B A, Medvedeva N D. (2006) The release of Hsp70 from A431 carcinoma cells is mediated by secretory-like granules. Eur J. Cell Biol. June; 85(6):443-55.

Flechtner J B, Cohane K P, Mehta S, Slusarewicz P, Leonard A K, Barber B H, Levey D L, Andjelic S. (2006) High-affinity interactions between peptides and heat shock protein 70 augment CD8+ T lymphocyte immune responses. J. Immunol. July 15; 177(2):1017-27.

Frydman J. (2001) Folding of newly translated proteins in vivo: the role of molecular chaperones. Annu Rev Biochem.; 70:603-47.

Gaiger A, Reese V, Disis M L, Cheever M A Immunity to WT1 in the animal model and in patients with acute myeloid leukemia. Blood. 2000 Aug. 15; 96(4):1480-9

Garcia J M, Garcia V, Peia C, Dominguez G, Silva J, Diaz R, Espinosa P, Citores M J, Collado M, Bonilla F. (2008) Extracellular plasma RNA from colon cancer patients is confined in a vesicle-like structure and is mRNA-enriched. RNA. 14(7):1424-32.

Graner M W, Raynes D A, Bigner D D, Gorier V. (2009) Heat shock protein 70-binding protein 1 is highly expressed in high-grade gliomas, interacts with multiple heat shock protein 70 family members, and specifically binds brain tumor cell surfaces. Cancer Sci. 100(10):1870-9.

Gyurkocza B, Plescia J, Raskett C M, Garlick D S, Lowry P A, Carter B Z, Andreeff M, Meli M, Colombo G, Altieri D C. Antileukemic activity of shepherdin and molecular diversity of hsp90 inhibitors. J Natl Cancer Inst. 2006 Aug. 2; 98(15):1068-77.

Henderson B, Pockley A G. (2010a) Molecular chaperones and protein-folding catalysts as intercellular signaling regulators in immunity and inflammation. J Leukoc Biol. 88(3): 445-62.

Henderson B, Calderwood S K, Coates A R, Cohen I, van Eden W, Lehner T, Pockley A G. (2010b) Caught with their PAMPs down? The extracellular signalling actions of molecular chaperones are not due to microbial contaminants. Cell Stress Chaperones. March; 15(2):123-41.

Henderson B. (2010c) Integrating the cell stress response: a new view of molecular chaperones as immunological and physiological homeostatic regulators. Cell Biochem Funct. 28(1):1-14.

Hendrix A, Westbroek W, Bracke M, Wever O D. (2010) An Ex(O)citing Machinery for Invasive Tumor Growth. Cancer Res. EPub November 23.

Hong B S, Cho J H, Kim H, Choi E J, Rho S, Kim J, Kim J H, Choi D S, Kim Y K, Hwang D, Gho Y S. (2009) Colorectal cancer cell-derived microvesicles are enriched in cell cycle-related mRNAs that promote proliferation of endothelial cells. BMC Genomics. 10:556, Horváth I, Multhoff G, Sonnleitner A, Vigh L. (2008) Membrane-associated stress proteins: more than simply chaperones. Biochim Biophys Acta. 1778(7-8):1653-64.

Huang Q, Richmond J F, Suzue K, Eisen H N, Young R A. (2000) In vivo cytotoxic T lymphocyte elicitation by mycobacterial heat shock protein 70 fusion proteins maps to a discrete domain and is CD4(+) T cell independent. J Exp Med. January 17; 191(2):403-8.

Iguchi H, Kosaka N, Ochiya T. (2010) Secretory microRNAs as a versatile communication tool. Commun Integr Biol. 3(5):478-81.

Ishii T, Udono H, Yamano T, Ohta H, Uenaka A, Ono T, Hizuta A, Tanaka N, Srivastava P K, Nakayama E. (1999) Isolation of MHC class I-restricted tumor antigen peptide and its precursors associated with heat shock proteins hsp70, hsp90, and gp96. J. Immunol. 162(3):1303-9.

Jäättelä M. (1995) Over-expression of hsp70 confers tumorigenicity to mouse fibrosarcoma cells. Int J Cancer. 3; 60(5):689-93.

Jacobson R M, Poland G A. (2004) The genetic basis for measles vaccine failure. Acta Paediatr Suppl. 93(445):43-6.

Jung T, Castellana D, Klingbeil P, Cuesta Hernandez I, Vitacolonna M, Orlicky D J, Roffler S R, Brodt P, Zöller M. (2009) CD44v6 dependence of premetastatic niche preparation by exosomes. Neoplasia. 11(10):1093-105.

Karapanagiotou E M, Syrigos K, Saif M W (2009) Heat shock protein inhibitors and vaccines as new agents in cancer treatment. Expert Opin Investig Drugs. 18(2):161-74.

Kelber J A, Panopoulos A D, Shani G, Booker E C, Belmonte J C, Vale W W, Gray P C. Blockade of Crypto binding to cell surface GRP78 inhibits oncogenic Crypto signaling via MAPK/PI3K and Smad2/3 pathways. Oncogene. 2009 Jun. 18; 28(24):2324-36.

Khan S, Jutzy J M, Aspe J R, McGregor D W, Neidigh J W, Wall N R (2010) Survivin is released from cancer cells via exosomes. Apoptosis. August 18.

Keller S, Kdnig A K, Marme F, Runz S, Wolterink S, Koensgen D, Mustea A, Sehouli J, Altevogt P. (2009) Systemic presence and tumor-growth promoting effect of ovarian carcinoma released exosomes. Cancer Lett. 278(1):73-81.

Kislin K L, Marron M T, Li G, Graner M W, Katsanis E. (2007) Chaperone-rich cell lysate embedded with BCR-ABL peptide demonstrates enhanced anti-tumor activity against a murine BCR-ABL positive leukemia. FASEB J. July; 21(9): 2173-84.

Lakkaraju A, Rodriguez-Boulan E (2008) Itinerant exosomes: emerging roles in cell and tissue polarity. Trends Cell Biol. 18(5):199-209.

Lancaster G I, Febbraio M A. (2005) Exosome-dependent trafficking of HSP70: a novel secretory pathway for cellular stress proteins. J Biol. Chem. 280(24):23349-55.

Lewis J, Devin A, Miller A, Lin Y, Rodriguez Y, Neckers L, Liu Z G. (2000) Disruption of hsp90 function results in degradation of the death domain kinase, receptor-interacting protein (RIP), and blockage of tumor necrosis factor-induced nuclear factor-kappaB activation. J Biol. Chem. 275(14):10519-26.

Li G, Andreansky S, Helguera G, Sepassi M, Janikashvili N, Cantrell J, Lacasse C L, Larmonier N, Penichet M L, Katsanis E. (2008) A chaperone protein-enriched tumor cell lysate vaccine generates protective humoral immunity in a mouse breast cancer model. Mol Cancer Ther. 7(3):721-9.

Liu C, Yu S, Zinn K, Wang J, Zhang L, Jia Y, Kappes J C, Barnes S, Kimberly R P, Grizzle W E, Zhang H G. (2006) Murine mammary carcinoma exosomes promote tumor growth by suppression of NK cell function. J. Immunol. 176 (3):1375-85.

Liu Y, Steiniger S C, Kim Y, Kaufmann G F, Felding-Habermann B, Janda K D Mechanistic studies of a peptidic GRP78 ligand for cancer cell-specific drug delivery. Mol. Pharm. 2007 May-June; 4(3):435-47.

Mahotka C, et al. (1999) Survivin-deltaEx3 and survivin-2B: two novel splice variants of the apoptosis inhibitor survivin with different antiapoptotic properties. Cancer Res. December 15; 59(24):6097-102.

Mahotka C, Wenzel M, Springer E, Gabbert H E, Gerharz C D Survivin-deltaEx3 and survivin-2B: two novel splice variants of the apoptosis inhibitor survivin with different antiapoptotic properties. Cancer Res. 1999 Dec. 15; 59(24): 6097-10

Mambula S S, Calderwood S K. (2006) Heat shock protein 70 is secreted from tumor cells by a nonclassical pathway involving lysosomal endosomes. J. Immunol. 177(11):7849-57.

McCready J, Sims J D, Chan D, Jay D G. (2010) Secretion of extracellular hsp90alpha via exosomes increases cancer cell motility: a role for plasminogen activation. BMC Cancer. 16; 10:294.

Meckes D G Jr, Shair K H, Marquitz A R, Kung C P, Edwards R H, Raab-Traub N. (2010) Human tumor virus utilizes exosomes for intercellular communication. Proc Natl Acad Sci USA. 107(47):20370-5

Michielin O, Blanchet J S, Fagerberg T, Valmori D, Rubio-Godoy V, Speiser D, Ayyoub M, Alves P, Luescher I, Gairin J E, Cerottini J C, Romero P. (2005) Tinkering with nature: the tale of optimizing peptide based cancer vaccines. Cancer Treat Res123:267-91.

Misra U K, Mowery Y, Kaczowka S, Pizzo S V. Ligation of cancer cell surface GRP78 with antibodies directed against its COOH-terminal domain up-regulates p53 activity and promotes apoptosis. Mol Cancer Ther. 2009 May; 8(5):1350-62.

Morol Y, Mayhew M, Trcka J, Hoe M H, Takechi Y, Hartl F U, Rothman J E, Houghton A N. (2000) Induction of cellular immunity by immunization with novel hybrid peptides complexed to heat shock protein 70. Proc Natl Acad Sci U S A. 97(7):3485-90.

Nakajima H, Kawasaki K, Oka Y, Tsuboi A, Kawakami M, Ikegame K, Hoshida Y, Fujiki F, Nakano A, Masuda T, Wu F, Taniguchi Y, Yoshihara S, Elisseeva O A, Oji Y, Ogawa H, Azuma I, Kawase I, Aozasa K, Sugiyama H. WT1 peptide vaccination combined with BCG-CWS is more efficient for tumor eradication than WT1 peptide vaccination alone. Cancer Immunol Immunother. 2004 July; 53(7):617-24.

Nilsson J, Skog J, Nordstrand A, Baranov V, Mincheva-Nilsson L, Breakefield X O, Widmark A. (2009) Prostate cancer-derived urine exosomes: a novel approach to biomarkers for prostate cancer. Br J Cancer. 100(10):1603-7.

Nishikawa M, Takemoto S, Takakura Y. (2008) Heat shock protein derivatives for delivery of antigens to antigen presenting cells. Int J. Pharm. 354(1-2):23-7.

Oka Y, Tsuboi A, Taguchi T, Osaki T, Kyo T, Nakajima H, Elisseeva O A, Oji Y, Kawakami M, Ikegame K, Hosen N, Yoshihara S, Wu F, Fujiki F, Murakami M, Masuda T, Nishida S, Shirakata T, Nakatsuka S, Sasaki A, Udaka K, Dohy H, Aozasa K, Noguchi S, Kawase I, Sugiyama H. Induction of WT1 (Wilms' tumor gene)-specific cytotoxic T lymphocytes by WT1 peptide vaccine and the resultant cancer regression. Proc Natl Acad Sci USA. 2004 Sep. 21; 101(38):13885-90.

Park J E, Tan H S, Datta A, Lai R C, Zhang H, Meng W, Lim S K, Sze S K. (2010) Hypoxic tumor cell modulates its microenvironment to enhance angiogenic and metastatic potential by secretion of proteins and exosomes. Mol Cell Proteomics. June; 9(6):1085-99.

Patgiri A, Jochim A L, Arora P S. (2008) A hydrogen bond surrogate approach for stabilization of short peptide sequences in alpha-helical conformation. Acc Chem. Res. 41(10): 1289-300.

Pfister K, Radons J, Busch R, Tidball J G, Pfeifer M, Freitag L, Feldmann H J, Milani V, Issels R, Multhoff G. (2007) Patient survival by Hsp70 membrane phenotype: association with different routes of metastasis. Cancer. 110(4): 926-35.

Powers M V, Clarke P A, Workman P. (2009) Death by chaperone: HSP90, HSP70 or both? Cell Cycle. 8(4):518-26.

Powers M V, Workman P. (2007) Inhibitors of the heat shock response: biology and pharmacology. FEBS Lett. 581 (19):3758-69.

Powers M V, Jones K, Barillari C, Westwood I, van Montfort R L, Workman P. (2010) Targeting HSP70: The second potentially druggable heat shock protein and molecular chaperone? Cell Cycle. 9(8).

Qian S B, McDonough H, Boellmann F, Cyr D M, Patterson C. (2006) CHIP-mediated stress recovery by sequential ubiquitination of substrates and Hsp70. Nature. 440(7083): 551-5.

Quesenberry P J, Dooner M S, Aliotta J M. (2010a) Stem cell plasticity revisited: the continuum marrow model and phenotypic changes mediated by microvesicles. Exp Hematol. July; 38(7):581-93.

Quesenberry P J, Aliotta J M. (2010b) Cellular phenotype switching and microvesicles. Adv Drug Deliv Rev. 62(12): 1141-8.

Rak, J.; Al-Nedawi, K; Meehan, B.; Guha, A. PCT Patent Application Publication No. WO2009/021 322, Feb. 19, 2009.

Rak J. (2010) Microparticles in cancer. Semin Thromb Hemost. 36(8):888-906.

Ramos R R, Swanson A J, Bass J. (2007) Calreticulin and Hsp900 stabilize the human insulin receptor and promote its mobility in the endoplasmic reticulum. Proc Natl Acad Sci USA. June 19; 104(25):10470-5.

Redlak M J, Miller T A (2010) Targeting PI3K/Akt/HSP90 Signaling Sensitizes Gastric Cancer Cells to Deoxycholate-Induced Apoptosis. Dig Dis Sci.

Reker S, Meier A, Holten-Andersen L, Svane I M, Becker J C, thor Straten P, Andersen M H Identification of novel survivin-derived CTL epitopes. Cancer Biol Ther. 2004 February; 3(2):173-9.

Renzulli J F 2nd, Del Tatto M, Dooner G, Aliotta J, Goldstein L, Dooner M, Colvin G, Chatterjee D, Quesenberry P. (2010) Microvesicle induction of prostate specific gene expression in normal human bone marrow cells. J Urol. November; 184(5):2165-71.

Rexhepaj E, Jirstrom K, O'Connor D P, O'Brien S L, Landberg G, Duffy M J, Brennan D J, Gallagher W M Validation of cytoplasmic-to-nuclear ratio of survivin as an indicator of improved prognosis in breast cancer. BMC Cancer. 2010 Nov. 23; 10:639.

Rezai T, Bock J E, Zhou M V, Kalyanaraman C, Lokey R S, Jacobson M P. (2006) Conformational flexibility, internal hydrogen bonding, and passive membrane permeability: successful in silico prediction of the relative permeabilities of cyclic peptides. J Am Chem. Soc. 128(43):14073-80.

Rohde M, Daugaard M, Jensen M H, Helin K, Nylandsted J, Juattela M. (2005) Members of the heat-shock protein 70 family promote cancer cell growth by distinct mechanisms. Genes Dev. March 1; 19(5):570-82.

Sabatino G, Papini A M. (2008) Advances in automatic, manual and microwave-assisted solid-phase peptide synthesis. Curr Opin Drug Discov Devel. 11(6):762-70

Scriven P, Brown N J, Pockley A G, Wyld L. (2007) The unfolded protein response and cancer: a brighter future unfolding? J Mol. Med. 85(4):331-41.

Shani G, Fischer W H, Justice N J, Kelber J A, Vale W, Gray P C. GRP78 and Crypto form a complex at the cell surface and collaborate to inhibit transforming growth factor beta signaling and enhance cell growth. Mol Cell Biol. 2008 January; 28(2):666-77

Sherman M, Multhoff G. (2007) Heat shock proteins in cancer. Ann N Y Acad. Sci. 1113:192-201.

Sidera K, Patsavoudi E. Extracellular HSP90: conquering the cell surface. Cell Cycle. 2008 Jun. 1; 7(11):1564-8

Simons M, Raposo G. (2009) Exosomes—vesicular carriers for intercellular communication. Curr Opin Cell Biol. 21(4):575-81.

Skog J, WUrdinger T, van Rijn S, Meijer D H, Gainche L, Sena-Esteves M, Curry W T Jr, Carter B S, Krichevsky A M, Breakefield X O. (2008) Glioblastoma microvesicles transport RNA and proteins that promote tumour growth and provide diagnostic biomarkers. Nat Cell Biol. 10(12):1470-6.

Spisek R, Dhodapkar M V. Towards a better way to die with chemotherapy: role of heat shock protein exposure on dying tumor cells. Cell Cycle. 2007 Aug. 15; 6(16):1962-5.

Stocki P, Morris N J, Preisinger C, Wang X N, Kolch W, Multhoff G, Dickinson A M. (2010) Identification of potential HLA class I and class II epitope precursors associated with heat shock protein 70 (HSPA). Cell Stress Chaperones. 15(5):729-41.

Su X, Sykes J B, Ao L, Raeburn C D, Fullerton D A, Meng X. (2010) Extracellular heat shock cognate protein 70 induces cardiac functional tolerance to endotoxin: differential effect on TNF-alpha and ICAM-1 levels in heart tissue. Cytokine. 51(1):60-6.

Suto R, Srivastava P K (1995) A mechanism for the specific immunogenicity of heat shock protein-chaperoned peptides. Science. 269(5230): 1585-8.

Szajnik M, Czystowska M, Szczepanski M J, Mandapathil M, Whiteside T L. (2010) Tumor-derived microvesicles induce, expand and up-regulate biological activities of human regulatory T cells (Treg). PLoS One.

Tobian A A, Canaday D H, Boom W H, Harding C V: (2004) Bacterial heat shock proteins promote CD91-dependent class I MHC cross-presentation of chaperoned peptide to CD8+ T cells by cytosolic mechanisms in dendritic cells versus vacuolar mechanisms in macrophages. J. Immunol. 172(9):5277-86.

Tsutsumi S, Neckers L. Extracellular heat shock protein 90: a role for a molecular chaperone in cell motility and cancer metastasis. Cancer Sci. 2007 October; 98(10):1536-9.

Tsutsumi S, Scroggins B, Koga F, Lee M J, Trepel J, Felts S, Carreras C, Neckers L. A small molecule cell-impermeant Hsp900 antagonist inhibits tumor cell motility and invasion. Oncogene. 2008 Apr. 10; 27(17):2478-87.

Tyndall J D, Nail T, Fairlie D P. (2005) Proteases universally recognize beta strands in their active sites. Chem. Rev. 105(3):973-99.

Valadi H, Ekström K, Bossios A, SjBstrand M, Lee J J, Lttvall J O. (2007) Exosome-mediated transfer of mRNAs and microRNAs is a novel mechanism of genetic exchange between cells. Nat Cell Biol. 9(6):654

Valenti R, Huber V, Iero M, Filipazzi P, Parmiani G, Rivoltini L. (2007) Tumor-released microvesicles as vehicles of immunosuppression. Cancer Res. 67(7):2912-5

Vanaja D K, Grossmann M E, Celis E, Young C Y (2000) Tumor prevention and antitumor immunity with heat shock protein 70 induced by 15-deoxy-deltal-2,14-prostaglandin J2 in transgenic adenocarcinoma of mouse prostate cells. Cancer Res. 60(17):4714-8.

Webber J, Steadman R, Mason M D, Tabi Z, Clayton A. (2010) Cancer Exosomes Trigger Fibroblast to Myofibroblast Differentiation. Cancer Res. November Epub.

Whitaker H C, Stanbury D P, Brinham C, Girling J, Hanrahan S, Totty N, Neal D E. Labeling and identification of LNCaP cell surface proteins: a pilot study. Prostate. 2007 Jun. 15; 67(9):943-54.

Wobser M, Keikavoussi P, Kunzmann V, Weininger M, Andersen M H, Becker J C Complete remission of liver metastasis of pancreatic cancer under vaccination with a HLA-A2 restricted peptide derived from the universal tumor antigen survivin. Cancer Immunol Immunother. 2006 October; 55(10):1294-8.

Yam A Y, Albanese V, Lin H T, Frydman J (2005) Hsp110 cooperates with different cytosolic HSP70 systems in a pathway for de novo folding. J Biol. Chem. 280(50):41252-61.

Young J C, Agashe V R, Siegers K, Hartl F U (2004) Pathways of chaperone-mediated protein folding in the cytosol. Nat Rev Mol Cell Biol. 5 (10):781-91.

Xiang X, Liu Y, Zhuang X, Zhang S, Michalek S, Taylor D D, Grizzle W, Zhang H G. (2010) TLR2-mediated expansion of MDSCs is dependent on the source of tumor exosomes. Am J Pathol. 177(4):1606-10.

Xie Y, Bai O, Yuan J, Chibbar R, Slattery K, Wei Y, Deng Y, Xiang J. (2009) Tumor apoptotic bodies inhibit CTL responses and antitumor immunity via membrane-bound transforming growth factor-beta1 inducing CD8+ T-cell anergy and CD4+ Tr1 cell responses. Cancer Res, October 1; 69(19):7756-66.

Zhang T, Li Y, Yu Y, Zou P, Jiang Y, Sun D. (2009) Characterization of celastrol to inhibit hsp90 and cdc37 interaction. J Biol Chem 284(51):35381-9

What is claimed is:

1. A polypeptide comprising:

(a) a first peptide portion consisting of an α-helix-forming amino acid sequence of myelin basic protein having the amino acid sequence of PSQGKGRGLSLSRFSWGA [SEQ ID NO 2:] or a sequence having one amino acid deletion, addition or substitution relative to [SEQ ID NO 2]; and (b) at least one second peptide portion comprising a tumour associated antigen (TAA) epitope of survivin at least 8 amino acids in length or a sequence having one amino acid deletion, or substitution relative to the epitope of survivin.

2. The polypeptide of claim 1, wherein the at least one second peptide portion comprises one or more of:

```
                                            [SEQ ID NO: 7]
STFKNWPFL,

[SEQ ID NO: 8]
LTLGEFLKL;
or

[SEQ ID NO: 9]
LRRKCAVPS or a sequence having one amino acid deletion,
addition or substitution relative to [SEQ ID NO:
7], [SEQ ID NO: 8] or [SEQ ID NO: 9].
```

3. The polypeptide of claim 1, wherein the first peptide portion is at the N-terminus of the polypeptide and comprises one second peptide portion at the C-terminus.

4. The polypeptide of claim 1, wherein the first peptide portion of the polypeptide is located between two second peptide portions, which is the same or different.

5. The polypeptide of claim 1, comprising an amino acid sequence selected from:

```
                                           [SEQ ID NO: 64]
PSQGKGRGLSLSRFSWGASTFKNWPFL;

[SEQ ID NO: 65]
PSQGKGRGLSLSRFSWGALTLGEFLKL;
and

[SEQ ID NO: 66]
PSQGKGRGLSLSRFSWGALRRKCAVPS or a sequence having one or two amino acid
deletions, additions or substitutions relative to
[SEQ ID NO: 64], [SEQ ID NO: 65] or [SEQ ID NO:
66]
```

6. The polypeptide of claim 1, further comprising a linker moiety, a secondary modification or label.

7. A nucleic acid encoding the polypeptide of claim 1.

8. A composition comprising the polypeptide of claim 1, and one or more additives, excipients and/or adjuvants.

9. A method of fractionating one or more substances relevant for discovery, research or clinical analysis from a biological sample comprising: (a) contacting the biological sample with one or more of the polypeptides of claim 1 under conditions suitable for binding of the one or more polypeptides to the one or more substances to form complexes, and (b) fractionating the complexes.

10. A method of identifying substances for diagnosing an infectious disease or cancer in a subject comprising: (a) contacting a sample from the subject with one or more polypeptides of claim 1 under conditions suitable for the binding of the of the one or more peptides or polypeptides to one or more infectious disease and/or cancer relevant substances to form complexes, (b) fractionating the complexes, and (c) identifying the presence of the one or more infectious disease and/or cancer relevant substances in the complexes, wherein the one or more infectious disease and/or cancer relevant substances are comprised in an HSP associated complex.

11. A method of inducing an immune response comprising administering an effective amount of one or more of the polypeptide of claim 1 to a subject in need thereof.

12. The polypeptide of claim 1, wherein the first peptide portion comprises the sequence: PSQGKGRGLSLSRF-SWGA [SEQ ID NO 2:].

13. The polypeptide of claim 2, wherein the TAA comprises the amino acid sequence of: LTLGEFLKL [SEQ ID NO:8].

14. The polypeptide of claim 1, comprising an amino acid sequence at least 90% identical to PSQGKGRGLSLSRF-SWGALTLGEFLKL [SEQ ID NO: 65].

15. The polypeptide of claim 1, further comprising one of more of a phosphorylation, acylation, acetylation, formylation, glycosylation, amidation, incorporation of chromophores, fluorescent dyes/fluorogenic groups, PEGylation, biotinylation and sulfation.

16. The polypeptide of claim 1, wherein the polypeptide is linked to a solid support.

17. A complex comprising the polypeptide of claim 1 and a heat shock protein, wherein the polypeptide and heat shock protein are affinity associated.

18. The complex of claim 17 wherein the heat shock protein is selected from HSP60, HSP70, HSP90 or HSP27 or an isoform thereof.

19. A vector comprising the nucleic acid of claim 7.

20. The composition of claim 8, wherein the one or more additives comprises a detergent matrix.

21. The method of claim 9, wherein the one or more substances relevant for discovery, research or clinical analysis are proteins.

22. The method of claim 9, wherein the one or more substances relevant for discovery, research or clinical analysis are cell derived vesicles (CDVs).

23. The method of claim 9, wherein the one or more substances relevant for discovery, research or clinical analysis are HSPs or HSP-associated complexes.

24. The method of claim 23, wherein the HSP is HSP60, HSP70, HSP90 or HSP27 or an isoform thereof.

25. The method of claim 9, wherein the biological sample is a bodily fluid.

26. The method of claim 25, wherein the bodily fluid is selected from blood, plasma, urine, cerebrospinal fluid, lymph, ascites, saliva, lavage, semen, glandular secretions, feces, exudates and contents of cysts.

27. The method of claim 9, wherein the conditions suitable for binding of the one or more polypeptides to the one or more substances to form complexes comprise counter affinity isoelectric focusing.

28. The method of claim 9, wherein the conditions suitable for binding of the one or more polypeptides to the one or more substances to form complexes comprise contacting solutions of the one or more peptides with the biological sample in a biologically relevant solution and optionally applying agitation, heat and/or microwaves.

29. The method of claim 9, wherein the one or more substances relevant for discovery, research or clinical analysis are substances for diagnosing an infectious disease or cancer in a subject.

30. A kit comprising the one or more of the polypeptides claim 1 and a dilution buffer.

\* \* \* \* \*

UNITED STATES PATENT AND TRADEMARK OFFICE
CERTIFICATE OF CORRECTION

PATENT NO. : 8,956,878 B2
APPLICATION NO. : 13/824829
DATED : February 17, 2015
INVENTOR(S) : Steven Gareth Griffiths et al.

Page 1 of 1

It is certified that error appears in the above-identified patent and that said Letters Patent is hereby corrected as shown below:

In the Claims

In claim 10, column 103, line 3, delete "the of the" and replace with --of the-- therefor.

In claim 30, column 104, line 34, delete "the one or more of the polypeptides" and replace with --one or more of the polypeptides of-- therefor.

Signed and Sealed this
Ninth Day of June, 2015

Michelle K. Lee
*Director of the United States Patent and Trademark Office*